(12) United States Patent
Wang et al.

(10) Patent No.: US 12,037,391 B2
(45) Date of Patent: Jul. 16, 2024

(54) ANTI-DLL3 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Haiqun Jia, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 836 days.

(21) Appl. No.: 15/733,747

(22) PCT Filed: Apr. 30, 2019

(86) PCT No.: PCT/US2019/029888
§ 371 (c)(1),
(2) Date: Oct. 14, 2020

(87) PCT Pub. No.: WO2019/217145
PCT Pub. Date: Nov. 14, 2019

(65) Prior Publication Data
US 2021/0047399 A1  Feb. 18, 2021

Related U.S. Application Data

(60) Provisional application No. 62/668,427, filed on May 8, 2018, provisional application No. 62/754,207, filed on Nov. 1, 2018, provisional application No. 62/787,815, filed on Jan. 3, 2019.

(51) Int. Cl.
| | |
|---|---|
| *G01N 33/53* | (2006.01) |
| *C07K 16/00* | (2006.01) |
| *C07K 16/28* | (2006.01) |
| *C07K 16/30* | (2006.01) |
| *C07K 16/46* | (2006.01) |
| *G01N 33/574* | (2006.01) |

(52) U.S. Cl.
CPC .......... *C07K 16/28* (2013.01); *C07K 16/2803* (2013.01); *C07K 16/30* (2013.01); *G01N 33/57492* (2013.01); *C07K 2317/24* (2013.01); *C07K 2317/31* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 2006/0121049 A1 | 6/2006 | Letourneur |
| 2011/0312505 A1 | 12/2011 | Reddy |
| 2012/0042416 A1 | 2/2012 | Schleker |
| 2012/0195831 A1 | 8/2012 | Zhang |
| 2016/0130356 A1 | 5/2016 | Desander |
| 2019/0225685 A1 | 7/2019 | Isse |

FOREIGN PATENT DOCUMENTS

| | | |
|---|---|---|
| WO | 2007080597 | 7/2007 |
| WO | 2011093097 | 8/2011 |
| WO | 2013126746 | 8/2013 |
| WO | 2014125273 | 8/2014 |
| WO | 2014130879 | 8/2014 |
| WO | 2015127407 | 8/2015 |
| WO | 2016138038 | 9/2016 |
| WO | 2016141285 | 9/2016 |
| WO | 2017021349 | 2/2017 |
| WO | 2017147368 | 8/2017 |
| WO | 2017201442 | 11/2017 |
| WO | 2018057669 A1 | 3/2018 |
| WO | 2019131988 | 7/2019 |
| WO | 2019195408 | 10/2019 |
| WO | 2019234220 | 12/2019 |
| WO | 2020069028 | 4/2020 |
| WO | 2020076977 | 4/2020 |

OTHER PUBLICATIONS

Cortinovis et al. Harnessing DLL3 inhibition: From old promises to new therapeutic horizons. Front Med (Lausanne). 2022; 9: 989405. (Year: 2022).*
Primeau A.B., Rovalpituzumab Tesirine Fails to Improve Outcomes in SCLC. Cancer Therapy Advisor, Mar. 25, 2021, pp. 1-3. (Year: 2021).*
The ASCO Post Staff. Several Studies Show Rovalpituzumab Tesirine Is Ineffective Against SCLC. The ASCO Post. pp. 1-4, Sep. 7, 2021. (Year: 2021).*
UniProt, (Jan. 11, 2011), Database accession No. E3RP86_PYRTT (Retrieved Augst 22, 2019) from internet <URL:https://www.uniprot.org/uniprot/E3RP86>.
International Search Report and Written Opinion for PCT/US2019/029888, dated Sep. 17, 2019, 12 pages.
Dunwoodie et al., "Axial skeletal defects caused by mutation in the spondylocostal dysplasia/pudgy gene DII3 are associated with disruption of the segmentation clock within the presomitic mesoderm", Development 129:1795-806 (2002).
Ntziachristos et al., "From Fly Wings to Targeted Cancer Therapies: A Centennial for Notch Signaling", Cancer Cell 25(3):318-34 (2014).
Chapman et al., "Notch inhibition by the ligand Delta-Like 3 defines the mechanism of abnormal vertebral segmentation in spondylocostal dysostosis", Hum Mol Genet 20(5):905-16 (2011).

(Continued)

*Primary Examiner* — Maher M Haddad
(74) *Attorney, Agent, or Firm* — Ice Miller LLP

(57) ABSTRACT

Anti-DLL3 antibodies and antigen-binding fragments thereof, anti-CD47 antibodies and antigen-binding fragments thereof, and anti-CD47/DLL3 bispecific antibodies and antigen-binding fragments thereof are described. Also described are nucleic acids encoding the antibodies, compositions comprising the antibodies, and methods of producing the antibodies and using the antibodies for treating or preventing diseases, such as cancer and/or associated complications.

9 Claims, 11 Drawing Sheets

Specification includes a Sequence Listing.

(56) References Cited

OTHER PUBLICATIONS

Geffers et al., "Divergent functions and distinct localization of the Notch ligands DLL1 and DLL3 in vivo", J Cell Biol 178(3):465-76 (2007).
Uhlen et al., "A pathology atlas of the human cancer transcriptome", Science 357(6352): eaan2507 (2017).
Saunders et al., "A DLL3-targeted antibody-drug conjugate eradicates high-grade pulmonary neuroendocrine tumor-initiating cells in vivo", Sci Transl Med 7(302):302ra136 (2015).
Sharma et al., "Noninvasive Interrogation of DLL3 Exression in Metastatic Small Cell Lung Cancer", Cancer Res 77(14):3931-41 (2017).
Barretina et al., "The Cancer Cell Line Encyclopedia enambles predictive modelling of anticancer drug sensitivity", Nature 483(7391):603-7 (2012).
Weiskopf et al., "CD47-blocking immunotherapies stimulate macrophage-mediated destruction of small-cell lung cancer", J Clin Invest 126(7):2610-2620 (2016).
Merchant et al., "An efficient route to human bispecific IgG", Nat. Biotechnol. 16(7):677-81 (1998).
Paz-Ares, Luis et al. "Tarlatamab, a First-in-Class DLL3-Targeted Bispecific T-Cell Engager, in Recurrent Small-Cell Lung Cancer: An Open-Label, Phase I Study," Journal of Clinical Oncology, vol. 41, issue 16 (Jun. 2023) pp. 2893-2903.
Wermke, Martin et al. "First-in-human dose-escalation trial of BI 764532, a delta-like ligand 3 (DLL3)/CD3 IgG-like T-cell engager in patients (pts) with DLL3-positive (DLL3+) small-cell lung cancer (SCLC) and neuroendocrine carcinoma (NEC)," Journal of Clinical Oncology, vol. 41, No. 16 (May 2023) p. 8502.
Choudhury, N. et al., "Interim results from a phase I/II study of HPN328, a tri-specific, half-life (T1/2) extended DLL3-targeting T cell engager in patients (pts) with small cell lung cancer (SCLC) and other neuroendocrine neoplasms (NEN)," 698P, Annals of Oncology, vol. 34, supplement 2 (Oct. 2023) S486.
Rudin, Charles M. et al. "Emerging therapies targeting the delta-like ligand 3 (DLL3) in small cell lung cancer," Journal of Hematology & Oncology, vol. 16, No. 66 (Jun. 2023) pp. 1-21.
Blackhall, Fiona et al. "Efficacy and Safety of Rovalpituzumab Tesirine Compared With Topotecan as Second-Line Therapy in DLL3-High SCLC: Results From the Phase 3 Tahoe Study," Journal of Thoracic Oncology, vol. 16, issue 9 (Sep. 2021) pp. 1547-1558.

\* cited by examiner

ANTI-DLL3 ANTIBODIES AND USES THEREOF

CROSS REFERENCE TO RELATED APPLICATIONS

This application is a Section 371 of International Application No. PCT/US2019/029888, filed Apr. 30, 2019, which published in the English language on Nov. 14, 2019 under International Publication No. WO 2019/217145 A8, which claims priority to U.S. Provisional Application 62/787,815, filed on Jan. 3, 2019; U.S. Provisional Application No. 62/754,207, filed on Nov. 1, 2018; and U.S. Provisional Application No. 62/668,427, filed on May 8, 2018. Each disclosure is incorporated herein by reference in its entirety.

FIELD OF THE INVENTION

This invention relates to monoclonal anti-DLL3 antibodies, anti-CD47 antibodies, and anti-CD47/DLL3 bispecific antibodies, nucleic acids and expression vectors encoding the antibodies, recombinant cells containing the vectors, and compositions comprising the antibodies. Methods of making the antibodies, and methods of using the antibodies to treat diseases including cancer and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "065799_15US2_Sequence_Listing" and a creation date of Oct. 7, 2020 and having a size of 70 kb. The sequence listing submitted via EFS-Web is part of the specification and is herein incorporated by reference in its entirety.

BACKGROUND OF THE INVENTION

Delta like canonical Notch ligand 3 (DLL3), also known as delta like 3 or delta like protein 3, is required for somite segmentation during early development (Dunwoodie et al., Development 129:1795-806 (2002)). Unlike the mammalian Notch family ligands DLL1, DLL4, JAG1, and JAG2 which all activate Notch receptor signaling in trans (Ntziachristos et al., Cancer Cell 25(3):318-34 (2014)), DLL3 is predominantly localized in the Golgi apparatus and is unable to activate Notch signaling (Chapman et al., Hum Mol Genet 20(5):905-16 (2011) and Geffers et al., J Cell Biol 178(3): 465-76 (2007)). During normal development, DLL3 inhibits both cis- and trans-acting Notch pathway activation by interacting with Notch and DLL1 (Chapman et al., Hum Mol Genet 20(5):905-16(2011)). DLL3 is normally either absent or present at very low levels in adult normal tissues except brain, but is overexpressed in lung cancer, testicular cancer, glioma and melanoma samples (Uhlen et al., Science 357 (6352): eaan2507 (2017)). Furthermore, DLL3 is detectable on the surface of small cell lung cancer (SCLC) and large cell neuroendocrine carcinoma (LCNEC) tumor cells (Saunders et al., Sci Transl Med 7(302):302ra136 (2015) and Sharma et al., Cancer Res 77(14):3931-41 (2017)), making it a potential target of monoclonal antibodies for cancer therapy. Therefore, an anti-DLL3 monoclonal antibody could be used to specifically target DLL3-expressing tumor cells and serve as a potential anti-cancer therapeutic.

BRIEF SUMMARY OF THE INVENTION

In one general aspect, the invention relates to isolated anti-DLL3 monoclonal antibodies or antigen-binding fragments thereof that bind DLL3.

Provided are isolated anti-DLL3 monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
(1) SEQ ID NOs: 25, 26, 27, 61, 62 and 63, respectively;
(2) SEQ ID NOs: 28, 29, 30, 64, 65 and 66, respectively;
(3) SEQ ID NOs: 31, 32, 33, 67, 68 and 69, respectively;
(4) SEQ ID NOs: 34, 35, 36, 70, 71 and 72, respectively;
(5) SEQ ID NOs: 37, 38, 39, 73, 74 and 75, respectively;
(6) SEQ ID NOs: 40, 41, 42, 76, 77 and 78, respectively;
(7) SEQ ID NOs: 43, 44, 45, 79, 80 and 81, respectively;
(8) SEQ ID NOs: 46, 47, 48, 82, 83 and 84, respectively;
(9) SEQ ID NOs: 49, 50, 51, 85, 86 and 87, respectively;
(10) SEQ ID NOs: 52, 53, 54, 88, 89 and 90, respectively;
(11) SEQ ID NOs: 55, 56, 57, 91, 92 and 93, respectively; or
(12) SEQ ID NOs: 58, 59, 60, 94, 95 and 96, respectively;
wherein the antibody or antigen-binding fragment thereof specifically binds DLL3, preferably human DLL3.

Provided are isolated anti-DLL3 monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
(1) SEQ ID NOs: 97, 98, 99, 133, 134 and 135, respectively;
(2) SEQ ID NOs: 100, 101, 102, 136, 137 and 138, respectively;
(3) SEQ ID NOs: 103, 104, 105, 139, 140 and 141, respectively;
(4) SEQ ID NOs: 106, 107, 108, 142, 143 and 144, respectively;
(5) SEQ ID NOs: 109, 110, 111, 145, 146 and 147, respectively;
(6) SEQ ID NOs: 112, 113, 114, 148, 149 and 150, respectively;
(7) SEQ ID NOs: 115, 116, 117, 151, 152 and 153, respectively;
(8) SEQ ID NOs: 118, 119, 120, 154, 155 and 156, respectively;
(9) SEQ ID NOs: 121, 122, 123, 157, 158 and 159, respectively;
(10) SEQ ID NOs: 124, 125, 126, 160, 161 and 162, respectively;
(11) SEQ ID NOs: 127, 128, 129, 163, 164 and 165, respectively; or
(12) SEQ ID NOs: 130, 131, 132, 166, 167 and 168, respectively;
wherein the antibody or antigen-binding fragment thereof specifically binds DLL3, preferably human DLL3.

In certain embodiments, the isolated anti-DLL3 monoclonal antibody or antigen-binding fragment thereof comprises a heavy chain variable region having a polypeptide sequence at least 95%, at least 96%, at least 97%, at least 98%, or at least 99% identical to SEQ ID NO:1, 3, 5, 7, 9, 11, 13, 15, 17, 19, 21 or 23, or a light chain variable region having a polypeptide sequence at least 95%, at least 96%, at least 97%, at least 98%, at least 99% identical to SEQ ID NO:2, 4, 6, 8, 10, 12, 14, 16, 18, 20, 22 or 24.

In certain embodiments, the isolated anti-DLL3 monoclonal antibody or antigen-binding fragment thereof comprises:
  (a) a heavy chain variable region having the polypeptide sequence of SEQ ID NO:1, and a light chain variable region having the polypeptide sequence of SEQ ID NO:2;
  (b) a heavy chain variable region having the polypeptide sequence of SEQ ID NO:3, and a light chain variable region having the polypeptide sequence of SEQ ID NO:4;
  (c) a heavy chain variable region having the polypeptide sequence of SEQ ID NO:5, and a light chain variable region having the polypeptide sequence of SEQ ID NO:6;
  (d) a heavy chain variable region having the polypeptide sequence of SEQ ID NO:7, and a light chain variable region having the polypeptide sequence of SEQ ID NO:8;
  (e) a heavy chain variable region having the polypeptide sequence of SEQ ID NO:9, and a light chain variable region having the polypeptide sequence of SEQ ID NO:10;
  (f) a heavy chain variable region having the polypeptide sequence of SEQ ID NO:11, and a light chain variable region having the polypeptide sequence of SEQ ID NO:12;
  (g) a heavy chain variable region having the polypeptide sequence of SEQ ID NO:13, and a light chain variable region having the polypeptide sequence of SEQ ID NO:14;
  (h) a heavy chain variable region having the polypeptide sequence of SEQ ID NO:15, and a light chain variable region having the polypeptide sequence of SEQ ID NO:16;
  (i) a heavy chain variable region having the polypeptide sequence of SEQ ID NO:17, and a light chain variable region having the polypeptide sequence of SEQ ID NO:18;
  (j) a heavy chain variable region having the polypeptide sequence of SEQ ID NO:19, and a light chain variable region having the polypeptide sequence of SEQ ID NO:20;
  (k) a heavy chain variable region having the polypeptide sequence of SEQ ID NO:21, and a light chain variable region having the polypeptide sequence of SEQ ID NO:22; or
  (l) a heavy chain variable region having the polypeptide sequence of SEQ ID NO:23, and a light chain variable region having the polypeptide sequence of SEQ ID NO:24.

In certain embodiments, the isolated anti-DLL3 monoclonal antibody or antigen-binding fragment thereof is chimeric.

In certain embodiments, the isolated anti-DLL3 monoclonal antibody or antigen-binding fragment thereof is human or humanized. In certain embodiments, the humanized monoclonal antibody or antigen-binding fragment thereof comprises:
  a. a heavy chain variable region having the polypeptide sequence of SEQ ID NO:170, and a light chain variable region having the polypeptide sequence of SEQ ID NO:171;
  b. a heavy chain variable region having the polypeptide sequence of SEQ ID NO:170, and a light chain variable region having the polypeptide sequence of SEQ ID NO:172; or
  c. a heavy chain variable region having the polypeptide sequence of SEQ ID NO:170, and a light chain variable region having the polypeptide sequence of SEQ ID NO:173.

In certain embodiments, the isolated anti-DLL3 monoclonal antibody or antigen-binding fragment thereof is capable of inducing effector-mediated tumor cell lysis through antibody-dependent cellular cytotoxicity (ADCC), antibody-dependent phagocytosis (ADPC) and complement-dependent cytotoxicity (CDC), and/or mediating the recruitment of conjugated drugs, and/or forming a bispecific antibody with another mAb or antigen-binding fragment with cancer-killing effect.

Also provided are isolated anti-CD47 monoclonal antibodies or antigen-binding fragments thereof comprising the humanized heavy chain variable region of an anti-CD47 monoclonal antibody and the humanized light chain variable region of an anti-DLL3 monoclonal antibody, wherein the anti-CD47 monoclonal antibody or antigen-binding fragment thereof comprises:
  a. a heavy chain variable region having the polypeptide sequence of SEQ ID NO:175, and a light chain variable region having the polypeptide sequence of SEQ ID NO:171;
  b. a heavy chain variable region having the polypeptide sequence of SEQ ID NO:175, and a light chain variable region having the polypeptide sequence of SEQ ID NO:172;
  c. a heavy chain variable region having the polypeptide sequence of SEQ ID NO:175, and a light chain variable region having the polypeptide sequence of SEQ ID NO:173;
  d. a heavy chain variable region having the polypeptide sequence of SEQ ID NO:176, and a light chain variable region having the polypeptide sequence of SEQ ID NO:171;
  e. a heavy chain variable region having the polypeptide sequence of SEQ ID NO:176, and a light chain variable region having the polypeptide sequence of SEQ ID NO:172;
  f. a heavy chain variable region having the polypeptide sequence of SEQ ID NO:176, and a light chain variable region having the polypeptide sequence of SEQ ID NO:173;
  g. a heavy chain variable region having the polypeptide sequence of SEQ ID NO:177, and a light chain variable region having the polypeptide sequence of SEQ ID NO:171;
  h. a heavy chain variable region having the polypeptide sequence of SEQ ID NO:177, and a light chain variable region having the polypeptide sequence of SEQ ID NO:172;
  i. a heavy chain variable region having the polypeptide sequence of SEQ ID NO:177, and a light chain variable region having the polypeptide sequence of SEQ ID NO:173; or
  j. a heavy chain variable region having the polypeptide sequence of SEQ ID NO:177, and a light chain variable region having the polypeptide sequence of SEQ ID NO:174.

In certain embodiments, the isolated anti-CD47 monoclonal antibody or antigen-binding fragment thereof is capable of blocking binding of CD47 to signal regulatory protein alpha (SIRPα).

In certain embodiments, the isolated anti-CD47 monoclonal antibody or antigen-binding fragment thereof is capable of inducing macrophage-mediated phagocytosis of cancer cells.

Provided are isolated humanized anti-CD47/DLL3 bispecific antibodies or antigen-binding fragments thereof comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 178, 179 and 180; the second antigen-binding domain comprises a heavy chain complementarity determining region 1 (HCDR1), HCDR2, HCDR3, having the polypeptide sequences of SEQ ID NOs: 181, 182 and 183; and the first antigen-binding domain and the second antigen-binding domain each comprises a light chain complementarity determining region 1 (LCDR1), LCDR2, and LCDR3, having the polypeptide sequences of SEQ ID NOs: 184, 185 and 186.

Provided are isolated humanized anti-CD47/DLL3 bispecific antibodies or antigen-binding fragments thereof comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 187, 188 and 189; the second antigen-binding domain comprises a heavy chain complementarity determining region 1 (HCDR1), HCDR2, HCDR3, having the polypeptide sequences of SEQ ID NOs: 190, 191 and 192; and the first antigen-binding domain and the second antigen-binding domain each comprises a light chain complementarity determining region 1 (LCDR1), LCDR2, and LCDR3, having the polypeptide sequences of SEQ ID NOs: 193, 194 and 195.

In certain embodiments, the isolated humanized anti-CD47/DLL3 bispecific antibodies or antigen-binding fragments thereof comprise a first antigen-binding domain that specifically binds CD47, preferably human CD47, and a second antigen-binding domain that specifically binds DLL3, preferably human DLL3, wherein the first antigen-binding domain comprises a heavy chain variable region having a polypeptide sequence at least 95%, at least 96%, at least 97%, at least 98%, or at least 99% identical to SEQ ID NO:176, and a light chain variable region having a polypeptide sequence at least 95%, at least 96%, at least 97%, at least 98%, or at least 99% identical to SEQ ID NO:172; and wherein the second antigen-binding domain comprises a heavy chain variable region having a polypeptide sequence at least 95%, at least 96%, at least 97%, at least 98%, or at least 99% identical to SEQ ID NO:170, and a light chain variable region having the a polypeptide sequence at least 95%, at least 96%, at least 97%, at least 98%, or at least 99% identical to SEQ ID NO:172.

In certain embodiments, the isolated humanized anti-CD47/DLL3 bispecific antibody or antigen-binding fragment thereof is capable of blocking binding of CD47 to signal regulatory protein alpha (SIRPα) on cancer cells that express both DLL3 and CD47.

In certain embodiments, the isolated humanized anti-CD47/DLL3 bispecific antibody or antigen-binding fragment thereof is capable of inducing macrophage-mediated phagocytosis of cancer cells that express both DLL3 and CD47.

In certain embodiments, the isolated humanized anti-CD47/DLL3 bispecific antibody or antigen-binding fragment thereof is capable of binding cancer cells that express both DLL3 and CD47 with minimal to undetectable binding to human red blood cells (RBCs).

Also provided are isolated nucleic acids encoding the anti-DLL3 monoclonal antibodies or antigen-binding fragments thereof, the anti-CD47 monoclonal antibodies or antigen-binding fragments thereof, or the humanized anti-CD47/DLL3 bispecific antibodies or antigen-binding fragments thereof of the invention disclosed herein.

Also provided are vectors comprising the isolated nucleic acids encoding the anti-DLL3 monoclonal antibodies or antigen-binding fragments thereof, the anti-CD47 monoclonal antibodies or antigen-binding fragments thereof, or the humanized anti-CD47/DLL3 bispecific antibodies or antigen-binding fragments thereof of the invention.

Also provided are host cells comprising the vectors comprising the isolated nucleic acids encoding the anti-DLL3 monoclonal antibodies or antigen-binding fragments thereof, the anti-CD47 monoclonal antibodies or antigen-binding fragments thereof, or the humanized anti-CD47/DLL3 bispecific antibodies or antigen-binding fragments thereof of the invention.

In certain embodiments, provided is a pharmaceutical composition comprising the isolated anti-DLL3 monoclonal antibodies or antigen-binding fragments thereof, the isolated anti-CD47 monoclonal antibodies or antigen-binding fragments thereof, or the isolated humanized anti-CD47/DLL3 bispecific antibodies or antigen-binding fragments thereof of the invention and a pharmaceutically acceptable carrier.

Also provided are methods of targeting DLL3 on a cancer cell surface in a subject in need thereof, comprising administering to the subject the pharmaceutical compositions comprising the isolated anti-DLL3 monoclonal antibodies or antigen-binding fragments thereof of the invention.

Also provided are methods of blocking binding of CD47 to signal regulatory protein alpha (SIRPα) in a subject in need thereof, comprising administering to the subject the pharmaceutical compositions comprising the isolated anti-CD47 monoclonal antibodies or antigen-binding fragments thereof of the invention.

Also provided are methods of inducing macrophage-mediated phagocytosis of cancer cells in a subject in need thereof, comprising administering to the subject the pharmaceutical compositions comprising the isolated anti-CD47 monoclonal antibodies or antigen-binding fragments thereof of the invention.

Also provided are methods of targeting DLL3 and CD47 that are both expressed on a cancer cell surface in a subject in need thereof, comprising administering to the subject the pharmaceutical compositions comprising the isolated humanized anti-CD47/DLL3 bispecific antibodies or antigen-binding fragments thereof of the invention.

Also provided are methods of blocking binding of CD47 to SIRPα on cancer cells that express both DLL3 and CD47 in a subject in need thereof, comprising administering to the subject the pharmaceutical compositions comprising the isolated humanized anti-CD47/DLL3 bispecific antibodies or antigen-binding fragments thereof of the invention.

Also provided are methods of inducing macrophage-mediated phagocytosis of cancer cells that express both DLL3 and CD47 in a subject in need thereof, comprising administering to the subject the pharmaceutical compositions comprising the isolated humanized anti-CD47/DLL3 bispecific antibodies or antigen-binding fragments thereof of the invention.

Also provided are methods of binding cancer cells that express both DLL3 and CD47 by a humanized anti-CD47/DLL3 bispecific antibody or antigen-binding fragment with minimal to undetectable binding to human red blood cells (RBCs) in a subject in need thereof, comprising administering to the subject the pharmaceutical compositions comprising the isolated humanized anti-CD47/DLL3 bispecific antibodies or antigen-binding fragments thereof of the invention.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, such as small cell lung cancer (SCLC), large cell neuroendocrine carcinoma (LCNEC), a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of producing the isolated anti-DLL3 monoclonal antibody or antigen-binding fragment thereof, the isolated anti-CD47 monoclonal antibody or antigen-binding fragment thereof, or the isolated humanized anti-CD47/DLL3 bispecific antibody or antigen-binding fragment thereof of the invention, comprising culturing a cell comprising a nucleic acid encoding the antibody or antigen-binding fragment thereof under conditions to produce the antibody or antigen-binding fragment thereof, and recovering the antibody or antigen-binding fragment thereof from the cell or culture.

Also provided are methods of producing a pharmaceutical composition comprising the isolated anti-DLL3 monoclonal antibody or antigen-binding fragment thereof, the isolated anti-CD47 monoclonal antibody or antigen-binding fragment thereof, or the isolated humanized anti-CD47/DLL3 bispecific antibody or antigen-binding fragment thereof of the invention, comprising combining the antibody or antigen-binding fragment thereof with a pharmaceutically acceptable carrier to obtain the pharmaceutical composition.

Also provided are methods of determining a level of DLL3 in a subject. The methods comprise (a) obtaining a sample from the subject; (b) contacting the sample with an isolated anti-DLL3 monoclonal antibody or antigen-binding fragment thereof of the invention; and (c) determining the level of DLL3 in the subject. In certain embodiments, the sample is a tissue sample. The tissue sample can, for example, be a cancer tissue sample. In certain embodiments, the sample is a blood sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1A:
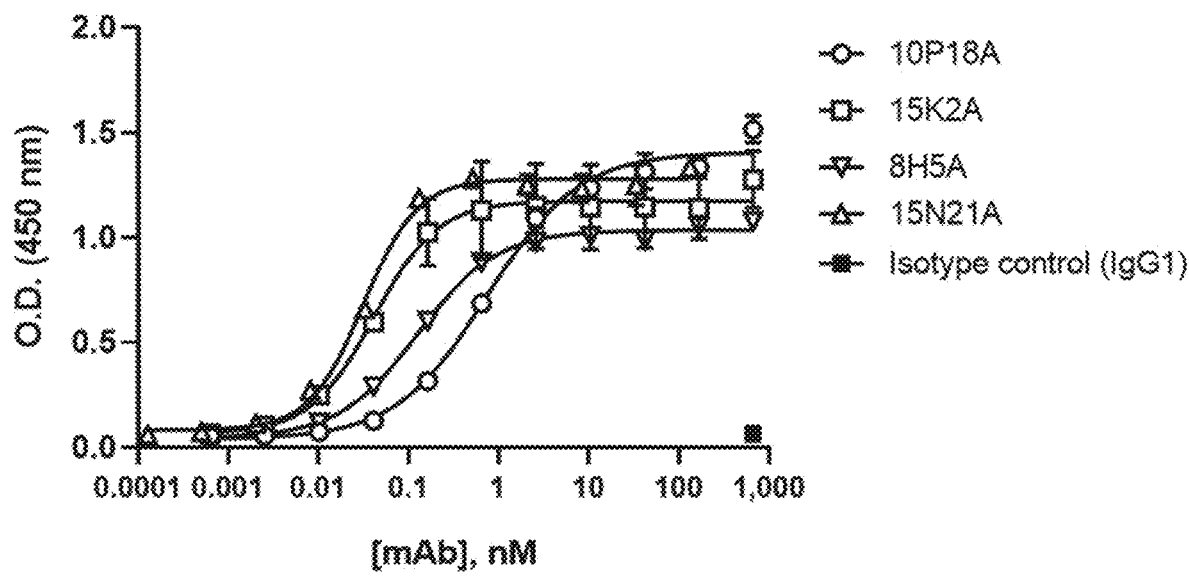
FIGS. 1A-1C show the binding of purified anti-DLL3 chimeric mAbs to coated recombinant DLL3 protein by ELISA.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-DLL3 antibodies, anti-CD47 antibodies, anti-CD47/DLL3 bi-specific antibodies, DLL3 polypeptides, and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

The invention generally relates to isolated anti-DLL3 antibodies, anti-CD47 antibodies, anti-CD47/DLL3 bispecific antibodies, nucleic acids and expression vectors encoding the antibodies, recombinant cells containing the vectors, and compositions comprising the antibodies. Methods of making the antibodies, and methods of using the antibodies to treat diseases, including cancer, are also provided. The antibodies of the invention possess one or more desirable functional properties, including but not limited to high-affinity binding to DLL3 and/or CD47, high specificity to DLL3 and/or CD47, the ability to induce effector-mediated tumor cell lysis, the ability to stimulate complement-dependent cytotoxicity (CDC), antibody-dependent phagocytosis (ADPC), and/or antibody-dependent cellular-mediated cytotoxicity (ADCC) against cells expressing DLL3 and/or CD47, the ability to mediate the recruitment of conjugated drugs, the ability to form a bispecific antibody with another mAb or antigen-binding fragment with cancer-killing effect, and the ability to inhibit tumor growth in subjects and animal models when administered alone or in combination with other anti-cancer therapies.

In a general aspect, the invention relates to isolated anti-DLL3 monoclonal antibodies or antigen-binding fragments thereof that bind DLL3.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to DLL3 is substantially free of antibodies that do not bind to DLL3, an isolated antibody that specifically binds to CD47 is substantially free of antibodies that do not bind to CD47, a bispecific antibody that specifically binds to CD47 and DLL3 is substantially free of antibodies that do not bind to CD47 and DLL3). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on DLL3 and the second epitope is located on PD-1, PD-L1, TIM-3, LAG-3, CD73, apelin, CTLA-4, EGFR, HER-2, CD3, CD19, CD20, CD33, CD47, TIP-1, CLDN18.2, FOLR1, and/or other tumor associated immune suppressors or surface antigens.

As used herein, the term "DLL3" refers to Delta like canonical Notch ligand 3 (DLL3), also known as delta like 3 or delta like protein 3, is required for somite segmentation during early development (Dunwoodie et al., Development 129:1795-806 (2002)). Unlike the mammalian Notch family ligands DLL1, DLL4, JAG1, and JAG2, which all activate Notch receptor signaling in trans (Ntziachristos et al., Cancer Cell 25(3):318-34 (2014)), DLL3 is predominantly localized in the Golgi apparatus and is unable to activate Notch signaling (Chapman et al., Hum Mol Genet 2011; 20(5):905-16 and Geffers et al., J Cell Biol 178(3):465-76 (2007)). During normal development, DLL3 inhibits both cis- and trans-acting Notch pathway activation by interacting with Notch and DLL1 (Chapman et al., Hum Mol Genet 20(5):905-16 (2011)). DLL3 is normally either absent or present at very low levels in adult normal tissues except brain, but is overexpressed in lung cancer, testicular cancer, glioma and melanoma samples (Uhlen et al., Science 357 (6352):eaan2507 (2017)). Further, DLL3 is detectable on the surface of small cell lung cancer (SCLC) and large cell neuroendocrine carcinoma (LCNEC) tumor cells (Saunders et al., Sci Transl Med 7(302):302ra136 (2015) and Sharma et al., Cancer Res 77(14):3931-3941 (2017)), making it a potential target of monoclonal antibodies for cancer therapy. The term "human DLL3" refers to a DLL3 originated from a human. An exemplary amino acid sequence of a human DLL3 is represented in GenBank Accession No. NP_058637.1 (SEQ ID NO:169).

As used herein, the term "CD47" refers to a multispanning transmembrane receptor belonging to the immunoglobulin superfamily, which has been indicated to be involved in multiple cellular process, including cell migration, adhesion, and T cell function. CD47, also known as integrin-associated protein (IAP), ovarian cancer antigen (OA3), Rh-related antigen, and MERG, was originally identified as a tumor antigen on human ovarian cancer and was subsequently shown to be expressed on multiple human tumor types, including both hematologic and solid tumors. The interaction between CD47 and signal regulatory protein alpha (SIRPα), an inhibitory protein expressed on macrophages, prevents phagocytosis of CD47-expressing cells. CD47 is additionally expressed at low levels on virtually all non-malignant cells. The term "human CD47" refers to a CD47 originated from a human. An exemplary amino acid sequence of a human CD47 is represented in GenBank Accession No. NP_001768.1.

As used herein, an antibody that "specifically binds to DLL3," "specifically binds to CD47," or an antibody that "specifically binds to CD47 and DLL3" refers to an antibody that binds to a DLL3, preferably a human DLL3; binds to CD47, preferably a human CD47; or DLL3 and CD47, preferably human DLL3 and human CD47, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated anti-DLL3 monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:25, 26, 27, 61, 62 and 63, respectively;
(2) SEQ ID NOs:28, 29, 30, 64, 65 and 66, respectively;
(3) SEQ ID NOs:31, 32, 33, 67, 68 and 69, respectively;
(4) SEQ ID NOs:34, 35, 36, 70, 71 and 72, respectively;
(5) SEQ ID NOs:37, 38, 39, 73, 74 and 75, respectively;
(6) SEQ ID NOs:40, 41, 42, 76, 77 and 78, respectively;
(7) SEQ ID NOs:43, 44, 45, 79, 80 and 81, respectively;
(8) SEQ ID NOs:46, 47, 48, 82, 83 and 84, respectively;
(9) SEQ ID NOs:49, 50, 51, 85, 86 and 87, respectively;
(10) SEQ ID NOs:52, 53, 54, 88, 89 and 90, respectively;
(11) SEQ ID NOs:55, 56, 57, 91, 92 and 93, respectively; or
(12) SEQ ID NOs:58, 59, 60, 94, 95 and 96, respectively;

wherein the antibody or antigen-binding fragment thereof specifically binds DLL3, preferably human DLL3.

According to a particular aspect, the invention relates to an isolated anti-DLL3 monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:97, 98, 99, 133, 134 and 135, respectively;
(2) SEQ ID NOs:100, 101, 102, 136, 137 and 138, respectively;
(3) SEQ ID NOs:103, 104, 105, 139, 140 and 141, respectively;
(4) SEQ ID NOs:106, 107, 108, 142, 143 and 144, respectively;
(5) SEQ ID NOs:109, 110, 111, 145, 146 and 147, respectively;
(6) SEQ ID NOs:112, 113, 114, 148, 149 and 150, respectively;
(7) SEQ ID NOs:115, 116, 117, 151, 152 and 153, respectively;
(8) SEQ ID NOs:118, 119, 120, 154, 155 and 156, respectively;
(9) SEQ ID NOs:121, 122, 123, 157, 158 and 159, respectively;
(10) SEQ ID NOs:124, 125, 126, 160, 161 and 162, respectively;
(11) SEQ ID NOs:127, 128, 129, 163, 164 and 165, respectively; or
(12) SEQ ID NOs:130, 131, 132, 166, 167 and 168, respectively;

wherein the antibody or antigen-binding fragment thereof specifically binds DLL3, preferably human DLL3.

According to another particular aspect, the invention relates to an isolated anti-DLL3 monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NOs:1, 3, 5, 7, 9, 11, 13, 15, 17, 19, 21 or 23, or a light chain variable region having a polypeptide sequence at least 85%, preferably 90%, more preferably 95% or more, such as 95%, 96%, 97%, 98%, or 99% identical to one of SEQ ID NOs:2, 4, 6, 8, 10, 12, 14, 16, 18, 20, 22 or 24. According to one preferred embodiment, the isolated anti-DLL3 monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO:1, 3, 5, 7, 9, 11, 13, 15, 17, 19, 21 or 23, and a light chain variable region having a polypeptide sequence at least 85%, preferably 90%, more preferably 95% or more, such as 95%, 96%, 97%, 98%, or 99% identical to SEQ ID NO:2, 4, 6, 8, 10, 12, 14, 16, 18, 20, 22 or 24, respectively.

According to another particular aspect, the invention relates to an isolated anti-DLL3 monoclonal antibody or antigen-binding fragment thereof of the invention, comprising:

a. a heavy chain variable region having the polypeptide sequence of SEQ ID NO:1, and a light chain variable region having the polypeptide sequence of SEQ ID NO:2;
b. a heavy chain variable region having the polypeptide sequence of SEQ ID NO:3, and a light chain variable region having the polypeptide sequence of SEQ ID NO:4;
c. a heavy chain variable region having the polypeptide sequence of SEQ ID NO:5, and a light chain variable region having the polypeptide sequence of SEQ ID NO:6;
d. a heavy chain variable region having the polypeptide sequence of SEQ ID NO:7, and a light chain variable region having the polypeptide sequence of SEQ ID NO:8;
e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16;
i. a heavy chain variable region having the polypeptide sequence of SEQ ID NO:17, and a light chain variable region having the polypeptide sequence of SEQ ID NO:18;
j. a heavy chain variable region having the polypeptide sequence of SEQ ID NO:19, and a light chain variable region having the polypeptide sequence of SEQ ID NO:20;

k. a heavy chain variable region having the polypeptide sequence of SEQ ID NO:21, and a light chain variable region having the polypeptide sequence of SEQ ID NO:22; or l. a heavy chain variable region having the polypeptide sequence of SEQ ID NO:23, and a light chain variable region having the polypeptide sequence of SEQ ID NO:24.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 25, 26, 27, 61, 62 and 63, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated anti-DLL3 monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 28, 29, 30, 64, 65 and 66, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated anti-DLL3 monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 31, 32, 33, 67, 68 and 69, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated anti-DLL3 monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 34, 35, 36, 70, 71 and 72, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated anti-DLL3 monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 37, 38, 39, 73, 74 and 75, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated anti-DLL3 monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 40, 41, 42, 76, 77 and 78, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated anti-DLL3 monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 43, 44, 45, 79, 80 and 81, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated anti-DLL3 monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 46, 47, 48, 82, 83 and 84, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated anti-DLL3 monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 49, 50, 51, 85, 86 and 87, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated anti-DLL3 monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 52, 53, 54, 88, 89 and 90, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated anti-DLL3 monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 55, 56, 57, 91, 92 and 93, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22. Preferably, the isolated anti-DLL3 monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 58, 59, 60, 94, 95 and 96, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:23, and a light chain variable region having a polypeptide sequence at least 85%, preferably 90%, more preferably 95% or more, such as 95%, 96%, 97%, 98%, or 99% identical to SEQ ID NO:24. Preferably, the isolated anti-DLL3 monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 97, 98, 99, 133, 134 and 135, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated anti-DLL3 monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 100, 101, 102, 136, 137 and 138, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated anti-DLL3 monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 103, 104, 105, 139, 140 and 141, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated anti-DLL3 monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 106, 107, 108, 142, 143 and 144, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated anti-DLL3 monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 109, 110, 111, 145, 146 and 147, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated anti-DLL3 monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 112, 113, 114, 148, 149 and 150, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated anti-DLL3 monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 115, 116, 117, 151, 152 and 153, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated anti-DLL3 monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 118, 119, 120, 154, 155 and 156, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated anti-DLL3 monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 121, 122, 123, 157, 158 and 159, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated anti-DLL3 monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 124, 125, 126, 160, 161 and 162, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated anti-DLL3 monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 127, 128, 129, 163, 164 and 165, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22. Preferably, the isolated anti-DLL3 monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated anti-DLL3 monoclonal antibody or antigen-binding fragment thereof, comprising HCDR1, HCDR2, HCDR3, LCDR1, LCDR2 and LCDR3, having the polypeptide sequences of SEQ ID NOs: 130, 131, 132, 166, 167 and 168, respectively. In another embodiment, the isolated anti-DLL3 monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:23, and a light chain variable region having a polypeptide sequence at least 85%, preferably 90%, more preferably 95% or more, such as 95%, 96%, 97%, 98%, or 99% identical to SEQ ID NO:24. Preferably, the isolated anti-DLL3 monoclonal antibody or antigen-binding fragment thereof comprises a heavy chain variable region having the polypeptide sequence of SEQ ID NO:23; and a light chain variable region having the polypeptide sequence of SEQ ID NO:24.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized anti-DLL3 monoclonal antibody or antigen-binding fragment thereof, wherein the isolated humanized antibody or antigen-binding fragment thereof comprises:
 a. a heavy chain variable region having the polypeptide sequence of SEQ ID NO:170, and a light chain variable region having the polypeptide sequence of SEQ ID NO:171;
 b. a heavy chain variable region having the polypeptide sequence of SEQ ID NO:170, and a light chain variable region having the polypeptide sequence of SEQ ID NO:172; or
 c. a heavy chain variable region having the polypeptide sequence of SEQ ID NO:170, and a light chain variable region having the polypeptide sequence of SEQ ID NO:173.

According to another particular aspect, the isolated anti-DLL3 monoclonal antibody or antigen-binding fragment thereof is capable of inducing effector-mediated tumor cell lysis through antibody-dependent cellular cytotoxicity (ADCC), antibody-dependent phagocytosis (ADPC) and complement-dependent cytotoxicity (CDC), and/or mediating the recruitment of conjugated drugs, and/or forming a bispecific antibody with another mAb or antigen-binding fragment with cancer-killing effect.

According to another particular aspect, the invention relates to an isolated anti-CD47 monoclonal antibody or antigen-binding fragment comprising the humanized heavy chain variable region of an anti-CD47 monoclonal antibody and the humanized light chain variable region of an anti-DLL3 monoclonal antibody, wherein the anti-CD47 monoclonal antibody or antigen-binding fragment thereof comprises:
 a. a heavy chain variable region having the polypeptide sequence of SEQ ID NO:175, and a light chain variable region having the polypeptide sequence of SEQ ID NO:171;
 b. a heavy chain variable region having the polypeptide sequence of SEQ ID NO:175, and a light chain variable region having the polypeptide sequence of SEQ ID NO:172;
 c. a heavy chain variable region having the polypeptide sequence of SEQ ID NO:175, and a light chain variable region having the polypeptide sequence of SEQ ID NO:173;
 d. a heavy chain variable region having the polypeptide sequence of SEQ ID NO:176, and a light chain variable region having the polypeptide sequence of SEQ ID NO:171;
 e. a heavy chain variable region having the polypeptide sequence of SEQ ID NO:176, and a light chain variable region having the polypeptide sequence of SEQ ID NO:172;
 f. a heavy chain variable region having the polypeptide sequence of SEQ ID NO:176, and a light chain variable region having the polypeptide sequence of SEQ ID NO:173;
 g. a heavy chain variable region having the polypeptide sequence of SEQ ID NO:177, and a light chain variable region having the polypeptide sequence of SEQ ID NO:171;

h. a heavy chain variable region having the polypeptide sequence of SEQ ID NO:177, and a light chain variable region having the polypeptide sequence of SEQ ID NO:172;

i. a heavy chain variable region having the polypeptide sequence of SEQ ID NO:177, and a light chain variable region having the polypeptide sequence of SEQ ID NO:173; or j. a heavy chain variable region having the polypeptide sequence of SEQ ID NO:177, and a light chain variable region having the polypeptide sequence of SEQ ID NO:174.

According to another particular aspect, the isolated anti-CD47 monoclonal antibody or antigen-binding fragment thereof is capable of blocking binding of CD47 to signal regulatory protein alpha (SIRPα).

According to another particular aspect, the isolated anti-CD47 monoclonal antibody or antigen-binding fragment thereof is capable of inducing macrophage-mediated phagocytosis of cancer cells.

According to another particular aspect, the invention relates to an isolated humanized anti-CD47/DLL3 bispecific antibody or antigen-binding fragment comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 178, 179 and 180; the second antigen-binding domain comprises a heavy chain complementarity determining region 1 (HCDR1), HCDR2, HCDR3, having the polypeptide sequences of SEQ ID NOs: 181, 182 and 183; and the first antigen-binding domain and the second antigen-binding domain each comprises a light chain complementarity determining region 1 (LCDR1), LCDR2, and LCDR3, having the polypeptide sequences of SEQ ID NOs: 184, 185 and 186.

According to another particular aspect, the invention relates to an isolated humanized anti-CD47/DLL3 bispecific antibody or antigen-binding fragment comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 187, 188 and 189; the second antigen-binding domain comprises a heavy chain complementarity determining region 1 (HCDR1), HCDR2, HCDR3, having the polypeptide sequences of SEQ ID NOs: 190, 191 and 192; and the first antigen-binding domain and the second antigen-binding domain each comprises a light chain complementarity determining region 1 (LCDR1), LCDR2, and LCDR3, having the polypeptide sequences of SEQ ID NOs: 193, 194 and 195.

According to another particular aspect, the invention relates to an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, wherein the first antigen-binding domain comprises a heavy chain variable region having a polypeptide sequence at least 85%, preferably 90%, more preferably 95% or more, such as 95%, 96%, 97%, 98%, or 99% identical to SEQ ID NO:176, and a light chain variable region having a polypeptide sequence at least 85%, preferably 90%, more preferably 95% or more, such as 95%, 96%, 97%, 98%, or 99% identical to SEQ ID NO:172; and wherein the second antigen-binding domain comprises a heavy chain variable region having a polypeptide sequence at least 85%, preferably 90%, more preferably 95% or more, such as 95%, 96%, 97%, 98%, or 99% identical to SEQ ID NO:170, and a light chain variable region having a polypeptide sequence at least 85%, preferably 90%, more preferably 95% or more, such as 95%, 96%, 97%, 98%, or 99% identical to SEQ ID NO:172.

According to another particular aspect, the invention relates to an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, wherein the humanized anti-CD47/DLL3 bispecific antibody or antigen-binding fragment thereof is capable of blocking binding of CD47 to SIRPα on cancer cells that express both DLL3 and CD47.

According to another particular aspect, the invention relates to an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, wherein the humanized anti-CD47/DLL3 bispecific antibody or antigen-binding fragment thereof is capable of inducing macrophage-mediated phagocytosis of cancer cells that express both DLL3 and CD47.

According to another particular aspect, the invention relates to an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, wherein the humanized anti-CD47/DLL3 bispecific antibody or antigen-binding fragment thereof is capable of binding cancer cells that express both DLL3 and CD47 with minimal to undetectable binding to human red blood cells (RBCs).

In another general aspect, the invention relates to an isolated nucleic acid encoding an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding antibodies or antigen-binding fragments thereof of the invention can be altered without changing the amino acid sequences of the proteins.

In another general aspect, the invention relates to a vector comprising an isolated nucleic acid encoding an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention. Such techniques are well known to those skilled in the art in view of the present disclosure.

In another general aspect, the invention relates to a host cell comprising an isolated nucleic acid encoding an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention. Any host cell known to those skilled in the art in view of the present disclosure can be used for recombinant expression of antibodies or antigen-binding fragments thereof of the invention. In some embodiments, the host cells are E. coli TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention, comprising culturing a cell comprising a nucleic acid encoding the antibody or antigen-binding fragment thereof under conditions to produce an antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated anti-DLL3 monoclonal antibody or antigen-binding fragment thereof, an isolated anti-CD47 monoclonal antibody or antigen-binding fragment thereof, or an isolated humanized anti-CD47/DLL3 bispecific antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention, comprising combining an antibody or antigen-binding fragment thereof with a pharmaceutically acceptable carrier to obtain the pharmaceutical composition.

Methods of Use

In another general aspect, the invention relates to a method of targeting DLL3 on a cancer cell surface in a subject in need thereof, the method comprises administering to the subject in need thereof an isolated anti-DLL3 monoclonal antibody or antigen binding fragment thereof that specifically binds DLL3 or a pharmaceutical composition of the invention. Binding of the monoclonal antibody or antigen-binding fragment thereof to DLL3 can mediate complement-dependent cytotoxicity (CDC), antibody-dependent phagocytosis (ADPC), and/or antibody-dependent cellular cytotoxicity (ADCC) or other effects that result in the death of the targeted cancer cell. The monoclonal antibody or antigen-binding fragment thereof can, for example, serve to recruit conjugated drugs, and/or can form a bispecific antibody with another monoclonal antibody or antigen-binding fragment thereof to mediate the death of the targeted cancer cell.

In another general aspect, the invention relates to a method of blocking binding of CD47 to signal regulatory protein alpha (SIRPα) in a subject in need thereof, the method comprises administering to the subject in need thereof an anti-CD47 monoclonal antibody or antigen-binding fragment thereof or a pharmaceutical composition of the invention.

In another general aspect, the invention relates to a method of inducing macrophage-mediated phagocytosis of cancer cells in a subject in need thereof, the method comprises administering to the subject in need thereof an anti-CD47 monoclonal antibody or antigen-binding fragment thereof or a pharmaceutical composition of the invention.

In another general aspect, the invention relates to a method of targeting DLL3 and CD47 on a cancer cell surface in a subject in need thereof, the method comprises administering to the subject in need thereof a humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, or a pharmaceutical composition of the invention.

In another general aspect, the invention relates to a method of blocking binding of CD47 to signal regulatory protein alpha (SIRPα) on cancer cells that express both DLL3 and CD47 in a subject in need thereof, the method comprises administering to the subject in need thereof an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, or a pharmaceutical composition of the invention. Binding of the humanized anti-CD47/DLL3 bispecific antibody or antigen-binding fragment thereof to the cancer cells can mediate blocking the binding of CD47 to SIRPα.

In another general aspect, the invention relates to a method of inducing macrophage-mediated phagocytosis of cancer cells that express both DLL3 and CD47 in a subject in need thereof, the method comprises administering to the subject in need thereof an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, or a pharmaceutical composition of the invention. Binding of the humanized anti-CD47/DLL3 bispecific antibody or antigen-binding fragment to the cancer cells can induce macrophage-mediated phagocytosis of the cancer cells.

In another general aspect, the invention relates to a method of binding cancer cells that express both DLL3 and CD47 with minimal to undetectable binding to human red blood cells (RBCs) in a subject in need thereof, the method comprises administering to the subject in need thereof an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, or a pharmaceutical composition of the invention. The humanized anti-CD47/DLL3 bispecific antibody or antigen-binding fragment thereof of the invention has high selectivity for cancer cells with minimal to undetectable binding to human red blood cells (RBCs).

The functional activity of antibodies and antigen-binding fragments thereof that bind DLL3 or CD47, or bispecific antibodies and antigen binding fragments thereof that bind DLL3 and CD47 can be characterized by methods known in the art and as described herein. Methods for characterizing antibodies and antigen-binding fragments thereof that bind DLL3 or CD47, or bispecific antibodies and antigen binding fragments thereof that bind DLL3 and CD47 include, but are not limited to, affinity and specificity assays including Biacore, ELISA, FACS and OctetRed analysis. According to particular embodiments, the methods for characterizing antibodies and antigen-binding fragments thereof that bind DLL3 or CD47, or bispecific antibodies and antigen binding fragments thereof that bind DLL3 and CD47 include those described below.

In another general aspect, the invention relates to a method of treating a cancer in a subject in need thereof, comprising administering to the subject in need thereof an isolated anti-DLL3 monoclonal antibody or antigen binding fragment thereof, an isolated anti-CD47 monoclonal antibody or antigen-binding fragment thereof, or an isolated humanized anti-CD47/DLL3 bispecific antibody or antigen-binding fragment thereof or a pharmaceutical composition of the invention. The cancer can, for example, be selected from but not limited to, a lung cancer, such as small cell lung cancer (SCLC), large cell neuroendocrine carcinoma (LCNEC), a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

According to embodiments of the invention, the pharmaceutical composition comprises a therapeutically effective amount of an anti-DLL3 monoclonal antibody or antigen-binding fragment thereof, an anti-CD47 monoclonal antibody or antigen-binding fragment thereof, or a humanized anti-CD47/DLL3 bispecific antibody or antigen-binding fragment thereof of the invention. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-DLL3 antibodies or antigen-binding fragments thereof, anti-CD47 antibodies or antigen-binding fragments thereof, or anti-CD47/DLL3 bispecific antibodies or antigen-binding fragments thereof, a therapeutically effective amount means an amount of the anti-DLL3 antibody or antigen-binding fragment thereof, anti-CD47 antibody or antigen-binding fragment thereof, or anti-CD47/DLL3 bispecific antibody or antigen-binding fragment thereof that modulates an immune response in a subject in need thereof. Also as used herein with reference to anti-DLL3 antibodies or antigen-binding fragments thereof, anti-CD47 antibody or antigen-binding fragment thereof, or anti-CD47/DLL3 bispecific antibodies or antigen-binding fragments thereof, a therapeutically effective amount means an amount of the anti-DLL3 antibody or antigen-binding fragment thereof, anti-CD47 antibody or antigen-binding fragment thereof, or anti-CD47/DLL3 bispecific antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, such as small cell lung cancer (SCLC), large cell neuroendocrine carcinoma (LCNEC), a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer. For cancer therapy, it can be used in combination with another treatment including, but not limited to, a chemotherapy, an anti-TIM-3 mAb, an anti-LAG-3 mAb, an anti-CD73 mAb, an anti-apelin mAb, an anti-CTLA-4 antibody, an anti-EGFR mAb, an anti-HER-2 mAb, an anti-CD19 mAb, an anti-CD20 mAb, an anti-CD33 mAb, an anti-CD47 mAb, an anti-TIP-1 mAb, an anti-CLDN18.2 mAb, an anti-FOLR1 mAb, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of DLL3 in a subject. The methods comprise (a) obtaining a sample from the subject; (b) contacting the sample with an anti-DLL3 monoclonal antibody or antigen-binding fragment thereof of the invention; and (c) determining a level of DLL3 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of DLL3 in the subject can be determined utilizing assays selected from, but not limited to, a Western blot assay, an ELISA assay, and/or an immunohistochemistry (IHC) assay. Relative protein levels can be determined by utilizing Western blot analysis and IHC, and absolute protein levels can be determined by utilizing an ELISA assay. When determining the relative levels of DLL3, the levels of DLL3 can be determined between at least two samples, e.g., between samples from the same subject at different time points, between samples from different tissues in the same subject, and/or between samples from different subjects. Alternatively, when determining absolute levels of DLL3, such as by an ELISA assay, the absolute level of DLL3 in the sample can be determined by creating a standard for the ELISA assay prior to testing the sample. A person skilled in the art would understand which analytical techniques to utilize to determine the level of DLL3 in a sample from the subject utilizing the antibodies or antigen-binding fragments thereof of the invention.

Utilizing methods of determining a level of DLL3 in a sample from a subject can lead to the diagnosis of abnormal (elevated, reduced, or insufficient) DLL3 levels in a disease and making appropriate therapeutic decisions. Such a disease can be, but not limited to, a cancer. Additionally, by monitoring the levels of DLL3 in a subject, the risk of developing a disease as indicated above can be determined based on the knowledge of the level of DLL3 in a particular disease and/or during the progression of the particular disease.

EMBODIMENTS

The invention provides also the following non-limiting embodiments.

Embodiment 1 is an isolated anti-DLL3 monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
- (1) SEQ ID NOs:25, 26, 27, 61, 62 and 63, respectively;
- (2) SEQ ID NOs:28, 29, 30, 64, 65 and 66, respectively;
- (3) SEQ ID NOs:31, 32, 33, 67, 68 and 69, respectively;
- (4) SEQ ID NOs:34, 35, 36, 70, 71 and 72, respectively;
- (5) SEQ ID NOs:37, 38, 39, 73, 74 and 75, respectively;
- (6) SEQ ID NOs:40, 41, 42, 76, 77 and 78, respectively;
- (7) SEQ ID NOs:43, 44, 45, 79, 80 and 81, respectively;
- (8) SEQ ID NOs:46, 47, 48, 82, 83 and 84, respectively;
- (9) SEQ ID NOs:49, 50, 51, 85, 86 and 87, respectively;
- (10) SEQ ID NOs:52, 53, 54, 88, 89 and 90, respectively;
- (11) SEQ ID NOs:55, 56, 57, 91, 92 and 93, respectively; or
- (12) SEQ ID NOs:58, 59, 60, 94, 95 and 96, respectively;

wherein the antibody or antigen-binding fragment thereof specifically binds DLL3, preferably specifically binds human DLL3.

Embodiment 2 is an isolated anti-DLL3 monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
- (1) SEQ ID NOs:97, 98, 99, 133, 134 and 135, respectively;
- (2) SEQ ID NOs:100, 101, 102, 136, 137 and 138, respectively;
- (3) SEQ ID NOs:103, 104, 105, 139, 140 and 141, respectively;
- (4) SEQ ID NOs:106, 107, 108, 142, 143 and 144, respectively;
- (5) SEQ ID NOs:109, 110, 111, 145, 146 and 147, respectively;
- (6) SEQ ID NOs:112, 113, 114, 148, 149 and 150, respectively;
- (7) SEQ ID NOs:115, 116, 117, 151, 152 and 153, respectively;
- (8) SEQ ID NOs:118, 119, 120, 154, 155 and 156, respectively;
- (9) SEQ ID NOs:121, 122, 123, 157, 158 and 159, respectively;
- (10) SEQ ID NOs:124, 125, 126, 160, 161 and 162, respectively;
- (11) SEQ ID NOs:127, 128, 129, 163, 164 and 165, respectively; or
- (12) SEQ ID NOs:130, 131, 132, 166, 167 and 168, respectively;

wherein the antibody or antigen-binding fragment thereof specifically binds DLL3, preferably specifically binds human DLL3.

Embodiment 3 is the isolated anti-DLL3 monoclonal antibody or antigen-binding fragment of embodiment 1 or 2, comprising a heavy chain variable region having a polypeptide sequence at least 95% identical to SEQ ID NO:1, 3, 5, 7, 9, 11, 13, 15, 17, 19, 21 or 23, or a light chain variable region having a polypeptide sequence at least 95% identical to SEQ ID NO:2, 4, 6, 8, 10, 12, 14, 16, 18, 20, 22 or 24.

Embodiment 4 is the isolated anti-DLL3 monoclonal antibody or antigen-binding fragment of any one of embodiments 1-3, comprising
- (a) a heavy chain variable region having the polypeptide sequence of SEQ ID NO:1, and a light chain variable region having the polypeptide sequence of SEQ ID NO:2;
- (b) a heavy chain variable region having the polypeptide sequence of SEQ ID NO:3, and a light chain variable region having the polypeptide sequence of SEQ ID NO:4;
- (c) a heavy chain variable region having the polypeptide sequence of SEQ ID NO:5, and a light chain variable region having the polypeptide sequence of SEQ ID NO:6;
- (d) a heavy chain variable region having the polypeptide sequence of SEQ ID NO:7, and a light chain variable region having the polypeptide sequence of SEQ ID NO:8;
- (e) a heavy chain variable region having the polypeptide sequence of SEQ ID NO:9, and a light chain variable region having the polypeptide sequence of SEQ ID NO:10;
- (f) a heavy chain variable region having the polypeptide sequence of SEQ ID NO:11, and a light chain variable region having the polypeptide sequence of SEQ ID NO:12;
- (g) a heavy chain variable region having the polypeptide sequence of SEQ ID NO:13, and a light chain variable region having the polypeptide sequence of SEQ ID NO:14;
- (h) a heavy chain variable region having the polypeptide sequence of SEQ ID NO:15, and a light chain variable region having the polypeptide sequence of SEQ ID NO:16;
- (i) a heavy chain variable region having the polypeptide sequence of SEQ ID NO:17, and a light chain variable region having the polypeptide sequence of SEQ ID NO:18;
- (j) a heavy chain variable region having the polypeptide sequence of SEQ ID NO:19, and a light chain variable region having the polypeptide sequence of SEQ ID NO:20;
- (k) a heavy chain variable region having the polypeptide sequence of SEQ ID NO:21, and a light chain variable region having the polypeptide sequence of SEQ ID NO:22; or
- (l) a heavy chain variable region having the polypeptide sequence of SEQ ID NO:23, and a light chain variable region having the polypeptide sequence of SEQ ID NO:24.

Embodiment 5 is the isolated anti-DLL3 monoclonal antibody or antigen-binding fragment of any one of embodiments 1-4, wherein the antibody or antigen-binding fragment thereof is chimeric.

Embodiment 6 is the isolated anti-DLL3 monoclonal antibody or antigen-binding fragment of any one of embodiments 1-4, wherein the antibody or antigen-binding fragment thereof is human or humanized.

Embodiment 7 is the isolated anti-DLL3 monoclonal antibody or antigen-binding fragment thereof of embodiment 6, wherein the antibody or antigen-binding fragment thereof comprises:
- (a) a heavy chain variable region having the polypeptide sequence of SEQ ID NO:170, and a light chain variable region having the polypeptide sequence of SEQ ID NO:171;
- (b) a heavy chain variable region having the polypeptide sequence of SEQ ID NO:170, and a light chain variable region having the polypeptide sequence of SEQ ID NO:172; or
- (c) a heavy chain variable region having the polypeptide sequence of SEQ ID NO:170, and a light chain variable region having the polypeptide sequence of SEQ ID NO:173.

Embodiment 8 is the isolated anti-DLL3 monoclonal antibody or antigen-binding fragment thereof of any one of embodiments 1-7, wherein the anti-DLL3 monoclonal antibody or antigen-binding fragment thereof is capable of inducing effector-mediated tumor cell lysis.

Embodiment 9 is an isolated anti-CD47 monoclonal antibody or antigen-binding fragment comprising a humanized heavy chain variable region of an anti-CD47 monoclonal antibody and a humanized light chain variable region of an anti-DLL3 monoclonal antibody, wherein the anti-CD47 monoclonal antibody or antigen-binding fragment thereof comprises:
- a. a heavy chain variable region having the polypeptide sequence of SEQ ID NO:175, and a light chain variable region having the polypeptide sequence of SEQ ID NO:171;
- b. a heavy chain variable region having the polypeptide sequence of SEQ ID NO:175, and a light chain variable region having the polypeptide sequence of SEQ ID NO:172;
- c. a heavy chain variable region having the polypeptide sequence of SEQ ID NO:175, and a light chain variable region having the polypeptide sequence of SEQ ID NO:173;
- d. a heavy chain variable region having the polypeptide sequence of SEQ ID NO:176, and a light chain variable region having the polypeptide sequence of SEQ ID NO:171;
- e. a heavy chain variable region having the polypeptide sequence of SEQ ID NO:176, and a light chain variable region having the polypeptide sequence of SEQ ID NO:172;
- f. a heavy chain variable region having the polypeptide sequence of SEQ ID NO:176, and a light chain variable region having the polypeptide sequence of SEQ ID NO:173;
- g. a heavy chain variable region having the polypeptide sequence of SEQ ID NO:177, and a light chain variable region having the polypeptide sequence of SEQ ID NO:171;
- h. a heavy chain variable region having the polypeptide sequence of SEQ ID NO:177, and a light chain variable region having the polypeptide sequence of SEQ ID NO:172;
- i. a heavy chain variable region having the polypeptide sequence of SEQ ID NO:177, and a light chain variable region having the polypeptide sequence of SEQ ID NO:173; or
- j. a heavy chain variable region having the polypeptide sequence of SEQ ID NO:177, and a light chain variable region having the polypeptide sequence of SEQ ID NO:174.

Embodiment 10 is the isolated anti-CD47 monoclonal antibody or antigen-binding fragment thereof of embodiment 9, wherein the anti-CD47 monoclonal antibody or antigen-binding fragment thereof is capable of blocking binding of CD47 to signal regulatory protein alpha (SIRPα).

Embodiment 11 is the isolated anti-CD47 monoclonal antibody or antigen-binding fragment thereof of embodiment 9, wherein the anti-CD47 monoclonal antibody or antigen-binding fragment thereof is capable of inducing macrophage-mediated phagocytosis of cancer cells.

Embodiment 12 is an isolated humanized anti-CD47/DLL3 bispecific antibody or antigen-binding fragment thereof comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 178, 179 and 180; the second antigen-binding domain comprises a heavy chain complementarity determining region 1 (HCDR1), HCDR2, HCDR3, having the polypeptide sequences of SEQ ID NOs: 181, 182 and 183; and the first antigen-binding domain and the second antigen-binding domain each comprises a light chain complementarity determining region 1 (LCDR1), LCDR2, and LCDR3, having the polypeptide sequences of SEQ ID NOs: 184, 185 and 186.

Embodiment 13 is an isolated humanized anti-CD47/DLL3 bispecific antibody or antigen-binding fragment comprising a first antigen-binding domain that specifically binds CD47, preferably human CD47, and a second antigen-binding domain that specifically binds DLL3, preferably human DLL3, wherein the first antigen-binding domain comprises a heavy chain complementarity determining region 1 (HCDR1), HCDR2, HCDR3, having the polypeptide sequences of SEQ ID NOs: 187, 188 and 189; the second antigen-binding domain comprises a heavy chain complementarity determining region 1 (HCDR1), HCDR2, HCDR3, having the polypeptide sequences of SEQ ID NOs: 190, 191 and 192; and the first antigen-binding domain and the second antigen-binding domain each comprises a light chain complementarity determining region 1 (LCDR1), LCDR2, and LCDR3, having the polypeptide sequences of SEQ ID NOs: 193, 194 and 195.

Embodiment 14 is the isolated humanized anti-CD47/DLL3 bispecific antibody or antigen-binding fragment thereof of embodiment 12 or 13, wherein the first antigen-binding domain comprises a heavy chain variable region having a polypeptide sequence at least 95% identical to SEQ ID NO:176, and a light chain variable region having a polypeptide sequence at least 95% identical to SEQ ID NO:172; and wherein the second antigen-binding domain comprises a heavy chain variable region a polypeptide sequence at least 95% identical to SEQ ID NO:170, and a light chain variable region having a polypeptide sequence at least 95% identical to SEQ ID NO:172.

Embodiment 15 is the isolated humanized anti-CD47/DLL3 bispecific antibody or antigen-binding fragment thereof of any one of embodiments 12-14, wherein the humanized anti-CD47/DLL3 bispecific antibody or antigen-binding fragment thereof is capable of blocking binding of CD47 to SIRPα on cancer cells that express both DLL3 and CD47.

Embodiment 16 is the isolated humanized anti-CD47/DLL3 bispecific antibody or antigen-binding fragment thereof of any one of embodiments 12-14, wherein the humanized anti-CD47/DLL3 bispecific antibody or antigen-binding fragment thereof is capable of inducing macrophage-mediated phagocytosis of cancer cells that express both DLL3 and CD47.

Embodiment 17 is the isolated humanized anti-CD47/DLL3 bispecific antibody or antigen-binding fragment thereof of any one of embodiments 12-14, wherein the humanized anti-CD47/DLL3 bispecific antibody or antigen-binding fragment thereof is capable of binding cancer cells that express both DLL3 and CD47 with minimal to undetectable binding to human red blood cells (RBCs).

Embodiment 18 is an isolated nucleic acid encoding the anti-DLL3 monoclonal antibody or antigen-binding fragment thereof, the anti-CD47 monoclonal antibody or antigen-binding fragment thereof, or the humanized anti-CD47/DLL3 bispecific antibody or antigen-binding fragment of any one of embodiments 1-17.

Embodiment 19 is a vector comprising the isolated nucleic acid of embodiment 18.

Embodiment 20 is a host cell comprising the vector of embodiment 19.

Embodiment 21 is a pharmaceutical composition, comprising the isolated anti-DLL3 monoclonal antibody or antigen-binding fragment thereof, the anti-CD47 monoclonal antibody or antigen-binding fragment thereof, or the humanized anti-CD47/DLL3 bispecific antibody or antigen-binding fragment thereof of any one of embodiments 1-17 and a pharmaceutically acceptable carrier.

Embodiment 22 is a method of targeting DLL3 on a cancer cell surface in a subject in need thereof, comprising administering to the subject in need thereof the pharmaceutical composition comprising the isolated anti-DLL3 monoclonal antibody or antigen-binding fragment thereof of any one of embodiments 1-8.

Embodiment 23 is a method of blocking binding of CD47 to signal regulatory protein alpha (SIRPα) in a subject in need thereof, comprising administering to the subject in need thereof the pharmaceutical composition comprising the anti-CD47 monoclonal antibody or antigen-binding fragment thereof of any one of embodiments 9-11.

Embodiment 24 is a method of inducing macrophage-mediated phagocytosis of cancer cells in a subject in need thereof, comprising administering to the subject in need thereof the pharmaceutical composition comprising the anti-CD47 monoclonal antibody or antigen-binding fragment thereof of any one of embodiments 9-11.

Embodiment 25 is a method of targeting DLL3 and CD47 that are both expressed on a cancer cell surface in a subject in need thereof, comprising administering to the subject in need thereof the pharmaceutical composition comprising the isolated humanized anti-CD47/DLL3 bispecific antibody or antigen-binding fragment thereof of any one of embodiments 12-17.

Embodiment 26 is a method of blocking binding of CD47 to SIRPα on cancer cells that express both DLL3 and CD47 in a subject in need thereof, comprising administering to the subject in need thereof the pharmaceutical composition comprising the humanized anti-CD47/DLL3 bispecific antibody or antigen-binding fragment thereof of any one of embodiments 12-17.

Embodiment 27 is a method of inducing macrophage-mediated phagocytosis of cancer cells that express both DLL3 and CD47 in a subject in need thereof, comprising administering to the subject in need thereof the pharmaceutical composition comprising the humanized anti-CD47/DLL3 bispecific antibody or antigen-binding fragment thereof of any one of embodiments 12-17.

Embodiment 28 is a method of binding cancer cells that express both DLL3 and CD47 with minimal to undetectable binding to human red blood cells (RBCs) in a subject in need thereof, comprising administering to the subject in need thereof the pharmaceutical composition comprising the humanized anti-CD47/DLL3 bispecific antibody or antigen-binding fragment thereof of any one of embodiments 12-17.

Embodiment 29 is a method of treating cancer in a subject in need thereof, comprising administering to the subject in need thereof the pharmaceutical composition of embodiment 21.

Embodiment 30 is the method of embodiment 29, wherein the cancer is selected from the group consisting of a lung cancer, such as small cell lung cancer (SCLC), large cell neuroendocrine carcinoma (LCNEC), a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Embodiment 31 is a method of producing the anti-DLL3 monoclonal antibody or antigen-binding fragment thereof, the anti-CD47 monoclonal antibody or antigen-binding fragment thereof, or the humanized anti-CD47/DLL3 bispecific antibody or antigen-binding fragment thereof of any one of embodiments 1-17, comprising culturing a cell comprising a nucleic acid encoding the antibody or antigen-binding fragment thereof under conditions to produce the antibody or antigen-binding fragment thereof, and recovering the antibody or antigen-binding fragment thereof from the cell or culture.

Embodiment 32 is a method of producing a pharmaceutical composition comprising the anti-DLL3 monoclonal antibody or antigen-binding fragment thereof, the anti-CD47 monoclonal antibody or antigen-binding fragment thereof, or the humanized anti-CD47/DLL3 bispecific antibody or antigen-binding fragment thereof of any one of embodiments 1-17, comprising combining the antibody or antigen-binding fragment thereof with a pharmaceutically acceptable carrier to obtain the pharmaceutical composition.

Embodiment 33 is a method of determining a level of DLL3 in a subject, the method comprising:
a. obtaining a sample from the subject;
b. contacting the sample with the isolated anti-DLL3 monoclonal antibody or antigen-binding fragment thereof of any one of embodiments 1-8; and
c. determining a level of DLL3 in the subject.

Embodiment 34 is the method of embodiment 33, wherein the sample is a tissue sample.

Embodiment 35 is the method of embodiment 34, wherein the tissue sample is a cancer tissue sample.

Embodiment 36 is the method of embodiment 33, wherein the sample is a blood sample.

EXAMPLES

Example 1: Identification of Anti-DLL3 Monoclonal Antibodies

Mice were immunized with recombinant FLAG-huDLL3 (Adipogen, Cat #: AG40B-0151), a fusion protein of human DLL3 extracellular domain (ECD) with FLAG tag at the N-terminus. Plasma titer was determined by ELISA. After euthanization, spleens and lymph nodes were collected to produce hybridomas. Hybridomas were grown in 384-well tissue culture plates and supernatants from individual wells were screened by ELISA using FLAG-huDLL3, FACS using stable pools of HEK293-huDLL3 and HEK293-cyDLL3, and Octet off-rate analysis using FLAG-huDLL3. Top positive clones were isolated and sequenced.

Sequences of heavy and light chain variable regions for anti-DLL3 monoclonal antibodies are provided in Tables 1 and 2, and the CDR regions for the anti-DLL3 monoclonal antibodies are provided in Tables 3-6.

TABLE 1

Sequences of heavy chain variable regions for anti-DLL3 mAbs

| mAb clones | VH | SEQ ID NO: |
|---|---|---|
| 13P9A | EVQLQQSGPELVKPGASVKMSCKASGYTFTSYVMHWVKQKPGQGPDWIGYINPYNDATKYNEKFKGKATLTSDKSSSTAYMELSSLTSEDSAVYYCARGGYDYDGDYWGQGTTLTVSS | 1 |
| 5A16A | EVQLQQSGPELVKPGASVKMSCKASGYTFTRYILHWVKLKPGQGLEWIGYINPYNDGTKYNEKFKGKATLTSDKSSSTAYMELSRLTSYDSAVYYCARDSSGYGGAYAMDFWGQGTSVTVSS | 3 |
| 14L22A | EVQLVESGGGLVKPGGSLKLSCAASGFTFSSYAMSWVRQTPEKRLEWVAAINSNGGNTYYPDTVKDRFTISRDNAKNTLYLQMSSLRSEDTALYYCARHRGGFYYAVDYWGQGTSVTVSS | 5 |
| 10P18A | EVQLQQSGPELVKPGASVKISCKASGYSFTGYYIDWVKQSPGKSLEWIGYIYPSNGETSYNQKFKGKATLTVDKSSSTVNMQLNSLTSEDSAVYYCARESYAMDYWGQGTSVTVSS | 7 |
| 13P11A | DVQLQESGPGLVKPSQTVSLTCTVTGYSTINGNHWWSWIRQVSGSKLEWMGYISSSGSTDSNPSLKSRISITRDTSKNQLFLHLNSVTTEDIATYYCATTGTWGYFDYWGQGTTLTVSS | 9 |
| 3C16A | EVQLQQSGPELVKPGTSVKMSCKASGYTFTSYVMHWVKQKPGQGLEWIGYVIPYNDGTKYNEKFKGKATLTSDKSSSTAYMELSSLTSEDSAVYYCARPSNWDEFDYWGQGTTLTVSS | 11 |
| 3I21A | QVQLQQPGAELVKPGASVKLSCKASGYTFTNYWMNWVKQRPGRGLEWIGRIHPSDSETHYNQKFKTKATLTVDKSSSTAYIQLSSLTSEDSAVYYCARYDGYFAYWGQGTLVTVSA | 13 |
| 8H5A | QVTLKESGPGILQPSQTLSLTCSFSGFSLSTFGMGVGWIRQPSGKGLEWLAHIWWDDDKYYNPALKSRLTISKDTSKNQVFLKIANVDIADTATYYCARTYDYDEYFDYWGQGTTLTVSS | 15 |
| 15K2A | QVQLQQPGAELVQPGASVKLSCKASGYTFTSYWMNWMKQRPGRGLEWIGRIHPSDSETHYNQKFRTKATLTVDKSSSTAYIQLSSLTSEDSAVYYCAREDGYYWYFDVWGAGTTVTVSS | 17 |
| 5A24A | EVQLQQSGAELVKPGASVKIPCKASGYKFTDFNMDWVKQSHGKSLEWIGDINPNSGGTIYNQKFKGKATLTVDKSLSTAYMELGSLTSEDTAVYYCARWDYGNFAYWGQGTLVTVSA | 19 |
| 15P17A | QVQLQQPGAELVKPGASVKLSCKASGYTFTNYWMNWVKQRPGRGLEWIGRIHPSDSETHYNQKFKSKATLTVDKSSSTAYIQLSSLTSEDSAVYYCAREDGYYWYFDVWGAGTTVTVSS | 21 |
| 15N21A | EVQLVESGGGLVKPGGSLKLSCAASGFTFSSYAMSWVRQTPEKRLEWVAAINSNGGRNYYPDTVKDRFTISRDNAKNTLYLQMSSLRSEDTALYYCARHRGGYYYAMDYWGQGTSVTVSS | 23 |

VH: heavy chain variable region

TABLE 2

Sequences of light chain variable regions for anti-DLL3 mAbs

| mAb clones | VL | SEQ ID NO: |
|---|---|---|
| 13P9A | DIQMNQSPSSLSASLGDSITITCHASQNINVWLSWYQQKPGNIPKLLIYKASNLHTGVPSRFSGSGSGTGFTLTISSLQPEDIATYYCQQGQSYPFTFGSGTKLEIK | 2 |
| 5A16A | DIQMTQSPASLSASVGETVTITCRASGNIHNYLAWYQQKQGRSPQLLVYNAKTLPYGVPSRFSGSGSGTQYSLKINSLQPEDFGSYYCQHFWTTPWTFGGGTKLEIK | 4 |

TABLE 2-continued

Sequences of light chain variable regions for anti-DLL3 mAbs

| mAb clones | VL | SEQ ID NO: |
|---|---|---|
| 14L22A | NIMMTQSPSSLAVSAGEKVTMSCKSSQSVLYSSNQKNYLAWYQQKPGQSPKLLIYWASTRESGVPDRFTGSGSGTDFTLTISSVQAEDLAVYYCHQYLSSRTFGGGTKLEIK | 6 |
| 10P18A | DIVLTQSPASLAVSLGQRATISCRASKSVSTSGYSYMHWYQQKPGQPPKLLIYLASNLESGVPARFSGSGSGTDFTLNIHPVEEEDAATYYCQHSRELPYTFGGGTKLEIK | 8 |
| 13P11A | NIVMTQSPKSMSMSVGERVTLSCKASENVGTYVSWYQQKPEQSPKLLIYGASNRFTGVPDRFTGSGSATDFTLTISSVQAEDLADYHCGQSYSYPFTFGSGTKLEIK | 10 |
| 3C16A | DIVMTQSQKFMSTSVGDRVSITCKASQNVRTAVAWYQQKPGQSPKALIYLASNRHTGVPDRFTGSGSGTDFTLTISNVQSEDLADYFCLQHWNYPLTFGAGTKLELK | 12 |
| 3I21A | DIQMTQSSSYLSVSLGGRVTITCKASDHINNWLAWYQQKPGNAPRLLISGATSLETGDPSRFSGSGSGKDYTLSITSLQIEDVATYYCQQYWSIPFTFGAGTKLELK | 14 |
| 8H5A | DIVMTQAAFSNPVTLGTSASISCRSSKSLLHSNGITYFYWYLQKPGQSPQLLIYQMSNLASGVPDRFSSSGSGTDFTLRISRVEAEDVGVYYCAQNLELPFTFGSGTKLEIK | 16 |
| 15K2A | NIVLTQSPASLAVSLGQRATISCRASESVDIYGNSFMHWYQQKPGQPPKLLIYLASNLESGVPARFSGSGSRTDFTLTIDPVEADDAATYYCQQNNEDPWTFGGGTKLEIK | 18 |
| 5A24A | DIVMTQAAFSNPVTLGTSASISCRSSKSLLHSNGITYLYWYLQKPGQSPQLLIYQMSNLASGVPDRFSSSGSGTDFTLRISRVEAEDVGVYYCAQNLELPLTFGAGTKLELK | 20 |
| 15P17A | NIVLTQSPASLAVSLGQRATISCRASESVDSYGNSFMHWYQQKPGQPPKLLIYLASNLESGVPARFSGSGSRTDFTLTIDPVEADDAATYYCQQNHEDPWTFGGGTKLEIK | 22 |
| 15N21A | DIVMSQSPSSLAVSVGEKVTMSCKSSQSLLYSSNQKNYLAWYQQKPGQSPKLLIYWASTRESGVPDRFTGSGSGTDFTLTISSVKAEDLAVYYCQQYYTYLTFGAGTKLELK | 24 |

VL: light chain variable region

TABLE 3

CDR regions 1-3 of heavy chain for anti-DLL3 mAbs

| mAb clones | HC CDR1 | SEQ ID NO: | HC CDR2 | SEQ ID NO: | HC CDR3 | SEQ ID NO: |
|---|---|---|---|---|---|---|
| 13P9A | GYTFTSYV | 25 | INPYNDAT | 26 | ARGGYDYDGDY | 27 |
| 5A16A | GYTFTRYI | 28 | INPYNDGT | 29 | ARDSSGYGGAYAMDF | 30 |
| 14L22A | GFTFSSYA | 31 | INSNGGNT | 32 | ARHRGGFYYAVDY | 33 |
| 10P18A | GYSFTGYY | 34 | IYPSNGET | 35 | ARESYAMDY | 36 |
| 13P11A | GYSFINGNHW | 37 | ISSSGST | 38 | ATTGTWGYFDY | 39 |
| 3C16A | GYTFTSYV | 40 | VIPYNDGT | 41 | ARPSNWDEFDY | 42 |
| 3I21A | GYTFTNYW | 43 | IHPSDSET | 44 | ARYDGYFAY | 45 |
| 8H5A | GFSLSTFGMG | 46 | IWWDDDK | 47 | ARTYDYDEYFDY | 48 |
| 15K2A | GYTFTSYW | 49 | IHPSDSET | 50 | AREDGYYWYFDV | 51 |
| 5A24A | GYKFTDFN | 52 | INPNSGGT | 53 | ARWDYGNFAY | 54 |
| 15P17A | GYTFTNYW | 55 | IHPSDSET | 56 | AREDGYYWYFDV | 57 |
| 15N21A | GFTFSSYA | 58 | INSNGGRN | 59 | ARHRGGYYYAMDY | 60 |

HC: heavy chain; CDR: complementarity determining region

The HC CDRs for the anti-DLL3 mAbs were determined utilizing the IMGT method (Lefranc, M.-P. et al., Nucleic Acids Res. 1999; 27:209-212).

TABLE 4

CDR regions 1-3 of light chain for anti-DLL3 mAbs

| mAb clones | LC CDR1 | SEQ ID NO: | LC CDR2 | SEQ ID NO: | LC CDR3 | SEQ ID NO: |
|---|---|---|---|---|---|---|
| 13P9A | QNINVW | 61 | KAS | 62 | QQGQSYPFT | 63 |
| 5A16A | GNIHNY | 64 | NAK | 65 | QHFWTTPWT | 66 |
| 14L22A | QSVLYSSNQKNY | 67 | WAS | 68 | HQYLSSRT | 69 |
| 10P18A | KSVSTSGYSY | 70 | LAS | 71 | QHSRELPYT | 72 |
| 13P11A | ENVGTY | 73 | GAS | 74 | GQSYSYPFT | 75 |
| 3C16A | QNVRTA | 76 | LAS | 77 | LQHWNYPLT | 78 |
| 3I21A | DHINNW | 79 | GAT | 80 | QQYWSIPFT | 81 |
| 8H5A | KSLLHSNGITY | 82 | QMS | 83 | AQNLELPFT | 84 |
| 15K2A | ESVDIYGNSF | 85 | LAS | 86 | QQNNEDPWT | 87 |
| 5A24A | KSLLHSNGITY | 88 | QMS | 89 | AQNLELPLT | 90 |
| 15P17A | ESVDSYGNSF | 91 | LAS | 92 | QQNHEDPWT | 93 |
| 15N21A | QSLLYSSNQKNY | 94 | WAS | 95 | QQYYTYLT | 96 |

LC: light chain; CDR: complementarity determining region

The LC CDRs for the anti-DLL3 mAbs were determined utilizing the IMGT method (Lefranc, M.-P. et al., Nucleic Acids Res. 1999; 27:209-212).

TABLE 5

CDR regions 1-3 of heavy chain for anti-DLL3 mAbs

| mAb clones | HC CDR1 | SEQ ID NO: | HC CDR2 | SEQ ID NO: | HC CDR3 | SEQ ID NO: |
|---|---|---|---|---|---|---|
| 13P9A | SYVMH | 97 | YINPYNDATKYNEKFKG | 98 | GGYDYDGDY | 99 |
| 5A16A | RYILH | 100 | YINPYNDGTKYNEKFKG | 101 | DSSGYGGAYAMDF | 102 |
| 14L22A | SYAMS | 103 | AINSNGGNTYYPDTVKD | 104 | HRGGFYYAVDY | 105 |
| 10P18A | GYYID | 106 | YIYPSNGETSYNQKFKG | 107 | ESYAMDY | 108 |
| 13P11A | NGNHWWS | 109 | YISSSGSTDSNPSLKS | 110 | TGTWGYFDY | 111 |
| 3C16A | SYVMH | 112 | YVIPYNDGTKYNEKFKG | 113 | PSNWDEFDY | 114 |
| 3I21A | NYWMN | 115 | RIHPSDSETHYNQKFKT | 116 | YDGYFAY | 117 |
| 8H5A | TFGMGVG | 118 | HIWWDDDKYYNPALKS | 119 | TYDYDEYFDY | 120 |
| 15K2A | SYWMN | 121 | RIHPSDSETHYNQKFRT | 122 | EDGYYWYFDV | 123 |
| 5A24A | DFNMD | 124 | DINPNSGGTIYNQKFKG | 125 | WDYGNFAY | 126 |
| 15P17A | NYWMN | 127 | RIHPSDSETHYNQKFKS | 128 | EDGYYWYFDV | 129 |
| 15N21A | SYAMS | 130 | AINSNGGRNYYPDTVKD | 131 | HRGGYYYAMDY | 132 |

HC: heavy chain; CDR: complementarity determining region

The HC CDRs for the anti-DLL3 mAbs were determined utilizing the Kabat method (Elvin A. Kabat et al, Sequences of Proteins of Immunological Interest 5th ed. (1991)).

TABLE 6

CDR regions 1-3 of light chain for anti-DLL3 mAbs

| mAb clones | LC CDR1 | SEQ ID NO: | LC CDR2 | SEQ ID NO: | LC CDR3 | SEQ ID NO: |
|---|---|---|---|---|---|---|
| 13P9A | HASQNINVWLS | 133 | KASNLHT | 134 | QQGQSYPFT | 135 |
| 5A16A | RASGNIHNYLA | 136 | NAKTLPY | 137 | QHFWTTPWT | 138 |
| 14L22A | KSSQSVLYSSNQKNYLA | 139 | WASTRES | 140 | HQYLSSRT | 141 |
| 10P18A | RASKSVSTSGYSYMH | 142 | LASNLES | 143 | QHSRELPYT | 144 |
| 13P11A | KASENVGTYVS | 145 | GASNRFT | 146 | GQSYSYPFT | 147 |
| 3C16A | KASQNVRTAVA | 148 | LASNRHT | 149 | LQHWNYPLT | 150 |
| 3I21A | KASDHINNWLA | 151 | GATSLET | 152 | QQYWSIPFT | 153 |
| 8H5A | RSSKSLLHSNGITYFY | 154 | QMSNLAS | 155 | AQNLELPFT | 156 |
| 15K2A | RASESVDIYGNSFMH | 157 | LASNLES | 158 | QQNNEDPWT | 159 |
| 5A24A | RSSKSLLHSNGITYLY | 160 | QMSNLAS | 161 | AQNLELPLT | 162 |
| 15P17A | RASESVDSYGNSFMH | 163 | LASNLES | 164 | QQNHEDPWT | 165 |
| 15N21A | KSSQSLLYSSNQKNYLA | 166 | WASTRES | 167 | QQYYTYLT | 168 |

LC: light chain; CDR: complementarity determining region

The LC CDRs for the anti-DLL3 mAbs were determined utilizing the Kabat method (Elvin A. Kabat et al, Sequences of Proteins of Immunological Interest 5th ed. (1991)).

Example 2: Production and Purification of Chimeric mAbs from the Culture Media of Transfected Cells To obtain the recombinant anti-DLL3 chimeric mAbs, the expression vectors containing the mouse variable regions (VH and VL) fused to the constant regions of human IgG1 heavy chain and kappa light chain, respectively, were transiently transfected into 293E, ExpiCHO-S, or Expi293F cells. The recombinant antibodies produced in the suspension of the cells were purified using Protein A affinity chromatography.

Example 3: ELISA Binding Analysis of Purified Chimeric Antibodies

Figure 1B:
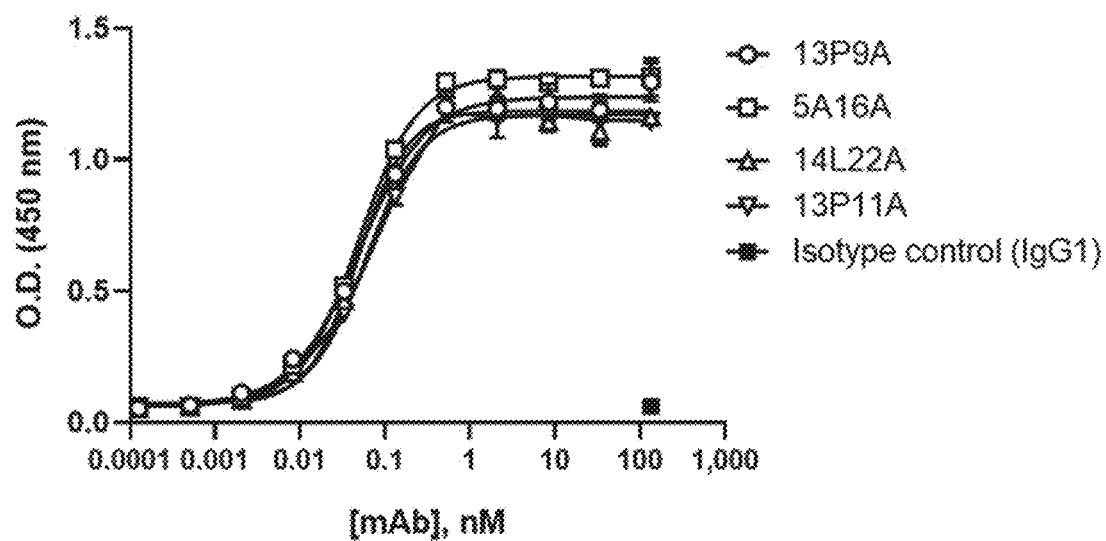
Figure 1C:
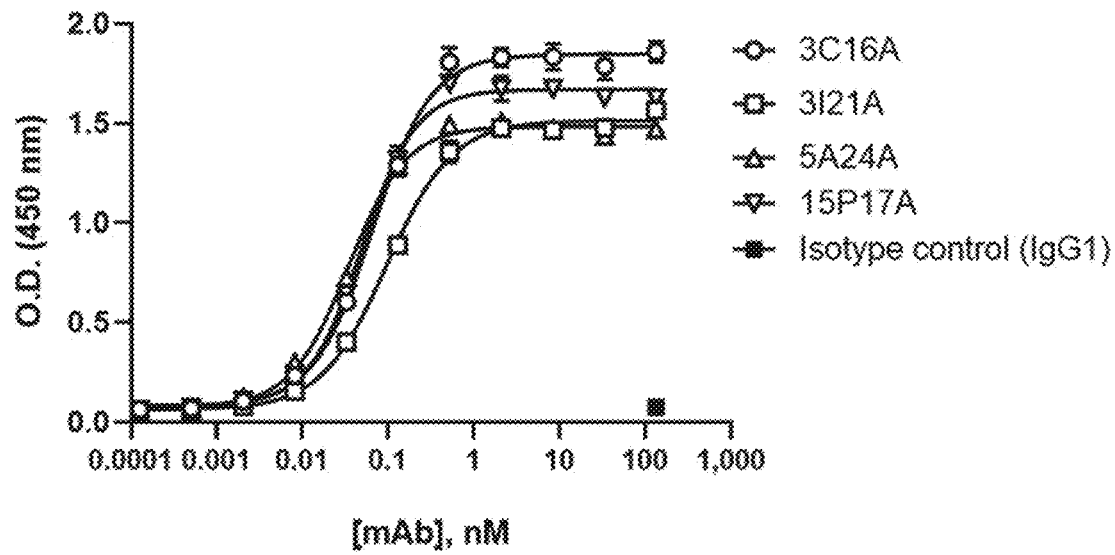

FLAG-huDLL3 in carbonate coating buffer (50 µL/well at 0.25 µg/mL) was coated on an ELISA plate for 1 hour at room temperature. After washing, the ELISA plate was blocked in 5% BSA in TBST for 1 hour at room temperature and washed again. An anti-DLL3 mAb was added, mixed, and incubated for 1 hour at room temperature. The plate was washed and the binding of anti-DLL3 mAb to the immobilized FLAG-huDLL3 was detected by adding a secondary antibody, an anti-human IgG conjugated to horseradish peroxidase (hIgG-HRP) (ThermoFisher Scientific, Cat #: H10007) in 5% BSA in TBST, incubating for 1 hour, and then washing the plate. The ELISA was developed using One-step Detection Solution (ThermoFisher Scientific, Cat #: 34028) and measured as the absorbance at 450 nm. An isotype control IgG1 mAb that does not cross-react with DLL3 was used as negative control to ensure assay specificity. Binding results of the chimeric anti-DLL3 mAbs are provided in FIGS. 1A-1C.

Example 4: FACS Analysis of Chimeric Anti-DLL3 mAbs

Figure 2A:
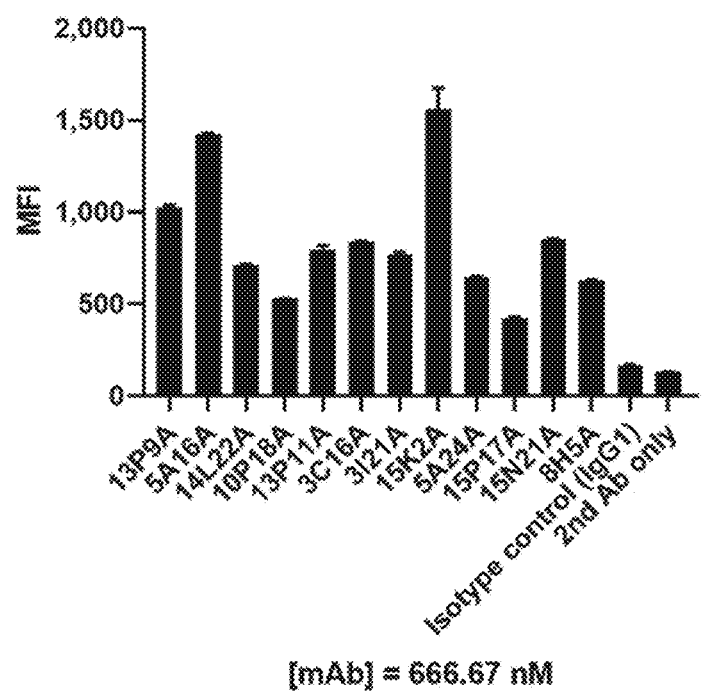
FIGS. 2A-2C show the binding of chimeric anti-DLL3 mAbs to HEK293-huDLL3 cells by FACS. Three different mAb concentrations were used in the assay (666.67 nM (FIG. 2A); 333.33 nM (FIG. 2B); and 66.67 nM (FIG. 2C)).
Figure 2B:
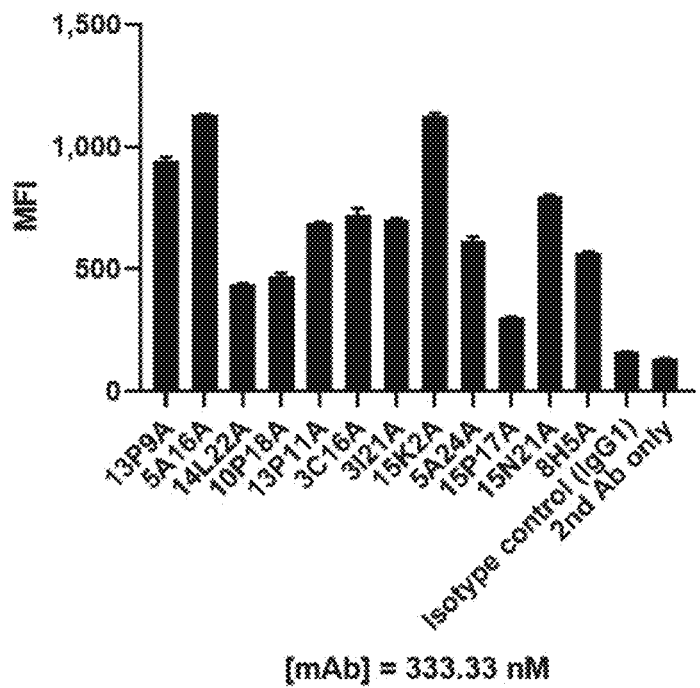
Figure 2C:
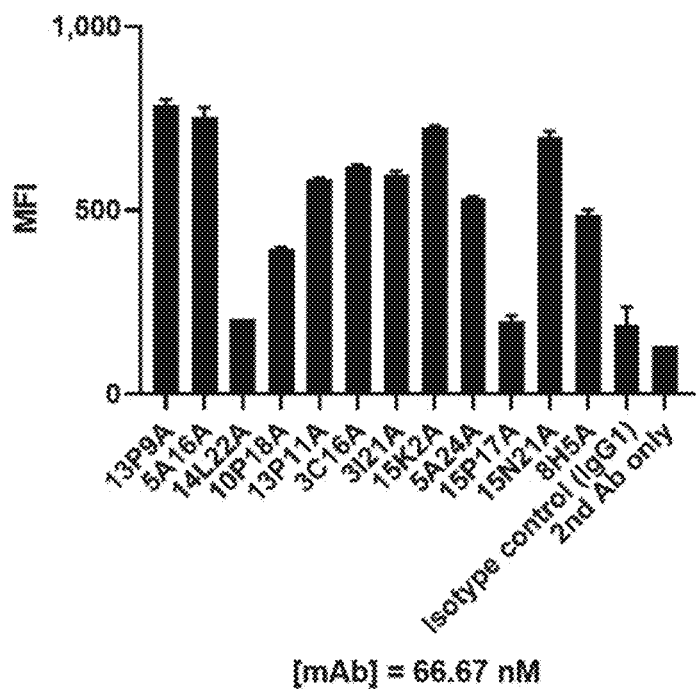

A HEK293 cell line stably expressing human DLL3 (HEK-huDLL3) was used in a FACS assay. The cells (100,000 cells per well on a 96-well plate) were incubated with either a solution of the purified mAbs at various concentrations (e.g., 666.67 nM, 333.33 nM, or 66.67 nM) or an isotype control in Hanks' Balanced Salt Solution (HBSS) containing 0.05% sodium azide and 0.1% BSA. Using an Alexa Fluor 488-conjugated anti-human IgG secondary antibody (ThermoFisher, Cat #: H10120), the presence of the mAb on HEK293-huDLL3 cells was measured by FACS (Attune NxT; ThermoFisher, Carlsbad, CA). The result of the FACS binding analysis is provided in FIGS. 2A-2C.

Example 5: Humanization of an Anti-DLL3 mAb

The mouse anti-DLL3 13P9A was humanized to reduce the potential of immunogenicity when used in human patients. The sequences of the variable regions of the heavy and light chains (VH and VL) were compared with the human antibody sequences in the Protein Data Bank (PDB) database and homology models were built. The CDRs in both the heavy and light chains of the mouse mAbs were grafted into human frameworks that have the highest possibility of maintaining the proper structure likely required for antigen binding. Backmutations from human residues to mouse residues or other mutations were designed when necessary. The sequences of the humanized VH and VL regions are shown in Tables 7 and 8. The humanized VH and VL regions were fused to the constant regions of human IgG4 heavy chain and kappa light chain, respectively. Antibodies were purified from transiently transfected 293E cells and analyzed for their ability to bind recombinant human FLAG-huDLL3 on a plate using ELISA. The $EC_{50}$ values for DLL3 binding by the humanized mAbs are provided in Table 9.

TABLE 7

Sequence of the humanized heavy chain variable region of anti-DLL3 mAb 13P9A

| Design | VH | SEQ ID NO: |
|---|---|---|
| H1 | EVRLSQSGGQMKKPGESMRLSCRASGYTFTSYVMH WVRQAPGRRPEWIGYINPYNDATKYARKFQGRATL TSDKYSDTAFLELRSLTSDDTAVYYCARGGYDYDG DYWGRGAPVTVSS | 170 |

TABLE 8

Sequences of humanized light chain variable regions of anti-DLL3 mAb 13P9A

| Design | VL | SEQ ID NO: |
|---|---|---|
| L1 | EIVMTQSPGTLSLSPGERATLSCHASQNINVWLSWYQQKPGQAPRLLIYKA SNLHTGIPDRFSGSGSGTDFTLTISRLEPEDFAVYYCQQGQSYPFTFGQGTK VEIK | 171 |
| L2 | EIVLTQSPGTLSLSPGERATLSCHASQNINVWLSWYQQKPGQAPRLLIYKA SNLHTGIPDRFSGSGSGTDFTLTISRLEPEDFAVYYCQQGQSYPFTFGQGTK VEIK | 172 |
| L3 | EIVMTQSPATLSLSPGETAIISCHASQNINVWLSWYQQRPGQAPRLLIYKAS NLHTGIPDRFSGSGWGTDFNLSISNLESGDFGVYYCQQGQSYPFTFGQGTK VEIK | 173 |
| L4 | EIVMTQSPATLSLSPGETAIISCHASQNINVWLSWYQQRPGQAPRLLIYKAS NLHTGIPDRFSGSGWGTDFNLSISNLESGDFGVYYCQQGQSYPWTFGQGT KVEIK | 174 |

TABLE 9

EC$_{50}$ values for DLL3 binding by humanized anti-DLL3 mAbs in an ELISA assay

| mAb ID | EC50 (nM) |
|---|---|
| H1L1 | 0.13 |
| H1L2 | 0.12 |
| H1L3 | 0.15 |

H1L1 refers to the mAb with the H1 heavy chain variable region and the L1 light chain variable region; all the other humanized mAbs in the table adopt the same naming rule.

Figure 3:
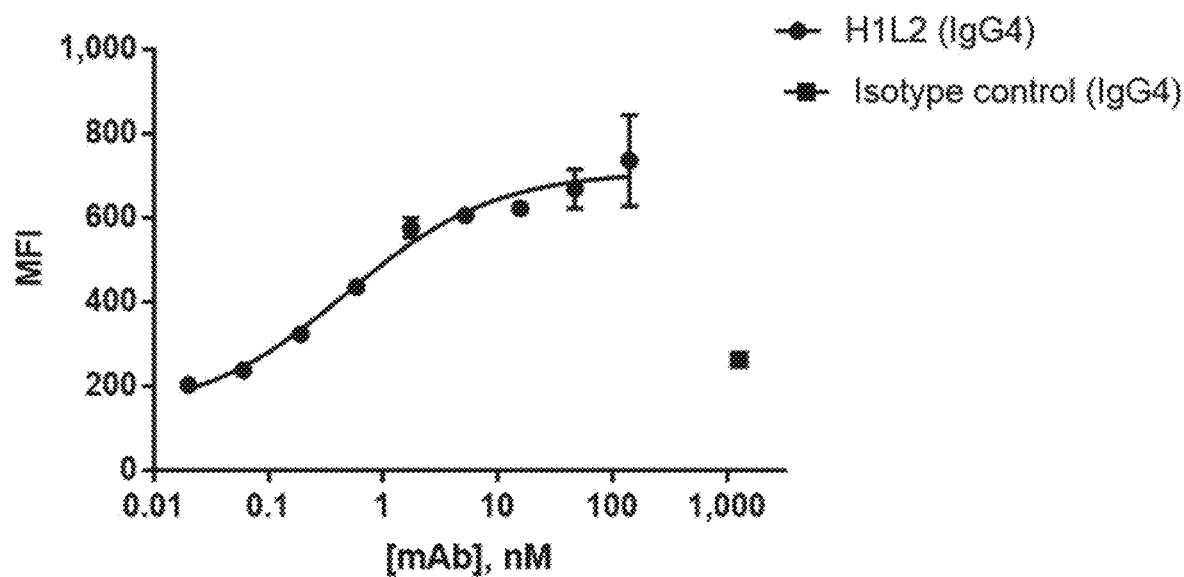
FIG. 3 shows the binding of humanized anti-DLL3 mAb H1L2 to SHP-77 cells by FACS.

The humanized anti-DLL3 mAb H1L2 was analyzed by flow cytometry for its ability to bind cell surface DLL3. SHP-77 cells have been reported to express DLL3 (Barretina et al., Nature 483(7391):603-7 (2012)) and therefore were used in the assay. SHP-77 (ATCC #CRL-2195) cells (14,000 cells per well on a 96-well plate) were incubated with either a solution of the purified mAb at various concentrations or an isotype control in Hanks' Balanced Salt Solution (HBSS) containing 0.05% sodium azide and 0.1% BSA. Using a PE-Cy7-conjugated anti-human IgG secondary antibody, the presence of the mAb on SHP-77 cells was measured by FACS (Attune NxT; ThermoFisher, Carlsbad, CA). The result of the FACS binding analysis is provided in FIG. 3.

Example 6: Assembly of Anti-CD47 mAbs Using the Humanized Heavy Chain Variable Region of an Anti-CD47 mAb and the Humanized Light Chain Variable Region of an Anti-DLL3 mAb To assess whether the humanized light chain variable (VL) regions of the anti-DLL3 mAb in Table 8 can form mAbs with the heavy chain variable (VH) region of anti-CD47 mAb 17C6A (described in International Patent Application No. PCT/US18/44384), humanized sequences of the VH region of 17C6A provided in Table 10 were used for antibody expression. The humanized VL regions of the anti-DLL3 mAb in Table 8 and the humanized VH regions of 17C6A in Table 10 were fused to the constant regions of human kappa light chain and IgG4 heavy chain, respectively, and the mAbs were expressed in 293E cells or ExpiCHO-S cells. The recombinant antibodies produced in the suspension of the 293E cell or ExpiCHO-S cultures were purified using Protein A affinity chromatography.

The purified mAbs were analyzed for their ability to bind to the extracellular domain of CD47 (CD47(ECD)) in an ELISA assay as follows: human CD47(ECD) (AcroBio, Cat #: CD7-HA2E9-50 µg) in carbonate coating buffer (50 µL/well at 1 µg/mL) was coated on a 96-well ELISA plate for 1 hour at room temperature. After washing, the plate was blocked in 5% BSA in TBST for 1 hour at room temperature and washed again. In each well of the plate, an antibody at 50 µL/well at various concentrations was added and incubated for 1 hour at room temperature. The plate was washed and the binding of the antibody to the immobilized CD47 was detected by incubating with anti-human IgG conjugated to horseradish peroxidase (hIgG-HRP) (ThermoFisher Scientific, Cat #: H10007) for 60 minutes at room temperature. Then after washing, the ELISA was developed using One-step Detection Solution (ThermoFisher Scientific, Cat #: 34028) and measured as the absorbance at 450 nm. The binding EC$_{50}$ values are shown in Table 11. These data indicate that the humanized anti-DLL3 light chains can pair with the humanized heavy chains of 17C6A to form mAbs with strong affinity for CD47.

TABLE 10

Sequences of humanized heavy chain variable regions of an anti-CD47 mAb

| Design | VH | SEQ ID NO: |
|---|---|---|
| KH1 | QVQLVQSGAEVKKPGSSVKVSCKASGYTFTSYWMHWVRQAPGQGLEWIGNIDPSDSETHYAQKFQGRATLTVDKSTSTAYMELSSLRSEDTAVYYCAGTDLAYWGQGTLVTVSS | 175 |
| KH2 | QVQLVQSGAEVKKPGASVKVSCKASGYTFTSYWMHWVRQAPGQGLEWIGNIDPSDSETHYAQKFQGRVTLTVDKSTSTVYMELSSLRSEDTAVYYCAGTDLAYWGQGTLVTVSS | 176 |
| KH3 | EVRLSQSGGQMKKPGESMRLSCRASGYTFTSYWMHWVRQAPGRRLEWIGNIDPSDSETHYARKFQGRATLTVDKYSDTAFLELRSLTSDDTAVYYCAGTDLAYWGRGAPVTVSS | 177 |

TABLE 11

$EC_{50}$ values for CD47 binding by humanized anti-CD47 mAbs in an ELISA assay

| mAh ID | EC50 (nM) |
|---|---|
| KH1L1 | 1.17 |
| KH1L2 | 0.64 |
| KH1L3 | 0.76 |
| KH2L1 | 0.19 |
| KH2L2 | 0.18 |
| KH2L3 | 0.09 |
| KH3L1 | 0.09 |
| KH3L2 | 0.08 |
| KH3L3 | 0.18 |
| KH3L4 | 0.08 |

KH1L1 refers to the mAb with the KH1 heavy chain variable region and the L1 light chain variable region; all the other humanized mAbs in the table adopt the same naming rule.

Example 7: Expression and Purification of Bispecific Antibodies Carrying a Common Light Chain As mentioned above, DLL3 is detectable on the surface of small cell lung cancer (SCLC) and large cell neuroendocrine carcinoma (LCNEC) tumor cells (Saunders et al., Sci Transl Med 7(302):302ra136 (2015) and Sharma et al., Cancer Res 77(14):3931-41 (2017)). Further, CD47 which mediates the "don't eat me" signal is overexpressed in many tumors such as SCLC (Weiskopf et al., J Clin Invest 126(7):2610-2620 (2016)). A bispecific antibody with one arm binding to CD47 and the other arm binding to DLL3 (termed anti-CD47/DLL3 bispecific antibody) can be used to selectively target a cell that expresses both antigens. Binding of the bispecific antibody to both antigens on the same cell can result in increased affinity compared with either arm due to avidity. The bispecific antibody is expected to have weaker activity against cells that express only CD47 (but not DLL3) due to lack of avidity. This helps avoid targeting normal cells that express certain levels of CD47 by the bispecific antibody and increase its safety and/or tolerability. An anti-CD47/DLL3 bispecific antibody can selectively block the CD47/SIRPα interaction on a cell that express both CD47 and DLL3 and activate the innate immune system against the cell, such as a cancer cell. Thus, an anti-CD47/DLL3 bispecific antibody can be an effective therapy for SCLC, LCNEC and other tumors that express significant levels of both CD47 and DLL3 on the cell surface.

A bispecific antibody against CD47 and DLL3 was constructed with the humanized heavy chain variable region H1 in Table 7, the humanized heavy chain variable region KH2 in Table 10, and the humanized light chain variable region L2 in Table 8. The CDR regions for the bispecific mAb KH2/H1/L2 are provided in Table 12 and Table 13. The VH and VL regions of the bispecific antibody were fused to the constant regions of IgG1 heavy chain and kappa light chain, respectively. The HC containing KH2 has the T366W mutation to form a "knob" and the HC containing H1 has the mutations T366S, L368A, and Y407V to form a "hole", so that the two heavy chains were favored to form a bispecific antibody with heterodimeric HCs (KH2/H1) rather than homodimeric HCs (KH2/KH2 or H1/H1). The resulting bispecific antibody (KH2/H1/L2), termed BA1, was further modified by introducing a S354C cysteine mutation on the anti-CD47 HC (KH2) and a Y349C cysteine mutation on the anti-DLL3 HC (H1) to stabilize the heterodimeric pairing of the heavy chains KH2 and H1 (Merchant et al. Nat. Biotechnol. 16(7):677-81 (1998)). The resulting bispecific antibody was termed BA1(C). The variable regions of BA1 were also fused to the IgG4 frame work with the same cysteine mutations in BA1(C) to produce a bispecific antibody termed BA4(C). The simultaneous expression of the two heavy chains and the light chain in the same cell led to the expression and assembly of a desired bispecific antibody, which contains the anti-CD47 arm and the anti-DLL3 arm. Different ratios of the heavy chain DNAs were used to optimize the expression. The bispecific antibodies were produced in the suspension of ExpiCHO-S cells and purified using Protein A affinity and ion exchange chromatography.

TABLE 12

CDR regions 1-3 of the heavy chains and the common light chain for the bispecific antibodies

| | CDR1 (SEQ ID NO:) | CDR2 (SEQ ID NO:) | CDR3 (SEQ ID NO:) |
|---|---|---|---|
| KH2 | GYTFTSYW (178) | IDPSDSET (179) | AGTDLAY (180) |
| H1 | GYTFTSYV (181) | INPYNDAT (182) | ARGGYDYDGDY (183) |
| L2 | QNINVW (184) | KAS (185) | QQGQSYPFT (186) |

The CDRs were determined utilizing the IMGT method.

TABLE 13

CDR regions 1-3 of the heavy chains and the common light chain for the bispecific antibodies

| | CDR1 (SEQ ID NO:) | CDR2 (SEQ ID NO:) | CDR3 (SEQ ID NO:) |
|---|---|---|---|
| KH2 | SYWMH (187) | NIDPSDSETHYAQKFQG (188) | TDLAY (189) |
| H1 | SYVMH (190) | YINPYNDATKYARKFQG (191) | GGYDYDGDY (192) |
| L2 | HASQNINVWLS (193) | KASNLHT (194) | QQGQSYPFT (195) |

The HC and LC CDRs were determined utilizing the Kabat method.

Example 8: Characterization of Bispecific Antibodies

Figure 4A:
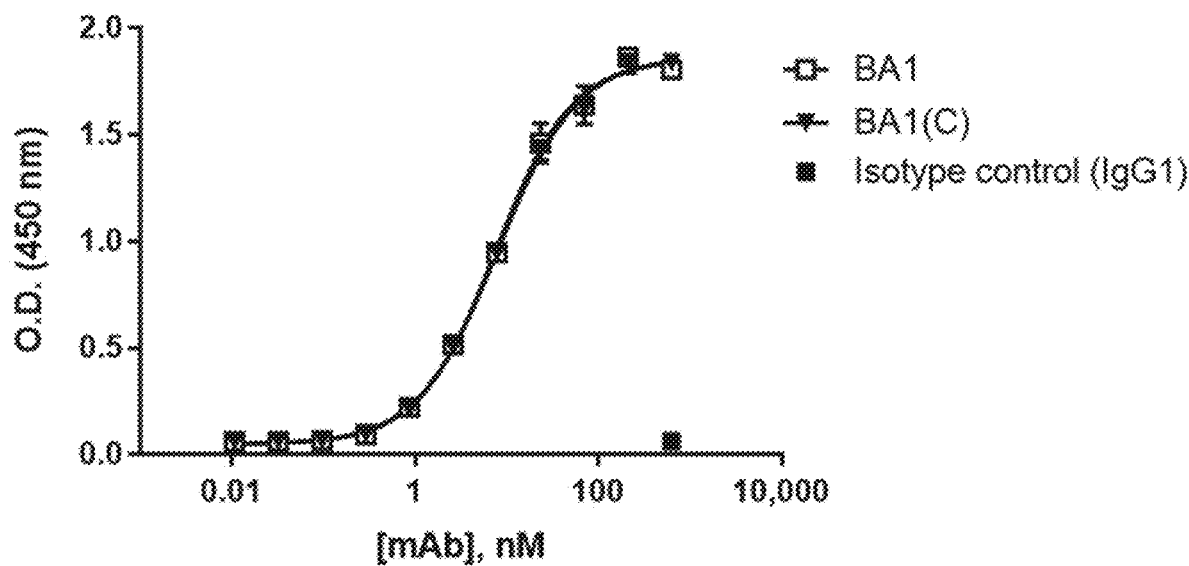
FIGS. 4A-4B show the bridging ELISA data of the bispecific antibodies BA1 and BA1(C) (FIG. 4A) and BA4 (C) (FIG. 4B).
Figure 4B:
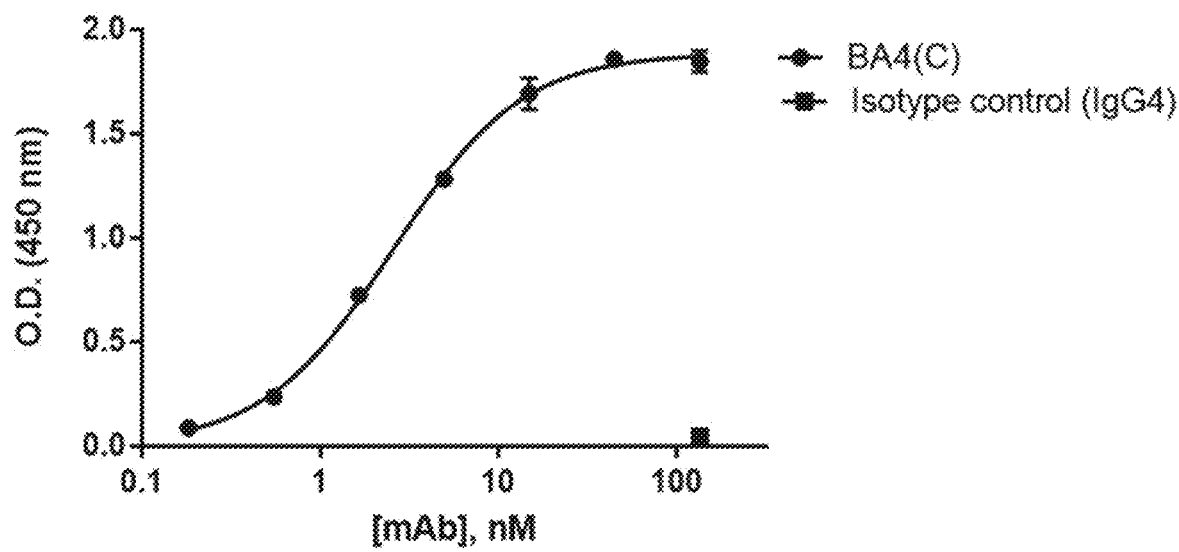

The purified bispecific antibodies were analyzed in a bridging ELISA assay to demonstrate that a bispecific antibody can bind both antigens at the same time. Human FLAG-huDLL3 in carbonate coating buffer (50 μL/well at 0.25 μg/mL) was coated on a 96-well ELISA plate for 1 hour at room temperature. The plate was blocked by 5% BSA in TBST for 1 hour at room temperature. In each well of the plate, a bispecific mAb (50 μL/well at various concentrations) was added and incubated for 1 hour at room temperature. After washing, biotinylated human CD47 extracellular domain (ECD) (AcroBio, Cat #: CD7-H82E9) was added to each well (50 μL/well at 0.05 μg/mL) and incubated at room temperature for 60 minutes. The plate was washed and the binding of biotinylated CD47 to the immobilized bispecific antibody was detected by adding horseradish peroxidase-conjugated streptavidin (JIR, Cat #: 016-030-084) and incubating at room temperature for 60 minutes. Then, after washing, the ELISA was developed using One-step Detection Solution (ThermoFisher Scientific, Cat #: 34028) and measured as the absorbance at 450 nm. The results of the bridging ELISA assay for the bispecific antibodies BA1 and BA1(C) are provided in FIG. 4A; the result of the bridging ELISA assay for BA4(C) is provided in FIG. 4B.

Figure 5:
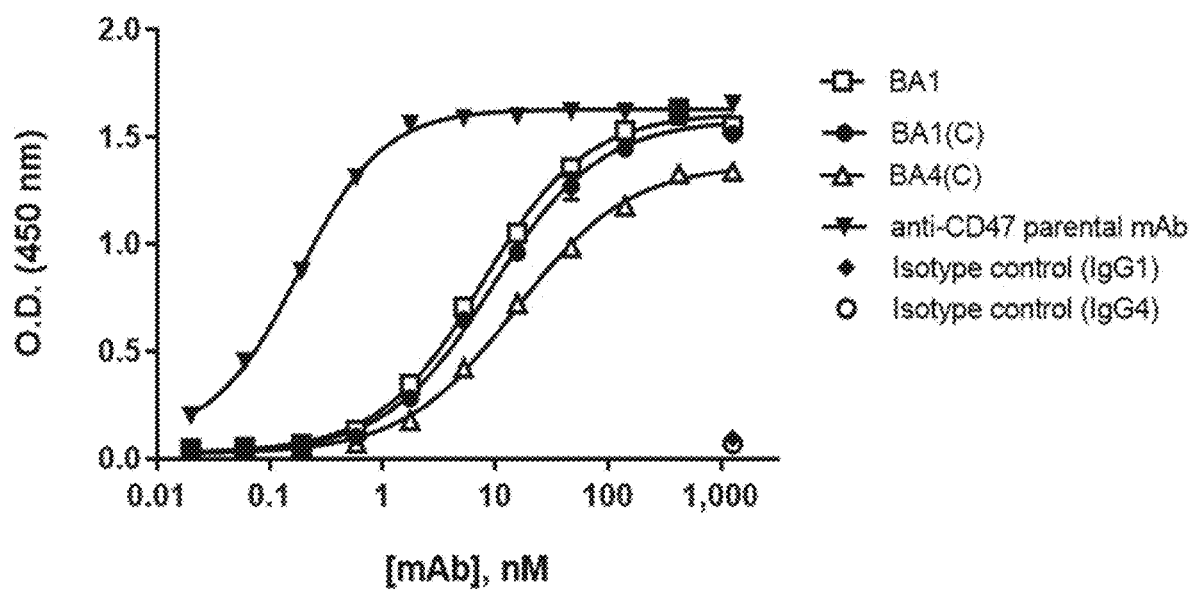
FIG. 5 shows the binding of the bispecific antibodies BA1, BA1(C) and BA4(C) to immobilized CD47 by ELISA assay.
Figure 6A:
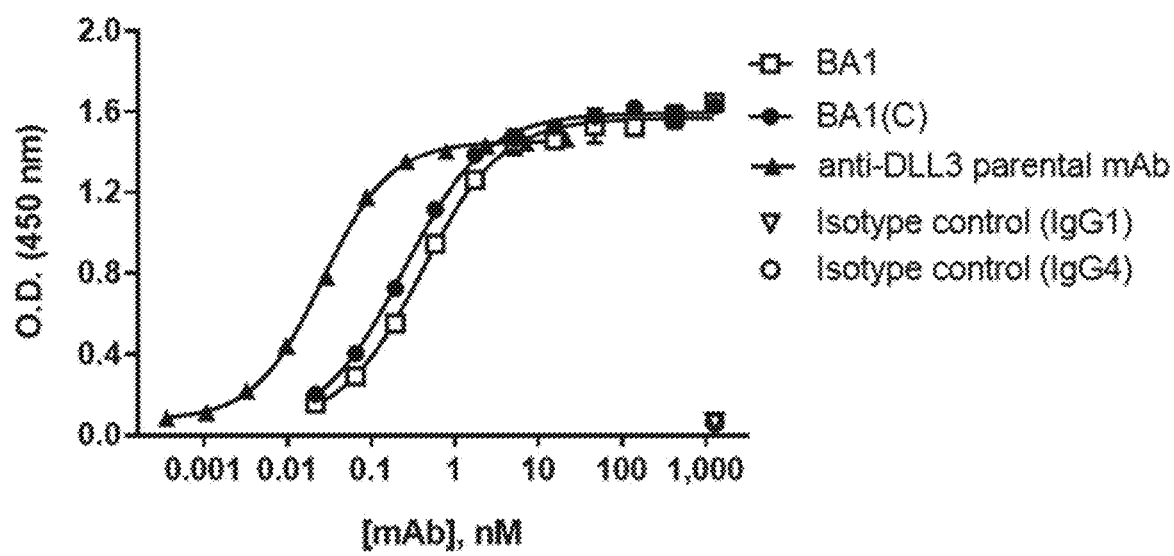
FIGS. 6A-6B show the binding of the bispecific antibodies BA1 and BA1(C) (FIG. 6A) and BA4(C) (FIG. 6B) to immobilized DLL3 by ELISA assay.
Figure 6B:
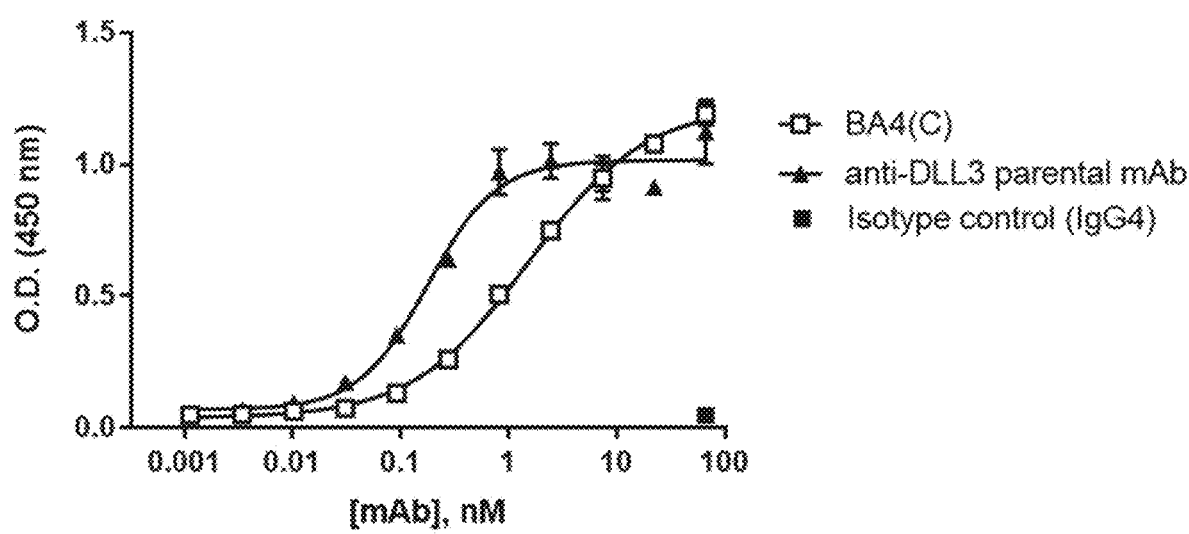

The bispecific antibodies were analyzed for their ability to bind CD47(ECD) or DLL3(ECD)-6His (R&D, Cat #: 9749-DL-050) immobilized on regular or nickel-coated plates in an ELISA assay. The results of the CD47 binding assay for the bispecific antibodies BA1, BA1(C), and BA4C are provided in FIG. 5 (CD47(ECD) was coated on regular plates). The anti-CD47 parental mAb KH2L2 (labeled as anti-CD47 parental mAb in the FIG.) on the IgG4 framework was used as a control. The results of the DLL3 binding assay for the bispecific antibodies BA1 and BA1(C) are provided in FIG. 6A (DLL3(ECD)-6His was coated on a regular plate); the result of the DLL3 binding assay for BA4(C) is provided in FIG. 6B (DLL3(ECD)-6His was immobilized on a nickel-coated plate). The anti-DLL3 parental mAb H1L2 (labeled as anti-DLL3 parental mAb in the FIG.) on the IgG4 framework was used as a control. The results in FIG. 5 indicated that the bispecific antibodies, which have one anti-CD47 arm, were capable of binding CD47, but at a lower affinity than the parental mAb KH2L2 which has two anti-CD47 arms (FIG. 5). Similarly, the results in FIGS. 6A and 6B demonstrated that the bispecific antibodies, which have one anti-DLL3 arm, had weaker binding to DLL3 when compared with the parental anti-DLL3 mAb H1L2 which has two anti-DLL3 arms.

Figure 7:
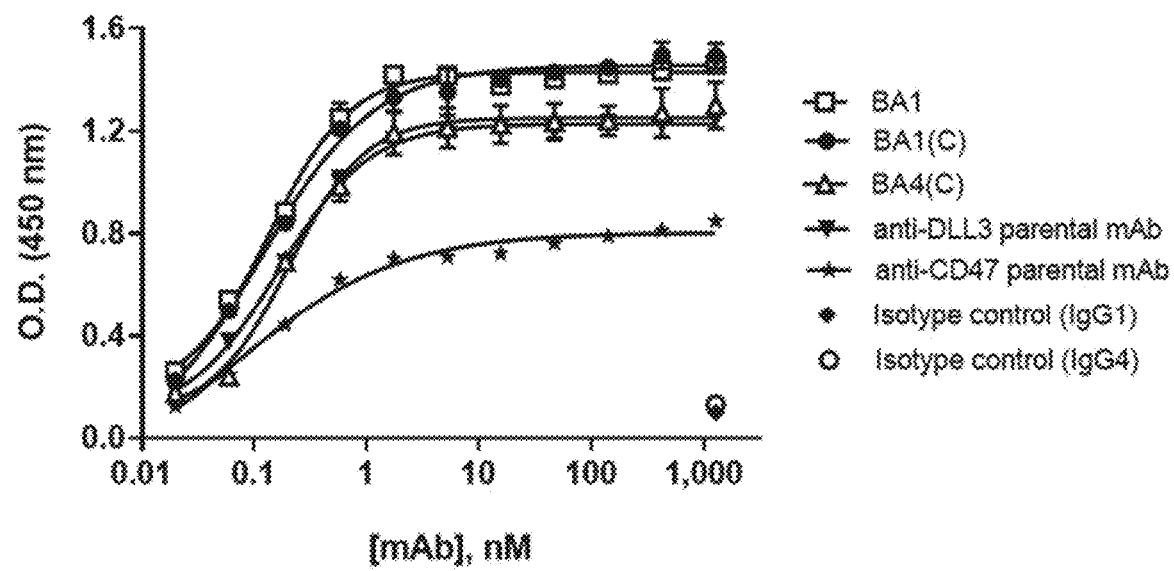
FIG. 7 shows the binding of the bispecific antibodies BA1, BA1(C) and BA4(C) to simultaneously immobilized CD47 and DLL3 in a 1:1 concentration ratio by ELISA assay.

The bispecific antibodies were analyzed for their ability to bind both CD47(ECD) and DLL3(ECD)-6His when they were simultaneously immobilized on the same plate (50 μL/well at 20 nM for both antigens). The results of the CD47/DLL3 binding assay for the bispecific antibodies BA1, BA1(C) and BA4(C) are provided in FIG. 7.

Figure 8A:
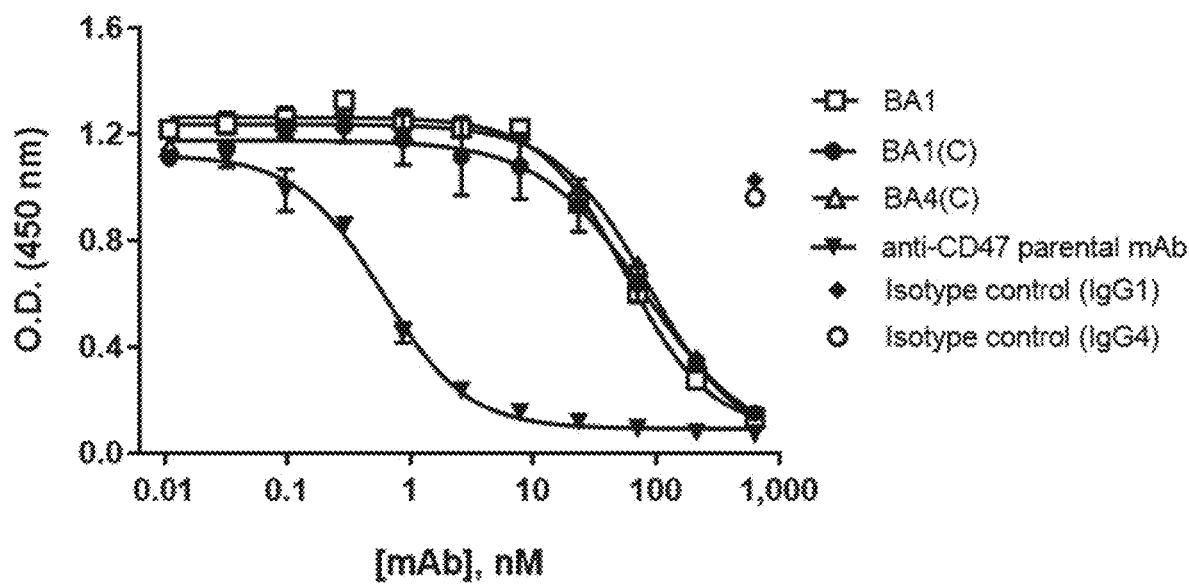
FIGS. 8A-8B show the activity of the bispecific antibodies BA1, BA1(C) and BA4(C) in blocking the CD47/SIRPα interaction in an ELISA assay. Only CD47 was immobilized in the assay in FIG. 8A and both CD47 and DLL3 were immobilized in a 2:1 concentration ratio in the assay in FIG. 8B.
Figure 8B:
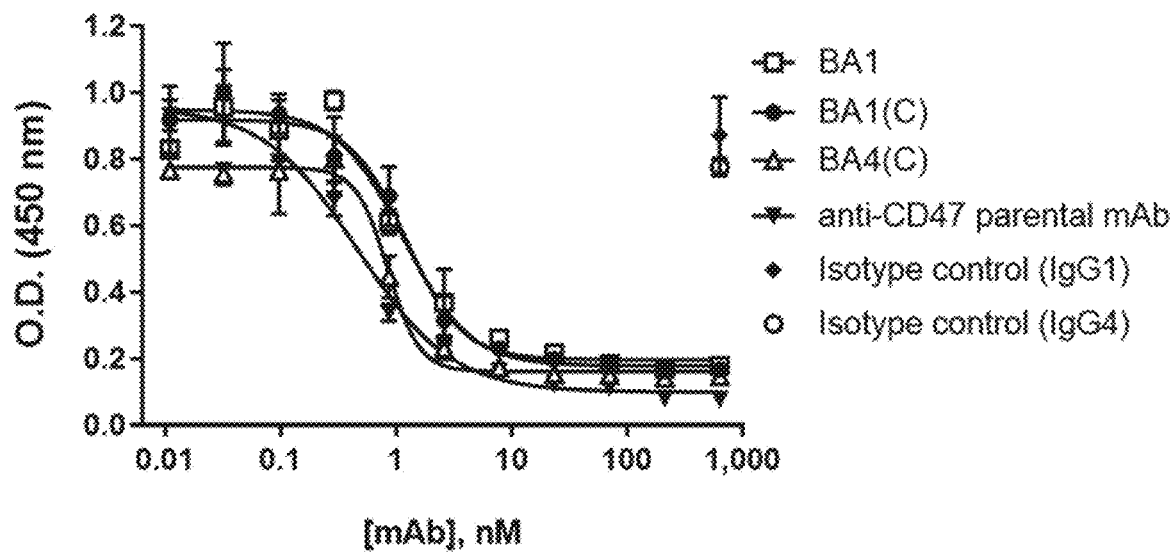

The bispecific antibodies were also analyzed for their ability to block the CD47/SIRPα interaction in an ELISA assay. Human CD47 (ECD) (AcroBio, Cat #: CD7-HA2E9-50 ug) at 1 μg/mL in carbonate coating buffer was coated on a 96-well plate (50 μL/well) at 4° C. overnight. The plate was blocked by 5% BSA in TBST for 1 hour at room temperature. A bispecific and parental mAb at various concentrations were added to the plate and incubated at room temperature for 30 minutes. SIRPα extracellular domain (ECD) fused to mouse Fc (AcroBio, Cat #: SIA-H52A8-100 ug) was added to each well (50 μL/well at 1 μg/mL) and incubated at room temperature for 1 hour. The plate was washed and the binding of SIRPα to the immobilized CD47 was detected by anti-mouse IgG conjugated to horseradish peroxidase (mIgG-HRP) (ThermoFisher Scientific, Cat #: A16084) with incubation for 1 hour at room temperature. Then after washing, the ELISA was developed using One-step Detection Solution (ThermoFisher Scientific, Cat #: 34028) and measured as the absorbance at 450 nm. Consistent with the data from the CD47 binding assay on ELISA, the bispecific Abs have reduced ability to block the CD47/SIRPα interaction in this context (FIG. 8A). The assay was also carried out when both CD47(ECD) and DLL3(ECD)-6His were simultaneously immobilized on the same plate at a CD47:DLL3 ratio of 2:1 (50 µL/well with CD47 at 40 nM and DLL3 at 20 nM) for 1 hour at room temperature and the plate was blocked by 5% BSA in DPBS. Under such a condition, the bispecific Abs have similar ability to block the CD47/SIRPα interaction when compared with the anti-CD47 parental mAb (FIG. 8B), suggesting that binding to the immobilized DLL3 on the plate by the anti-DLL3 arm of each of the bispecific Abs contributes to the blockade of the CD47/SIRPα interaction.

Figure 9:
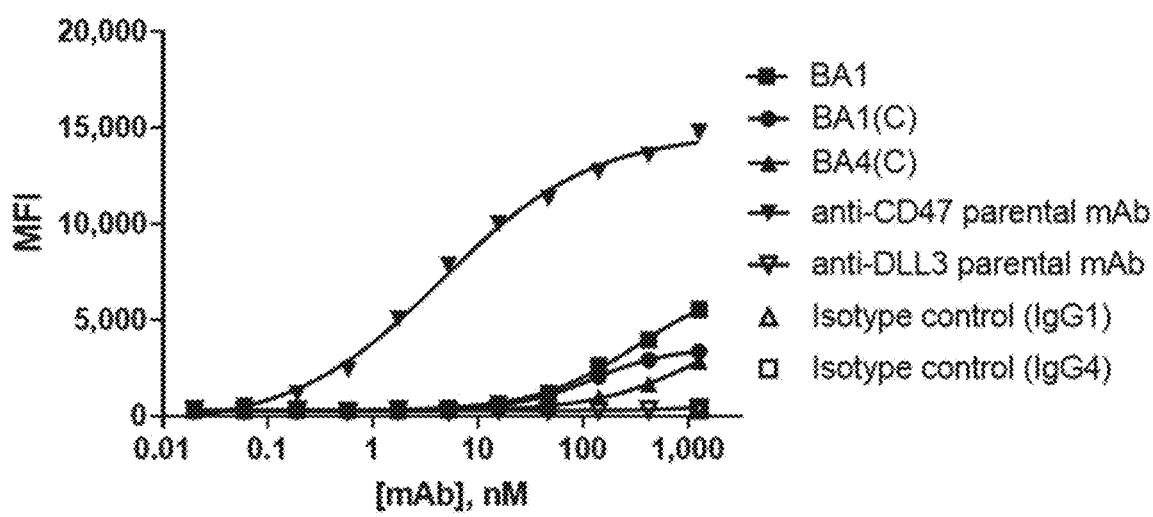
FIG. 9 shows the binding of the bispecific antibodies BA1, BA1(C) and BA4(C) to Raji cells.

The bispecific antibodies were analyzed for their ability to bind Raji cells which have no detectable DLL3 expression. Raji cells (14,000 cells per well on a 96-well plate) were incubated with either a solution of a purified mAb at various concentrations or an isotype control in Hanks' Balanced Salt Solution (HBSS) containing 0.05% sodium azide and 0.1% BSA at room temperature for 30 minutes. After incubation, the plates were washed three times with the same buffer. Using a PE-Cy7-conjugated anti-human IgG secondary antibody, the presence of the mAb on Raji cells was measured by FACS (Attune NxT; ThermoFisher, Carlsbad, CA). The result of the FACS binding analysis is provided in FIG. 9.

Figure 10:
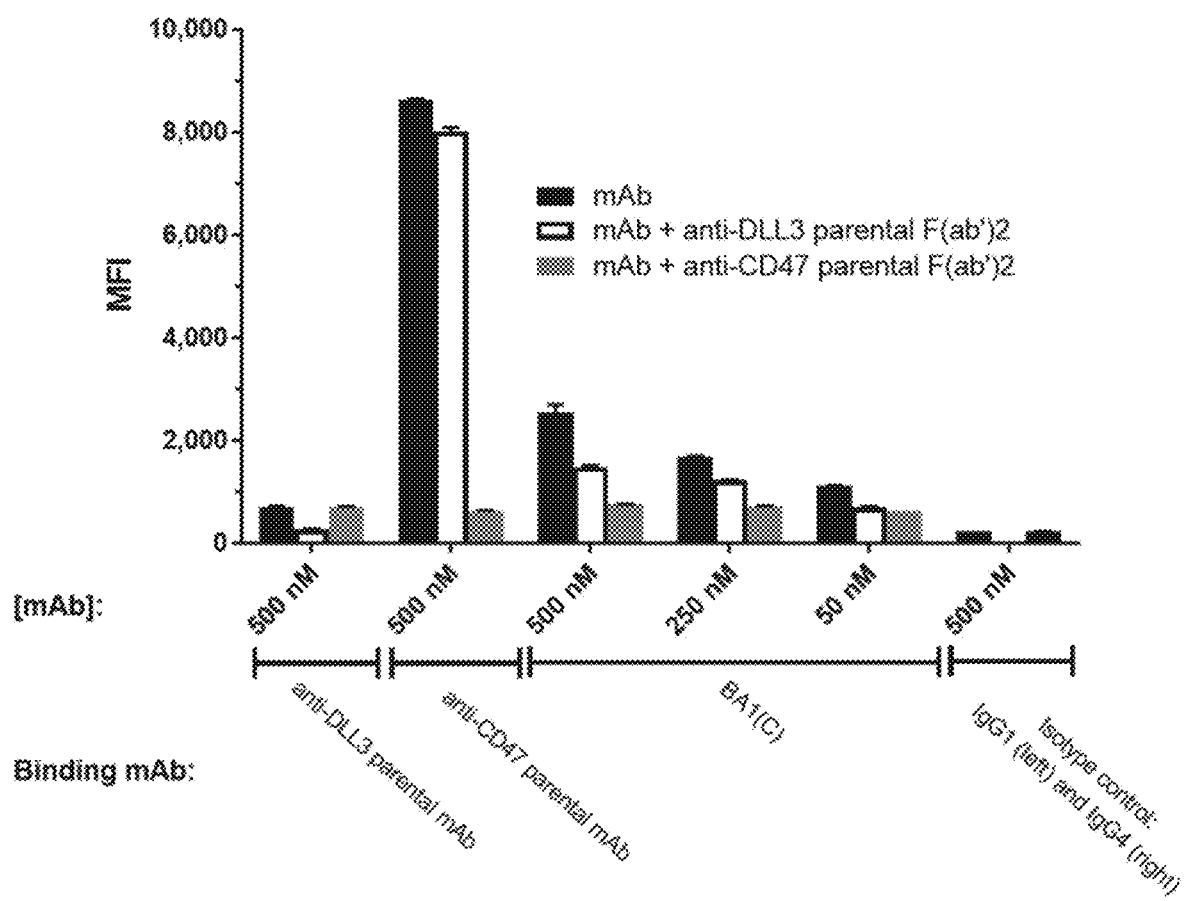
FIG. 10 shows the inhibitory effect of the anti-CD47 or anti-DLL3 F(ab')2 on the binding of the bispecific antibody BA1(C) to SHP-77 cells.

The binding of the bispecific mAb BA1(C) and the two parental control mAbs to SHP-77 cells were tested in the presence or absence of one of the competing F(ab')2's: anti-DLL3 parental F(ab')2 (final concentration in the assay was 25 µM) and anti-CD47 parental F(ab')2 (final concentration in the assay was 10 µM). F(ab')2's were generated from mAbs using immobilized pepsin (Thermo Fisher Scientific, Cat: #20343) according to the instruction and purified. The result of the binding analysis is provided in FIG. 10. Inhibition of the binding of BA1(C) to SHP-77 cells by both F(ab')2's indicates that both the anti-CD47 and anti-DLL3 arms of the bispecific antibody contribute to its binding to SHP-77 cells.

Figure 11A:
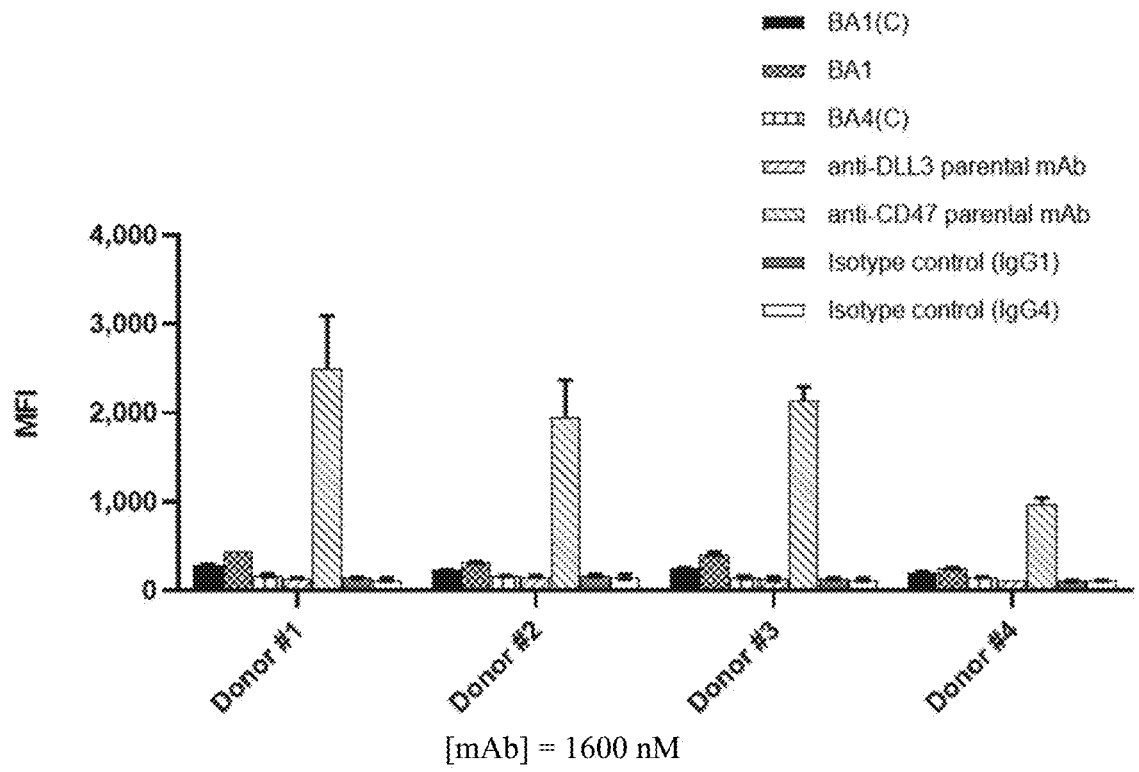
FIGS. 11A-11C show the binding of the bispecific antibodies to human red blood cells (RBCs) at different mAb concentrations (1,600 nM (FIG. 11A), 533 nM (FIG. 11B), and 178 nM (FIG. 11C)).
Figure 11B:
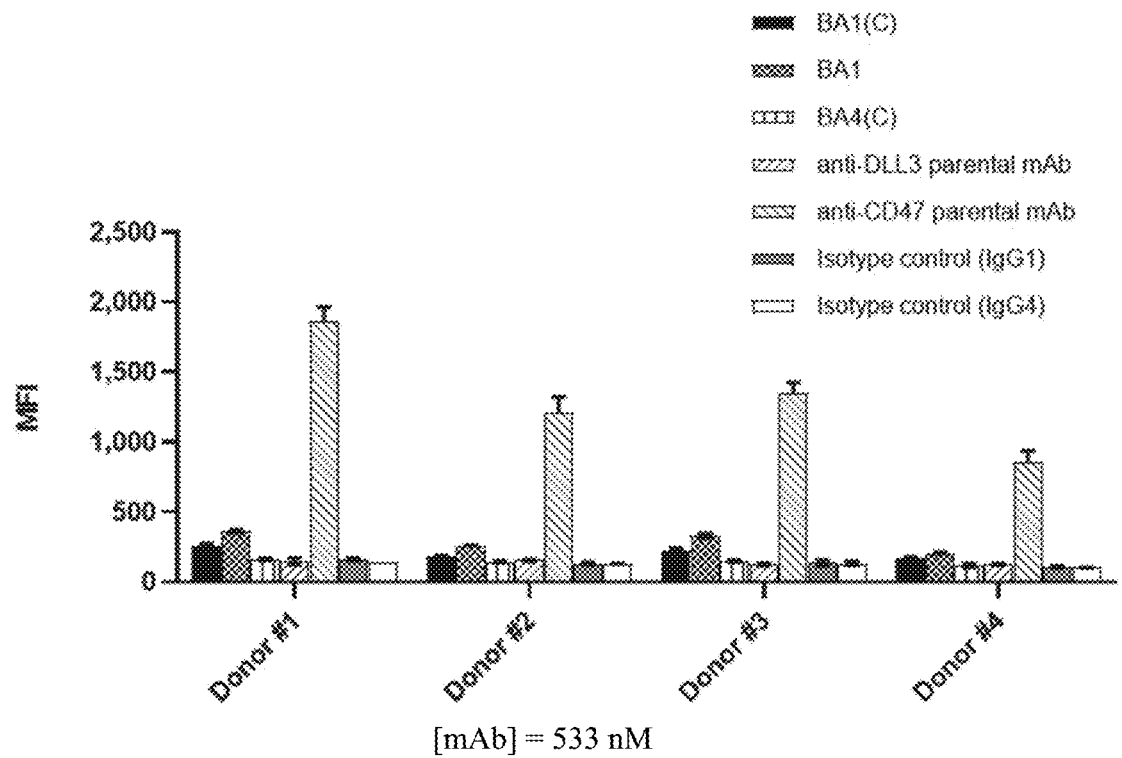
Figure 11C:
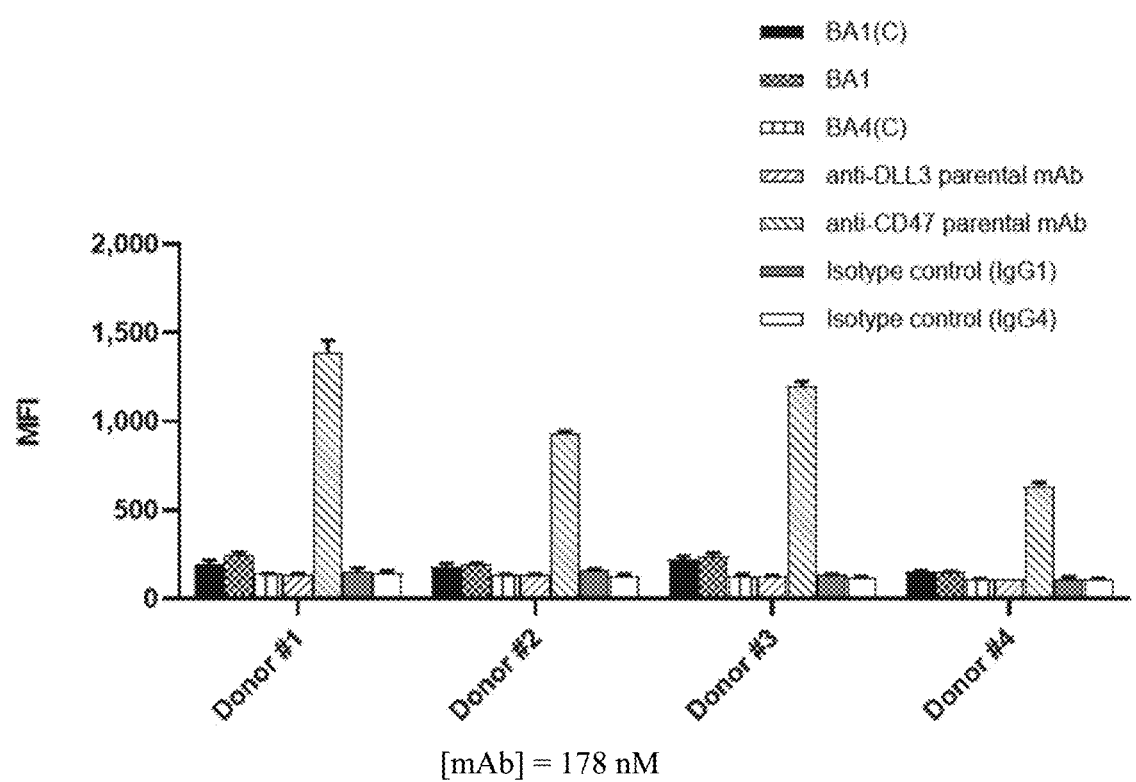

The bispecific antibodies were tested for their ability to bind to human and cynomolgus red blood cells (RBCs). 14,000 RBCs were resuspended into 20 µL FACS buffer (1×HBSS (Thermo Fisher Scientific, Cat #: 14175079) with 0.1% BSA and 0.05% sodium azide) containing diluted mAbs and incubated at room temperature for 30 minutes. After incubation, the plates were washed three times with FACS buffer and the cells were resuspended with PE-Cy7 conjugated anti-human IgG-Fc secondary antibody (BioLegend, Cat #: 409316) and incubated for 15 minutes at room temperature in dark. Plates were washed 2× with FACS buffer. Cells were resuspended and transferred to a 384-well plate for analysis with Attune NxT Flow Cytometer. FIGS. 11A-11C show the binding of the bispecific antibodies to human red blood cells (RBCs) at the following mAb concentrations: 1,600 nM (FIG. 11A), 533 nM (FIG. 11B), and 178 nM (FIG. 11C). Anti-CD47 and anti-DLL3 parental antibodies and IgG1 and IgG4 isotypes were used as controls.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated anti-DLL3 monoclonal antibody or antigen-binding fragment thereof comprising a heavy chain complementarity determining region 1 (HCDR1), HCDR2, and HCDR3, and a light chain complementarity determining region 1 (LCDR1), LCDR2, and LCDR3, having the polypeptide sequences of:
   (a) SEQ ID NOs: 25, 26, 27, 61, 62 and 63, respectively, or SEQ ID NOs: 97, 98, 99, 133, 134 and 135, respectively;
   (b) SEQ ID NOs: 40, 41, 42, 76, 77 and 78, respectively, or SEQ ID NOs: 112, 113, 114, 148, 149 and 150, respectively;
   (c) SEQ ID NOs: 46, 47, 48, 82, 83 and 84, respectively, or SEQ ID NOs: 118, 119, 120, 154, 155 and 156, respectively;
   (d) SEQ ID NOs: 52, 53, 54, 88, 89 and 90, respectively, or SEQ ID NOs: 124, 125, 126, 160, 161 and 162, respectively;
   (e) SEQ ID NOs: 58, 59, 60, 94, 95 and 96, respectively, or SEQ ID NOs: 130, 131, 132, 166, 167 and 168, respectively;
   wherein the antibody or antigen-binding fragment thereof specifically binds DLL3.

2. The isolated anti-DLL3 monoclonal antibody or antigen-binding fragment thereof of claim 1, comprising a heavy chain variable region having a polypeptide sequence at least 95% identical to SEQ ID NO:170, 1, 11, 15, 19, or 23, or a light chain variable region having a polypeptide sequence at least 95% identical to SEQ ID NO:172, 2, 12, 16, 20, 24, 171, or 173.

3. The isolated anti-DLL3 monoclonal antibody or antigen-binding fragment thereof of claim 1, comprising:
   (a) a heavy chain variable region having the polypeptide sequence of SEQ ID NO:170, and a light chain variable region having the polypeptide sequence of SEQ ID NO:172;
   (b) a heavy chain variable region having the polypeptide sequence of SEQ ID NO:1, and a light chain variable region having the polypeptide sequence of SEQ ID NO:2;
   (c) a heavy chain variable region having the polypeptide sequence of SEQ ID NO:11, and a light chain variable region having the polypeptide sequence of SEQ ID NO:12;
   (d) a heavy chain variable region having the polypeptide sequence of SEQ ID NO:15, and a light chain variable region having the polypeptide sequence of SEQ ID NO:16;
   (e) a heavy chain variable region having the polypeptide sequence of SEQ ID NO:19, and a light chain variable region having the polypeptide sequence of SEQ ID NO:20;
   (f) a heavy chain variable region having the polypeptide sequence of SEQ ID NO:23, and a light chain variable region having the polypeptide sequence of SEQ ID NO:24;
   (g) a heavy chain variable region having the polypeptide sequence of SEQ ID NO:170, and a light chain variable region having the polypeptide sequence of SEQ ID NO:171; or
   (h) a heavy chain variable region having the polypeptide sequence of SEQ ID NO:170, and a light chain variable region having the polypeptide sequence of SEQ ID NO:173.

4. The isolated anti-DLL3 monoclonal antibody or antigen-binding fragment thereof of claim 1, wherein the monoclonal antibody or antigen-binding fragment thereof is chimeric or humanized.

5. The isolated anti-DLL3 monoclonal antibody or antigen-binding fragment thereof of claim 1, wherein the monoclonal antibody or antigen-binding fragment thereof is capable of inducing effector-mediated tumor cell lysis, mediating the recruitment of conjugated drugs, and/or forming a bispecific antibody.

6. A pharmaceutical composition, comprising the isolated anti-DLL3 monoclonal antibody or antigen-binding fragment thereof of claim 1 and a pharmaceutically acceptable carrier.

7. A method of determining a level of DLL3 in a subject, the method comprising:
   (a) obtaining a sample from the subject;
   (b) contacting the sample with an isolated anti-DLL3 monoclonal antibody or antigen-binding fragment thereof of claim 1; and
   (c) determining a level of DLL3 in the subject.

8. The method of claim 7, wherein the sample is a tissue sample or a blood sample.

9. The method of claim 8, wherein the tissue sample is a cancer tissue sample.

* * * * *

SEQUENCE LISTING

```
<160> NUMBER OF SEQ ID NOS: 195

<210> SEQ ID NO 1
<211> LENGTH: 118
<212> TYPE: PRT
<213> ORGANISM: Artificial Sequence
<220> FEATURE:
<223> OTHER INFORMATION: 13P9A Heavy Chain Variable Region

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Pro Asp Trp Ile
        35                  40                  45

Gly Tyr Ile Asn Pro Tyr Asn Asp Ala Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Gly Tyr Asp Tyr Asp Gly Asp Tyr Trp Gly Gln Gly Thr
            100                 105                 110

Thr Leu Thr Val Ser Ser
        115

<210> SEQ ID NO 2
```

```
<211> LENGTH: 107
<212> TYPE: PRT
<213> ORGANISM: Artificial Sequence
<220> FEATURE:
<223> OTHER INFORMATION: 13P9A Light Chain Variable Region

<400> SEQUENCE: 2

Asp Ile Gln Met Asn Gln Ser Pro Ser Ser Leu Ser Ala Ser Leu Gly
1               5                   10                  15

Asp Ser Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Phe
                85                  90                  95

Thr Phe Gly Ser Gly Thr Lys Leu Glu Ile Lys
            100                 105

<210> SEQ ID NO 3
<211> LENGTH: 122
<212> TYPE: PRT
<213> ORGANISM: Artificial Sequence
<220> FEATURE:
<223> OTHER INFORMATION: 5A16A Heavy Chain Variable Region

<400> SEQUENCE: 3

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Arg Tyr
            20                  25                  30

Ile Leu His Trp Val Lys Leu Lys Pro Gly Gln Gly Leu Glu Trp Ile
        35                  40                  45

Gly Tyr Ile Asn Pro Tyr Asn Asp Gly Thr Lys Tyr Asn Glu Lys Phe
50                  55                  60

Lys Gly Lys Ala Thr Leu Thr Ser Asp Lys Ser Ser Ser Thr Ala Tyr
65                  70                  75                  80

Met Glu Leu Ser Arg Leu Thr Ser Tyr Asp Ser Ala Val Tyr Tyr Cys
                85                  90                  95

Ala Arg Asp Ser Ser Gly Tyr Gly Gly Ala Tyr Ala Met Asp Phe Trp
            100                 105                 110

Gly Gln Gly Thr Ser Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: 5A16A Light Chain Variable Region

<400> SEQUENCE: 4

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30
```

```
Leu Ala Trp Tyr Gln Gln Lys Gln Gly Arg Ser Pro Gln Leu Leu Val
        35                  40                  45

Tyr Asn Ala Lys Thr Leu Pro Tyr Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Thr Thr Pro Trp
                 85                  90                  95

Thr Phe Gly Gly Gly Thr Lys Leu Glu Ile Lys
            100                 105
```

<210> SEQ ID NO 5
<211> LENGTH: 120
<212> TYPE: PRT
<213> ORGANISM: Artificial Sequence
<220> FEATURE:
<223> OTHER INFORMATION: 14L22A Heavy Chain Variable Region

<400> SEQUENCE: 5

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Ala Ile Asn Ser Asn Gly Gly Asn Thr Tyr Tyr Pro Asp Thr Val
 50                  55                  60

Lys Asp Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Arg His Arg Gly Gly Phe Tyr Tyr Ala Val Asp Tyr Trp Gly Gln
            100                 105                 110

Gly Thr Ser Val Thr Val Ser Ser
            115                 120
```

<210> SEQ ID NO 6
<211> LENGTH: 112
<212> TYPE: PRT
<213> ORGANISM: Artificial Sequence
<220> FEATURE:
<223> OTHER INFORMATION: 14L22A Light Chain Variable Region

<400> SEQUENCE: 6

```
Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Arg Thr Phe Gly Gly Gly Thr Lys Leu Glu Ile Lys
            100                 105                 110
```

```
<210> SEQ ID NO 7
<211> LENGTH: 116
<212> TYPE: PRT
<213> ORGANISM: Artificial Sequence
<220> FEATURE:
<223> OTHER INFORMATION: 10P18A Heavy Chain Variable Region

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile Asp Trp Val Lys Gln Ser Pro Gly Lys Ser Leu Glu Trp Ile
        35                  40                  45

Gly Tyr Ile Tyr Pro Ser Asn Gly Glu Thr Ser Tyr Asn Gln Lys Phe
    50                  55                  60

Lys Gly Lys Ala Thr Leu Thr Val Asp Lys Ser Ser Ser Thr Val Asn
65                  70                  75                  80

Met Gln Leu Asn Ser Leu Thr Ser Glu Asp Ser Ala Val Tyr Tyr Cys
                85                  90                  95

Ala Arg Glu Ser Tyr Ala Met Asp Tyr Trp Gly Gln Gly Thr Ser Val
            100                 105                 110

Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: 10P18A Light Chain Variable Region

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 9
<211> LENGTH: 119
<212> TYPE: PRT
<213> ORGANISM: Artificial Sequence
<220> FEATURE:
<223> OTHER INFORMATION: 13P11A Heavy Chain Variable Region

<400> SEQUENCE: 9

Asp Val Gln Leu Gln Glu Ser Gly Pro Gly Leu Val Lys Pro Ser Gln
1               5                   10                  15
```

```
Thr Val Ser Leu Thr Cys Thr Val Thr Gly Tyr Ser Ile Thr Asn Gly
            20                  25                  30

Asn His Trp Trp Ser Trp Ile Arg Gln Val Ser Gly Lys Leu Glu
        35                  40                  45

Trp Met Gly Tyr Ile Ser Ser Gly Ser Thr Asp Ser Asn Pro Ser
        50                  55                  60

Leu Lys Ser Arg Ile Ser Ile Thr Arg Asp Thr Ser Lys Asn Gln Leu
65                  70                  75                  80

Phe Leu His Leu Asn Ser Val Thr Thr Glu Asp Ile Ala Thr Tyr Tyr
                85                  90                  95

Cys Ala Thr Thr Gly Thr Trp Gly Tyr Phe Asp Tyr Trp Gly Gln Gly
                100                 105                 110

Thr Thr Leu Thr Val Ser Ser
            115

<210> SEQ ID NO 10
<211> LENGTH: 107
<212> TYPE: PRT
<213> ORGANISM: Artificial Sequence
<220> FEATURE:
<223> OTHER INFORMATION: 13P11A Light Chain Variable Region

<400> SEQUENCE: 10

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
            35                  40                  45

Tyr Gly Ala Ser Asn Arg Phe Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 11
<211> LENGTH: 118
<212> TYPE: PRT
<213> ORGANISM: Artificial Sequence
<220> FEATURE:
<223> OTHER INFORMATION: 3C16A Heavy Chain Variable Region

<400> SEQUENCE: 11

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
            35                  40                  45

Gly Tyr Val Ile Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95
```

Ala Arg Pro Ser Asn Trp Asp Glu Phe Asp Tyr Trp Gly Gln Gly Thr
            100                 105                 110

Thr Leu Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: 3C16A Light Chain Variable Region

<400> SEQUENCE: 12

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys
            100                 105

<210> SEQ ID NO 13
<211> LENGTH: 116
<212> TYPE: PRT
<213> ORGANISM: Artificial Sequence
<220> FEATURE:
<223> OTHER INFORMATION: 3I21A Heavy Chain Variable Region

<400> SEQUENCE: 13

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Lys Phe
    50                  55                  60

Lys Thr Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Tyr Asp Gly Tyr Phe Ala Tyr Trp Gly Gln Gly Thr Leu Val
            100                 105                 110

Thr Val Ser Ala
        115

<210> SEQ ID NO 14
<211> LENGTH: 107
<212> TYPE: PRT
<213> ORGANISM: Artificial Sequence
<220> FEATURE:
<223> OTHER INFORMATION: 3I21A Light Chain Variable Region

<400> SEQUENCE: 14

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Asp Pro Ser Arg Phe Ser Gly
    50                  55                  60

Ser Gly Ser Gly Lys Asp Tyr Thr Leu Ser Ile Thr Ser Leu Gln Ile
65                  70                  75                  80

Glu Asp Val Ala Thr Tyr Tyr Cys Gln Gln Tyr Trp Ser Ile Pro Phe
                85                  90                  95

Thr Phe Gly Ala Gly Thr Lys Leu Glu Leu Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: 8H5A Heavy Chain Variable Region

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Ile Ala Asp Thr Ala Thr Tyr Tyr
                85                  90                  95

Cys Ala Arg Thr Tyr Asp Tyr Asp Glu Tyr Phe Asp Tyr Trp Gly Gln
            100                 105                 110

Gly Thr Thr Leu Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: 8H5A Light Chain Variable Region

<400> SEQUENCE: 16

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

```
Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Phe Thr Phe Gly Ser Gly Thr Lys Leu Glu Ile Lys
            100                 105                 110
```

<210> SEQ ID NO 17
<211> LENGTH: 119
<212> TYPE: PRT
<213> ORGANISM: Artificial Sequence
<220> FEATURE:
<223> OTHER INFORMATION: 15K2A Heavy Chain Variable Region

<400> SEQUENCE: 17

```
Gln Val Gln Leu Gln Gln Pro Gly Ala Glu Leu Val Gln Pro Gly Ala
1               5                   10                  15

Ser Val Lys Leu Ser Cys Lys Ala Ser Gly Tyr Thr Phe Thr Ser Tyr
                20                  25                  30

Trp Met Asn Trp Met Lys Gln Arg Pro Gly Arg Gly Leu Glu Trp Ile
            35                  40                  45

Gly Arg Ile His Pro Ser Asp Ser Glu Thr His Tyr Asn Gln Lys Phe
        50                  55                  60

Arg Thr Lys Ala Thr Leu Thr Val Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Glu Asp Gly Tyr Tyr Trp Tyr Phe Asp Val Trp Gly Ala Gly
            100                 105                 110

Thr Thr Val Thr Val Ser Ser
        115
```

<210> SEQ ID NO 18
<211> LENGTH: 111
<212> TYPE: PRT
<213> ORGANISM: Artificial Sequence
<220> FEATURE:
<223> OTHER INFORMATION: 15K2A Light Chain Variable Region

<400> SEQUENCE: 18

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ile Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys
            100                 105                 110
```

<210> SEQ ID NO 19
<211> LENGTH: 117
<212> TYPE: PRT

<213> ORGANISM: Artificial Sequence
<220> FEATURE:
<223> OTHER INFORMATION: 5A24A Heavy Chain Variable Region

<400> SEQUENCE: 19

Glu Val Gln Leu Gln Gln Ser Gly Ala Glu Leu Val Lys Pro Gly Ala
1               5                   10                  15

Ser Val Lys Ile Pro Cys Lys Ala Ser Gly Tyr Lys Phe Thr Asp Phe
            20                  25                  30

Asn Met Asp Trp Val Lys Gln Ser His Gly Lys Ser Leu Glu Trp Ile
        35                  40                  45

Gly Asp Ile Asn Pro Asn Ser Gly Gly Thr Ile Tyr Asn Gln Lys Phe
50                  55                  60

Lys Gly Lys Ala Thr Leu Thr Val Asp Lys Ser Leu Ser Thr Ala Tyr
65                  70                  75                  80

Met Glu Leu Gly Ser Leu Thr Ser Glu Asp Thr Ala Val Tyr Tyr Cys
                85                  90                  95

Ala Arg Trp Asp Tyr Gly Asn Phe Ala Tyr Trp Gly Gly Thr Leu
            100                 105                 110

Val Thr Val Ser Ala
        115

<210> SEQ ID NO 20
<211> LENGTH: 112
<212> TYPE: PRT
<213> ORGANISM: Artificial Sequence
<220> FEATURE:
<223> OTHER INFORMATION: 5A24A Light Chain Variable Region

<400> SEQUENCE: 20

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Thr Lys Leu Glu Leu Lys
            100                 105                 110

<210> SEQ ID NO 21
<211> LENGTH: 119
<212> TYPE: PRT
<213> ORGANISM: Artificial Sequence
<220> FEATURE:
<223> OTHER INFORMATION: 15P17A Heavy Chain Variable Region

<400> SEQUENCE: 21

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Lys Phe
                50                  55                  60

Lys Ser Lys Ala Thr Leu Thr Val Asp Lys Ser Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Arg Glu Asp Gly Tyr Tyr Trp Tyr Phe Asp Val Trp Gly Ala Gly
            100                 105                 110

Thr Thr Val Thr Val Ser Ser
            115

<210> SEQ ID NO 22
<211> LENGTH: 111
<212> TYPE: PRT
<213> ORGANISM: Artificial Sequence
<220> FEATURE:
<223> OTHER INFORMATION: 15P17A Light Chain Variable Region

<400> SEQUENCE: 22

Asn Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn His
                 85                  90                  95

Glu Asp Pro Trp Thr Phe Gly Gly Gly Thr Lys Leu Glu Ile Lys
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: 15N21A Heavy Chain Variable Region

<400> SEQUENCE: 23

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Ala Met Ser Trp Val Arg Gln Thr Pro Glu Lys Arg Leu Glu Trp Val
         35                  40                  45

Ala Ala Ile Asn Ser Asn Gly Gly Arg Asn Tyr Tyr Pro Asp Thr Val
         50                  55                  60

Lys Asp Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Arg His Arg Gly Gly Tyr Tyr Tyr Ala Met Asp Tyr Trp Gly Gln
            100                 105                 110

Gly Thr Ser Val Thr Val Ser Ser

<210> SEQ ID NO 24
<211> LENGTH: 112
<212> TYPE: PRT
<213> ORGANISM: Artificial Sequence
<220> FEATURE:
<223> OTHER INFORMATION: 15N21A Light Chain Variable Region

<400> SEQUENCE: 24

```
Asp Ile Val Met Ser Gln Ser Pro Ser Ser Leu Ala Val Ser Val Gly
1               5                   10                  15
Glu Lys Val Thr Met Ser Cys Lys Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Tyr Tyr Thr Tyr Leu Thr Phe Gly Ala Gly Thr Lys Leu Glu Leu Lys
            100                 105                 110
```

<210> SEQ ID NO 25
<211> LENGTH: 8
<212> TYPE: PRT
<213> ORGANISM: Artificial Sequence
<220> FEATURE:
<223> OTHER INFORMATION: 13P9A HC CDR1

<400> SEQUENCE: 25

```
Gly Tyr Thr Phe Thr Ser Tyr Val
1               5
```

<210> SEQ ID NO 26
<211> LENGTH: 8
<212> TYPE: PRT
<213> ORGANISM: Artificial Sequence
<220> FEATURE:
<223> OTHER INFORMATION: 13P9A HC CDR2

<400> SEQUENCE: 26

```
Ile Asn Pro Tyr Asn Asp Ala Thr
1               5
```

<210> SEQ ID NO 27
<211> LENGTH: 11
<212> TYPE: PRT
<213> ORGANISM: Artificial Sequence
<220> FEATURE:
<223> OTHER INFORMATION: 13P9A HC CDR3

<400> SEQUENCE: 27

```
Ala Arg Gly Gly Tyr Asp Tyr Asp Gly Asp Tyr
1               5                   10
```

<210> SEQ ID NO 28
<211> LENGTH: 8
<212> TYPE: PRT
<213> ORGANISM: Artificial Sequence
<220> FEATURE:
<223> OTHER INFORMATION: 5A16A HC CDR1

```
<400> SEQUENCE: 28

Gly Tyr Thr Phe Thr Arg Tyr Ile
1               5

<210> SEQ ID NO 29
<211> LENGTH: 8
<212> TYPE: PRT
<213> ORGANISM: Artificial Sequence
<220> FEATURE:
<223> OTHER INFORMATION: 5A16A HC CDR2

<400> SEQUENCE: 29

Ile Asn Pro Tyr Asn Asp Gly Thr
1               5

<210> SEQ ID NO 30
<211> LENGTH: 15
<212> TYPE: PRT
<213> ORGANISM: Artificial Sequence
<220> FEATURE:
<223> OTHER INFORMATION: 5A16A HC CDR3

<400> SEQUENCE: 30

Ala Arg Asp Ser Ser Gly Tyr Gly Gly Ala Tyr Ala Met Asp Phe
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: 14L22A HC CDR1

<400> SEQUENCE: 31

Gly Phe Thr Phe Ser Ser Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: 14L22A HC CDR2

<400> SEQUENCE: 32

Ile Asn Ser Asn Gly Gly Asn Thr
1               5

<210> SEQ ID NO 33
<211> LENGTH: 13
<212> TYPE: PRT
<213> ORGANISM: Artificial Sequence
<220> FEATURE:
<223> OTHER INFORMATION: 14L22A HC CDR3

<400> SEQUENCE: 33

Ala Arg His Arg Gly Gly Phe Tyr Tyr Ala Val Asp Tyr
1               5                   10

<210> SEQ ID NO 34
<211> LENGTH: 8
<212> TYPE: PRT
<213> ORGANISM: Artificial Sequence
<220> FEATURE:
<223> OTHER INFORMATION: 10P18A HC CDR1
```

```
<400> SEQUENCE: 34

Gly Tyr Ser Phe Thr Gly Tyr Tyr
1               5

<210> SEQ ID NO 35
<211> LENGTH: 8
<212> TYPE: PRT
<213> ORGANISM: Artificial Sequence
<220> FEATURE:
<223> OTHER INFORMATION: 10P18A HC CDR2

<400> SEQUENCE: 35

Ile Tyr Pro Ser Asn Gly Glu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: 10P18A HC CDR3

<400> SEQUENCE: 36

Ala Arg Glu Ser Tyr Ala Met Asp Tyr
1               5

<210> SEQ ID NO 37
<211> LENGTH: 10
<212> TYPE: PRT
<213> ORGANISM: Artificial Sequence
<220> FEATURE:
<223> OTHER INFORMATION: 13P11A HC CDR1

<400> SEQUENCE: 37

Gly Tyr Ser Ile Thr Asn Gly Asn His Trp
1               5                   10

<210> SEQ ID NO 38
<211> LENGTH: 7
<212> TYPE: PRT
<213> ORGANISM: Artificial Sequence
<220> FEATURE:
<223> OTHER INFORMATION: 13P11A HC CDR2

<400> SEQUENCE: 38

Ile Ser Ser Ser Gly Ser Thr
1               5

<210> SEQ ID NO 39
<211> LENGTH: 11
<212> TYPE: PRT
<213> ORGANISM: Artificial Sequence
<220> FEATURE:
<223> OTHER INFORMATION: 13P11A HC CDR3

<400> SEQUENCE: 39

Ala Thr Thr Gly Thr Trp Gly Tyr Phe Asp Tyr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: 3C16A HC CDR1

<400> SEQUENCE: 40
```

```
Gly Tyr Thr Phe Thr Ser Tyr Val
1               5

<210> SEQ ID NO 41
<211> LENGTH: 8
<212> TYPE: PRT
<213> ORGANISM: Artificial Sequence
<220> FEATURE:
<223> OTHER INFORMATION: 3C16A HC CDR2

<400> SEQUENCE: 41

Val Ile Pro Tyr Asn Asp Gly Thr
1               5

<210> SEQ ID NO 42
<211> LENGTH: 11
<212> TYPE: PRT
<213> ORGANISM: Artificial Sequence
<220> FEATURE:
<223> OTHER INFORMATION: 3C16A HC CDR3

<400> SEQUENCE: 42

Ala Arg Pro Ser Asn Trp Asp Glu Phe Asp Tyr
1               5                   10

<210> SEQ ID NO 43
<211> LENGTH: 8
<212> TYPE: PRT
<213> ORGANISM: Artificial Sequence
<220> FEATURE:
<223> OTHER INFORMATION: 3I21A HC CDR1

<400> SEQUENCE: 43

Gly Tyr Thr Phe Thr Asn Tyr Trp
1               5

<210> SEQ ID NO 44
<211> LENGTH: 8
<212> TYPE: PRT
<213> ORGANISM: Artificial Sequence
<220> FEATURE:
<223> OTHER INFORMATION: 3I21A HC CDR2

<400> SEQUENCE: 44

Ile His Pro Ser Asp Ser Glu Thr
1               5

<210> SEQ ID NO 45
<211> LENGTH: 9
<212> TYPE: PRT
<213> ORGANISM: Artificial Sequence
<220> FEATURE:
<223> OTHER INFORMATION: 3I21A HC CDR3

<400> SEQUENCE: 45

Ala Arg Tyr Asp Gly Tyr Phe Ala Tyr
1               5

<210> SEQ ID NO 46
<211> LENGTH: 10
<212> TYPE: PRT
<213> ORGANISM: Artificial Sequence
<220> FEATURE:
<223> OTHER INFORMATION: 8H5A HC CDR1

<400> SEQUENCE: 46
```

```
Gly Phe Ser Leu Ser Thr Phe Gly Met Gly
1               5                   10

<210> SEQ ID NO 47
<211> LENGTH: 7
<212> TYPE: PRT
<213> ORGANISM: Artificial Sequence
<220> FEATURE:
<223> OTHER INFORMATION: 8H5A HC CDR2

<400> SEQUENCE: 47

Ile Trp Trp Asp Asp Asp Lys
1               5

<210> SEQ ID NO 48
<211> LENGTH: 12
<212> TYPE: PRT
<213> ORGANISM: Artificial Sequence
<220> FEATURE:
<223> OTHER INFORMATION: 8H5A HC CDR3

<400> SEQUENCE: 48

Ala Arg Thr Tyr Asp Tyr Asp Glu Tyr Phe Asp Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: 15K2A HC CDR1

<400> SEQUENCE: 49

Gly Tyr Thr Phe Thr Ser Tyr Trp
1               5

<210> SEQ ID NO 50
<211> LENGTH: 8
<212> TYPE: PRT
<213> ORGANISM: Artificial Sequence
<220> FEATURE:
<223> OTHER INFORMATION: 15K2A HC CDR2

<400> SEQUENCE: 50

Ile His Pro Ser Asp Ser Glu Thr
1               5

<210> SEQ ID NO 51
<211> LENGTH: 12
<212> TYPE: PRT
<213> ORGANISM: Artificial Sequence
<220> FEATURE:
<223> OTHER INFORMATION: 15K2A HC CDR3

<400> SEQUENCE: 51

Ala Arg Glu Asp Gly Tyr Tyr Trp Tyr Phe Asp Val
1               5                   10

<210> SEQ ID NO 52
<211> LENGTH: 8
<212> TYPE: PRT
<213> ORGANISM: Artificial Sequence
<220> FEATURE:
<223> OTHER INFORMATION: 5A24A HC CDR1

<400> SEQUENCE: 52

Gly Tyr Lys Phe Thr Asp Phe Asn
```

```
<210> SEQ ID NO 53
<211> LENGTH: 8
<212> TYPE: PRT
<213> ORGANISM: Artificial Sequence
<220> FEATURE:
<223> OTHER INFORMATION: 5A24A HC CDR2

<400> SEQUENCE: 53

Ile Asn Pro Asn Ser Gly Gly Thr
1               5

<210> SEQ ID NO 54
<211> LENGTH: 10
<212> TYPE: PRT
<213> ORGANISM: Artificial Sequence
<220> FEATURE:
<223> OTHER INFORMATION: 5A24A HC CDR3

<400> SEQUENCE: 54

Ala Arg Trp Asp Tyr Gly Asn Phe Ala Tyr
1               5                   10

<210> SEQ ID NO 55
<211> LENGTH: 8
<212> TYPE: PRT
<213> ORGANISM: Artificial Sequence
<220> FEATURE:
<223> OTHER INFORMATION: 15P17A HC CDR1

<400> SEQUENCE: 55

Gly Tyr Thr Phe Thr Asn Tyr Trp
1               5

<210> SEQ ID NO 56
<211> LENGTH: 8
<212> TYPE: PRT
<213> ORGANISM: Artificial Sequence
<220> FEATURE:
<223> OTHER INFORMATION: 15P17A HC CDR2

<400> SEQUENCE: 56

Ile His Pro Ser Asp Ser Glu Thr
1               5

<210> SEQ ID NO 57
<211> LENGTH: 12
<212> TYPE: PRT
<213> ORGANISM: Artificial Sequence
<220> FEATURE:
<223> OTHER INFORMATION: 15P17A HC CDR3

<400> SEQUENCE: 57

Ala Arg Glu Asp Gly Tyr Tyr Trp Tyr Phe Asp Val
1               5                   10

<210> SEQ ID NO 58
<211> LENGTH: 8
<212> TYPE: PRT
<213> ORGANISM: Artificial Sequence
<220> FEATURE:
<223> OTHER INFORMATION: 15N21A HC CDR1

<400> SEQUENCE: 58

Gly Phe Thr Phe Ser Ser Tyr Ala
1               5
```

<210> SEQ ID NO 59
<211> LENGTH: 8
<212> TYPE: PRT
<213> ORGANISM: Artificial Sequence
<220> FEATURE:
<223> OTHER INFORMATION: 15N21A HC CDR2

<400> SEQUENCE: 59

Ile Asn Ser Asn Gly Gly Arg Asn
1               5

<210> SEQ ID NO 60
<211> LENGTH: 13
<212> TYPE: PRT
<213> ORGANISM: Artificial Sequence
<220> FEATURE:
<223> OTHER INFORMATION: 15N21A HC CDR3

<400> SEQUENCE: 60

Ala Arg His Arg Gly Gly Tyr Tyr Tyr Ala Met Asp Tyr
1               5                   10

<210> SEQ ID NO 61
<211> LENGTH: 6
<212> TYPE: PRT
<213> ORGANISM: Artificial Sequence
<220> FEATURE:
<223> OTHER INFORMATION: 13P9A LC CDR1

<400> SEQUENCE: 61

Gln Asn Ile Asn Val Trp
1               5

<210> SEQ ID NO 62
<211> LENGTH: 3
<212> TYPE: PRT
<213> ORGANISM: Artificial Sequence
<220> FEATURE:
<223> OTHER INFORMATION: 13P9A LC CDR2

<400> SEQUENCE: 62

Lys Ala Ser
1

<210> SEQ ID NO 63
<211> LENGTH: 9
<212> TYPE: PRT
<213> ORGANISM: Artificial Sequence
<220> FEATURE:
<223> OTHER INFORMATION: 13P9A LC CDR3

<400> SEQUENCE: 63

Gln Gln Gly Gln Ser Tyr Pro Phe Thr
1               5

<210> SEQ ID NO 64
<211> LENGTH: 6
<212> TYPE: PRT
<213> ORGANISM: Artificial Sequence
<220> FEATURE:
<223> OTHER INFORMATION: 5A16A LC CDR1

<400> SEQUENCE: 64

Gly Asn Ile His Asn Tyr
1               5

```
<210> SEQ ID NO 65
<211> LENGTH: 3
<212> TYPE: PRT
<213> ORGANISM: Artificial Sequence
<220> FEATURE:
<223> OTHER INFORMATION: 5A16A LC CDR2

<400> SEQUENCE: 65

Asn Ala Lys
1

<210> SEQ ID NO 66
<211> LENGTH: 9
<212> TYPE: PRT
<213> ORGANISM: Artificial Sequence
<220> FEATURE:
<223> OTHER INFORMATION: 5A16A LC CDR3

<400> SEQUENCE: 66

Gln His Phe Trp Thr Thr Pro Trp Thr
1               5

<210> SEQ ID NO 67
<211> LENGTH: 12
<212> TYPE: PRT
<213> ORGANISM: Artificial Sequence
<220> FEATURE:
<223> OTHER INFORMATION: 14L22A LC CDR1

<400> SEQUENCE: 67

Gln Ser Val Leu Tyr Ser Ser Asn Gln Lys Asn Tyr
1               5                   10

<210> SEQ ID NO 68
<211> LENGTH: 3
<212> TYPE: PRT
<213> ORGANISM: Artificial Sequence
<220> FEATURE:
<223> OTHER INFORMATION: 14L22A LC CDR2

<400> SEQUENCE: 68

Trp Ala Ser
1

<210> SEQ ID NO 69
<211> LENGTH: 8
<212> TYPE: PRT
<213> ORGANISM: Artificial Sequence
<220> FEATURE:
<223> OTHER INFORMATION: 14L22A LC CDR3

<400> SEQUENCE: 69

His Gln Tyr Leu Ser Ser Arg Thr
1               5

<210> SEQ ID NO 70
<211> LENGTH: 10
<212> TYPE: PRT
<213> ORGANISM: Artificial Sequence
<220> FEATURE:
<223> OTHER INFORMATION: 10P18A LC CDR1

<400> SEQUENCE: 70

Lys Ser Val Ser Thr Ser Gly Tyr Ser Tyr
1               5                   10
```

```
<210> SEQ ID NO 71
<211> LENGTH: 3
<212> TYPE: PRT
<213> ORGANISM: Artificial Sequence
<220> FEATURE:
<223> OTHER INFORMATION: 10P18A LC CDR2

<400> SEQUENCE: 71

Leu Ala Ser
1

<210> SEQ ID NO 72
<211> LENGTH: 9
<212> TYPE: PRT
<213> ORGANISM: Artificial Sequence
<220> FEATURE:
<223> OTHER INFORMATION: 10P18A LC CDR3

<400> SEQUENCE: 72

Gln His Ser Arg Glu Leu Pro Tyr Thr
1               5

<210> SEQ ID NO 73
<211> LENGTH: 6
<212> TYPE: PRT
<213> ORGANISM: Artificial Sequence
<220> FEATURE:
<223> OTHER INFORMATION: 13P11A LC CDR1

<400> SEQUENCE: 73

Glu Asn Val Gly Thr Tyr
1               5

<210> SEQ ID NO 74
<211> LENGTH: 3
<212> TYPE: PRT
<213> ORGANISM: Artificial Sequence
<220> FEATURE:
<223> OTHER INFORMATION: 13P11A LC CDR2

<400> SEQUENCE: 74

Gly Ala Ser
1

<210> SEQ ID NO 75
<211> LENGTH: 9
<212> TYPE: PRT
<213> ORGANISM: Artificial Sequence
<220> FEATURE:
<223> OTHER INFORMATION: 13P11A LC CDR3

<400> SEQUENCE: 75

Gly Gln Ser Tyr Ser Tyr Pro Phe Thr
1               5

<210> SEQ ID NO 76
<211> LENGTH: 6
<212> TYPE: PRT
<213> ORGANISM: Artificial Sequence
<220> FEATURE:
<223> OTHER INFORMATION: 3C16A LC CDR1

<400> SEQUENCE: 76

Gln Asn Val Arg Thr Ala
1               5

<210> SEQ ID NO 77
```

```
<211> LENGTH: 3
<212> TYPE: PRT
<213> ORGANISM: Artificial Sequence
<220> FEATURE:
<223> OTHER INFORMATION: 3C16A LC CDR2

<400> SEQUENCE: 77

Leu Ala Ser
1

<210> SEQ ID NO 78
<211> LENGTH: 9
<212> TYPE: PRT
<213> ORGANISM: Artificial Sequence
<220> FEATURE:
<223> OTHER INFORMATION: 3C16A LC CDR3

<400> SEQUENCE: 78

Leu Gln His Trp Asn Tyr Pro Leu Thr
1               5

<210> SEQ ID NO 79
<211> LENGTH: 6
<212> TYPE: PRT
<213> ORGANISM: Artificial Sequence
<220> FEATURE:
<223> OTHER INFORMATION: 3I21A LC CDR1

<400> SEQUENCE: 79

Asp His Ile Asn Asn Trp
1               5

<210> SEQ ID NO 80
<211> LENGTH: 3
<212> TYPE: PRT
<213> ORGANISM: Artificial Sequence
<220> FEATURE:
<223> OTHER INFORMATION: 3I21A LC CDR2

<400> SEQUENCE: 80

Gly Ala Thr
1

<210> SEQ ID NO 81
<211> LENGTH: 9
<212> TYPE: PRT
<213> ORGANISM: Artificial Sequence
<220> FEATURE:
<223> OTHER INFORMATION: 3I21A LC CDR3

<400> SEQUENCE: 81

Gln Gln Tyr Trp Ser Ile Pro Phe Thr
1               5

<210> SEQ ID NO 82
<211> LENGTH: 11
<212> TYPE: PRT
<213> ORGANISM: Artificial Sequence
<220> FEATURE:
<223> OTHER INFORMATION: 8H5A LC CDR1

<400> SEQUENCE: 82

Lys Ser Leu Leu His Ser Asn Gly Ile Thr Tyr
1               5                   10

<210> SEQ ID NO 83
<211> LENGTH: 3
```

```
<212> TYPE: PRT
<213> ORGANISM: Artificial Sequence
<220> FEATURE:
<223> OTHER INFORMATION: 8H5A LC CDR2

<400> SEQUENCE: 83

Gln Met Ser
1

<210> SEQ ID NO 84
<211> LENGTH: 9
<212> TYPE: PRT
<213> ORGANISM: Artificial Sequence
<220> FEATURE:
<223> OTHER INFORMATION: 8H5A LC CDR3

<400> SEQUENCE: 84

Ala Gln Asn Leu Glu Leu Pro Phe Thr
1               5

<210> SEQ ID NO 85
<211> LENGTH: 10
<212> TYPE: PRT
<213> ORGANISM: Artificial Sequence
<220> FEATURE:
<223> OTHER INFORMATION: 15K2A LC CDR1

<400> SEQUENCE: 85

Glu Ser Val Asp Ile Tyr Gly Asn Ser Phe
1               5                   10

<210> SEQ ID NO 86
<211> LENGTH: 3
<212> TYPE: PRT
<213> ORGANISM: Artificial Sequence
<220> FEATURE:
<223> OTHER INFORMATION: 15K2A LC CDR2

<400> SEQUENCE: 86

Leu Ala Ser
1

<210> SEQ ID NO 87
<211> LENGTH: 9
<212> TYPE: PRT
<213> ORGANISM: Artificial Sequence
<220> FEATURE:
<223> OTHER INFORMATION: 15K2A LC CDR3

<400> SEQUENCE: 87

Gln Gln Asn Asn Glu Asp Pro Trp Thr
1               5

<210> SEQ ID NO 88
<211> LENGTH: 11
<212> TYPE: PRT
<213> ORGANISM: Artificial Sequence
<220> FEATURE:
<223> OTHER INFORMATION: 5A24A LC CDR1

<400> SEQUENCE: 88

Lys Ser Leu Leu His Ser Asn Gly Ile Thr Tyr
1               5                   10

<210> SEQ ID NO 89
<211> LENGTH: 3
<212> TYPE: PRT
```

<213> ORGANISM: Artificial Sequence
<220> FEATURE:
<223> OTHER INFORMATION: 5A24A LC CDR2

<400> SEQUENCE: 89

Gln Met Ser
1

<210> SEQ ID NO 90
<211> LENGTH: 9
<212> TYPE: PRT
<213> ORGANISM: Artificial Sequence
<220> FEATURE:
<223> OTHER INFORMATION: 5A24A LC CDR3

<400> SEQUENCE: 90

Ala Gln Asn Leu Glu Leu Pro Leu Thr
1               5

<210> SEQ ID NO 91
<211> LENGTH: 10
<212> TYPE: PRT
<213> ORGANISM: Artificial Sequence
<220> FEATURE:
<223> OTHER INFORMATION: 15P17A LC CDR1

<400> SEQUENCE: 91

Glu Ser Val Asp Ser Tyr Gly Asn Ser Phe
1               5                   10

<210> SEQ ID NO 92
<211> LENGTH: 3
<212> TYPE: PRT
<213> ORGANISM: Artificial Sequence
<220> FEATURE:
<223> OTHER INFORMATION: 15P17A LC CDR2

<400> SEQUENCE: 92

Leu Ala Ser
1

<210> SEQ ID NO 93
<211> LENGTH: 9
<212> TYPE: PRT
<213> ORGANISM: Artificial Sequence
<220> FEATURE:
<223> OTHER INFORMATION: 15P17A LC CDR3

<400> SEQUENCE: 93

Gln Gln Asn His Glu Asp Pro Trp Thr
1               5

<210> SEQ ID NO 94
<211> LENGTH: 12
<212> TYPE: PRT
<213> ORGANISM: Artificial Sequence
<220> FEATURE:
<223> OTHER INFORMATION: 15N21A LC CDR1

<400> SEQUENCE: 94

Gln Ser Leu Leu Tyr Ser Ser Asn Gln Lys Asn Tyr
1               5                   10

<210> SEQ ID NO 95
<211> LENGTH: 3
<212> TYPE: PRT
<213> ORGANISM: Artificial Sequence

```
<220> FEATURE:
<223> OTHER INFORMATION: 15N21A LC CDR2

<400> SEQUENCE: 95

Trp Ala Ser
1

<210> SEQ ID NO 96
<211> LENGTH: 8
<212> TYPE: PRT
<213> ORGANISM: Artificial Sequence
<220> FEATURE:
<223> OTHER INFORMATION: 15N21A LC CDR3

<400> SEQUENCE: 96

Gln Gln Tyr Tyr Thr Tyr Leu Thr
1               5

<210> SEQ ID NO 97
<211> LENGTH: 5
<212> TYPE: PRT
<213> ORGANISM: Artificial Sequence
<220> FEATURE:
<223> OTHER INFORMATION: 13P9A HC CDR1

<400> SEQUENCE: 97

Ser Tyr Val Met His
1               5

<210> SEQ ID NO 98
<211> LENGTH: 17
<212> TYPE: PRT
<213> ORGANISM: Artificial Sequence
<220> FEATURE:
<223> OTHER INFORMATION: 13P9A HC CDR2

<400> SEQUENCE: 98

Tyr Ile Asn Pro Tyr Asn Asp Ala Thr Lys Tyr Asn Glu Lys Phe Lys
1               5                   10                  15

Gly

<210> SEQ ID NO 99
<211> LENGTH: 9
<212> TYPE: PRT
<213> ORGANISM: Artificial Sequence
<220> FEATURE:
<223> OTHER INFORMATION: 13P9A HC CDR3

<400> SEQUENCE: 99

Gly Gly Tyr Asp Tyr Asp Gly Asp Tyr
1               5

<210> SEQ ID NO 100
<211> LENGTH: 5
<212> TYPE: PRT
<213> ORGANISM: Artificial Sequence
<220> FEATURE:
<223> OTHER INFORMATION: 5A16A HC CDR1

<400> SEQUENCE: 100

Arg Tyr Ile Leu His
1               5

<210> SEQ ID NO 101
<211> LENGTH: 17
<212> TYPE: PRT
```

```
<213> ORGANISM: Artificial Sequence
<220> FEATURE:
<223> OTHER INFORMATION: 5A16A HC CDR2

<400> SEQUENCE: 101

Tyr Ile Asn Pro Tyr Asn Asp Gly Thr Lys Tyr Asn Glu Lys Phe Lys
1               5                   10                  15

Gly

<210> SEQ ID NO 102
<211> LENGTH: 13
<212> TYPE: PRT
<213> ORGANISM: Artificial Sequence
<220> FEATURE:
<223> OTHER INFORMATION: 5A16A HC CDR3

<400> SEQUENCE: 102

Asp Ser Ser Gly Tyr Gly Gly Ala Tyr Ala Met Asp Phe
1               5                   10

<210> SEQ ID NO 103
<211> LENGTH: 5
<212> TYPE: PRT
<213> ORGANISM: Artificial Sequence
<220> FEATURE:
<223> OTHER INFORMATION: 14L22A HC CDR1

<400> SEQUENCE: 103

Ser Tyr Ala Met Ser
1               5

<210> SEQ ID NO 104
<211> LENGTH: 17
<212> TYPE: PRT
<213> ORGANISM: Artificial Sequence
<220> FEATURE:
<223> OTHER INFORMATION: 14L22A HC CDR2

<400> SEQUENCE: 104

Ala Ile Asn Ser Asn Gly Gly Asn Thr Tyr Tyr Pro Asp Thr Val Lys
1               5                   10                  15

Asp

<210> SEQ ID NO 105
<211> LENGTH: 11
<212> TYPE: PRT
<213> ORGANISM: Artificial Sequence
<220> FEATURE:
<223> OTHER INFORMATION: 14L22A HC CDR3

<400> SEQUENCE: 105

His Arg Gly Gly Phe Tyr Tyr Ala Val Asp Tyr
1               5                   10

<210> SEQ ID NO 106
<211> LENGTH: 5
<212> TYPE: PRT
<213> ORGANISM: Artificial Sequence
<220> FEATURE:
<223> OTHER INFORMATION: 10P18A HC CDR1

<400> SEQUENCE: 106

Gly Tyr Tyr Ile Asp
1               5
```

```
<210> SEQ ID NO 107
<211> LENGTH: 17
<212> TYPE: PRT
<213> ORGANISM: Artificial Sequence
<220> FEATURE:
<223> OTHER INFORMATION: 10P18A HC CDR2

<400> SEQUENCE: 107

Tyr Ile Tyr Pro Ser Asn Gly Glu Thr Ser Tyr Asn Gln Lys Phe Lys
1               5                   10                  15
Gly

<210> SEQ ID NO 108
<211> LENGTH: 7
<212> TYPE: PRT
<213> ORGANISM: Artificial Sequence
<220> FEATURE:
<223> OTHER INFORMATION: 10P18A HC CDR3

<400> SEQUENCE: 108

Glu Ser Tyr Ala Met Asp Tyr
1               5

<210> SEQ ID NO 109
<211> LENGTH: 7
<212> TYPE: PRT
<213> ORGANISM: Artificial Sequence
<220> FEATURE:
<223> OTHER INFORMATION: 13P11A HC CDR1

<400> SEQUENCE: 109

Asn Gly Asn His Trp Trp Ser
1               5

<210> SEQ ID NO 110
<211> LENGTH: 16
<212> TYPE: PRT
<213> ORGANISM: Artificial Sequence
<220> FEATURE:
<223> OTHER INFORMATION: 13P11A HC CDR2

<400> SEQUENCE: 110

Tyr Ile Ser Ser Ser Gly Ser Thr Asp Ser Asn Pro Ser Leu Lys Ser
1               5                   10                  15

<210> SEQ ID NO 111
<211> LENGTH: 9
<212> TYPE: PRT
<213> ORGANISM: Artificial Sequence
<220> FEATURE:
<223> OTHER INFORMATION: 13P11A HC CDR3

<400> SEQUENCE: 111

Thr Gly Thr Trp Gly Tyr Phe Asp Tyr
1               5

<210> SEQ ID NO 112
<211> LENGTH: 5
<212> TYPE: PRT
<213> ORGANISM: Artificial Sequence
<220> FEATURE:
<223> OTHER INFORMATION: 3C16A HC CDR1

<400> SEQUENCE: 112

Ser Tyr Val Met His
1               5
```

<210> SEQ ID NO 113
<211> LENGTH: 17
<212> TYPE: PRT
<213> ORGANISM: Artificial Sequence
<220> FEATURE:
<223> OTHER INFORMATION: 3C16A HC CDR2

<400> SEQUENCE: 113

Tyr Val Ile Pro Tyr Asn Asp Gly Thr Lys Tyr Asn Glu Lys Phe Lys
1               5                   10                  15

Gly

<210> SEQ ID NO 114
<211> LENGTH: 9
<212> TYPE: PRT
<213> ORGANISM: Artificial Sequence
<220> FEATURE:
<223> OTHER INFORMATION: 3C16A HC CDR3

<400> SEQUENCE: 114

Pro Ser Asn Trp Asp Glu Phe Asp Tyr
1               5

<210> SEQ ID NO 115
<211> LENGTH: 5
<212> TYPE: PRT
<213> ORGANISM: Artificial Sequence
<220> FEATURE:
<223> OTHER INFORMATION: 3I21A HC CDR1

<400> SEQUENCE: 115

Asn Tyr Trp Met Asn
1               5

<210> SEQ ID NO 116
<211> LENGTH: 17
<212> TYPE: PRT
<213> ORGANISM: Artificial Sequence
<220> FEATURE:
<223> OTHER INFORMATION: 3I21A HC CDR2

<400> SEQUENCE: 116

Arg Ile His Pro Ser Asp Ser Glu Thr His Tyr Asn Gln Lys Phe Lys
1               5                   10                  15

Thr

<210> SEQ ID NO 117
<211> LENGTH: 7
<212> TYPE: PRT
<213> ORGANISM: Artificial Sequence
<220> FEATURE:
<223> OTHER INFORMATION: 3I21A HC CDR3

<400> SEQUENCE: 117

Tyr Asp Gly Tyr Phe Ala Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: 8H5A HC CDR1

<400> SEQUENCE: 118

```
Thr Phe Gly Met Gly Val Gly
1               5

<210> SEQ ID NO 119
<211> LENGTH: 16
<212> TYPE: PRT
<213> ORGANISM: Artificial Sequence
<220> FEATURE:
<223> OTHER INFORMATION: 8H5A HC CDR2

<400> SEQUENCE: 119

His Ile Trp Trp Asp Asp Lys Tyr Tyr Asn Pro Ala Leu Lys Ser
1               5                   10                  15

<210> SEQ ID NO 120
<211> LENGTH: 10
<212> TYPE: PRT
<213> ORGANISM: Artificial Sequence
<220> FEATURE:
<223> OTHER INFORMATION: 8H5A HC CDR3

<400> SEQUENCE: 120

Thr Tyr Asp Tyr Asp Glu Tyr Phe Asp Tyr
1               5                   10

<210> SEQ ID NO 121
<211> LENGTH: 5
<212> TYPE: PRT
<213> ORGANISM: Artificial Sequence
<220> FEATURE:
<223> OTHER INFORMATION: 15K2A HC CDR1

<400> SEQUENCE: 121

Ser Tyr Trp Met Asn
1               5

<210> SEQ ID NO 122
<211> LENGTH: 17
<212> TYPE: PRT
<213> ORGANISM: Artificial Sequence
<220> FEATURE:
<223> OTHER INFORMATION: 15K2A HC CDR2

<400> SEQUENCE: 122

Arg Ile His Pro Ser Asp Ser Glu Thr His Tyr Asn Gln Lys Phe Arg
1               5                   10                  15

Thr

<210> SEQ ID NO 123
<211> LENGTH: 10
<212> TYPE: PRT
<213> ORGANISM: Artificial Sequence
<220> FEATURE:
<223> OTHER INFORMATION: 15K2A HC CDR3

<400> SEQUENCE: 123

Glu Asp Gly Tyr Tyr Trp Tyr Phe Asp Val
1               5                   10

<210> SEQ ID NO 124
<211> LENGTH: 5
<212> TYPE: PRT
<213> ORGANISM: Artificial Sequence
<220> FEATURE:
<223> OTHER INFORMATION: 5A24A HC CDR1

<400> SEQUENCE: 124
```

```
Asp Phe Asn Met Asp
1               5

<210> SEQ ID NO 125
<211> LENGTH: 17
<212> TYPE: PRT
<213> ORGANISM: Artificial Sequence
<220> FEATURE:
<223> OTHER INFORMATION: 5A24A HC CDR2

<400> SEQUENCE: 125

Asp Ile Asn Pro Asn Ser Gly Gly Thr Ile Tyr Asn Gln Lys Phe Lys
1               5                   10                  15

Gly

<210> SEQ ID NO 126
<211> LENGTH: 8
<212> TYPE: PRT
<213> ORGANISM: Artificial Sequence
<220> FEATURE:
<223> OTHER INFORMATION: 5A24A HC CDR3

<400> SEQUENCE: 126

Trp Asp Tyr Gly Asn Phe Ala Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: 15P17A HC CDR1

<400> SEQUENCE: 127

Asn Tyr Trp Met Asn
1               5

<210> SEQ ID NO 128
<211> LENGTH: 17
<212> TYPE: PRT
<213> ORGANISM: Artificial Sequence
<220> FEATURE:
<223> OTHER INFORMATION: 15P17A HC CDR2

<400> SEQUENCE: 128

Arg Ile His Pro Ser Asp Ser Glu Thr His Tyr Asn Gln Lys Phe Lys
1               5                   10                  15

Ser

<210> SEQ ID NO 129
<211> LENGTH: 10
<212> TYPE: PRT
<213> ORGANISM: Artificial Sequence
<220> FEATURE:
<223> OTHER INFORMATION: 15P17A HC CDR3

<400> SEQUENCE: 129

Glu Asp Gly Tyr Tyr Trp Tyr Phe Asp Val
1               5                   10

<210> SEQ ID NO 130
<211> LENGTH: 5
<212> TYPE: PRT
<213> ORGANISM: Artificial Sequence
<220> FEATURE:
```

```
<223> OTHER INFORMATION: 15N21A HC CDR1

<400> SEQUENCE: 130

Ser Tyr Ala Met Ser
1               5

<210> SEQ ID NO 131
<211> LENGTH: 17
<212> TYPE: PRT
<213> ORGANISM: Artificial Sequence
<220> FEATURE:
<223> OTHER INFORMATION: 15N21A HC CDR2

<400> SEQUENCE: 131

Ala Ile Asn Ser Asn Gly Gly Arg Asn Tyr Tyr Pro Asp Thr Val Lys
1               5                   10                  15

Asp

<210> SEQ ID NO 132
<211> LENGTH: 11
<212> TYPE: PRT
<213> ORGANISM: Artificial Sequence
<220> FEATURE:
<223> OTHER INFORMATION: 15N21A HC CDR3

<400> SEQUENCE: 132

His Arg Gly Gly Tyr Tyr Tyr Ala Met Asp Tyr
1               5                   10

<210> SEQ ID NO 133
<211> LENGTH: 11
<212> TYPE: PRT
<213> ORGANISM: Artificial Sequence
<220> FEATURE:
<223> OTHER INFORMATION: 13P9A LC CDR1

<400> SEQUENCE: 133

His Ala Ser Gln Asn Ile Asn Val Trp Leu Ser
1               5                   10

<210> SEQ ID NO 134
<211> LENGTH: 7
<212> TYPE: PRT
<213> ORGANISM: Artificial Sequence
<220> FEATURE:
<223> OTHER INFORMATION: 13P9A LC CDR2

<400> SEQUENCE: 134

Lys Ala Ser Asn Leu His Thr
1               5

<210> SEQ ID NO 135
<211> LENGTH: 9
<212> TYPE: PRT
<213> ORGANISM: Artificial Sequence
<220> FEATURE:
<223> OTHER INFORMATION: 13P9A LC CDR3

<400> SEQUENCE: 135

Gln Gln Gly Gln Ser Tyr Pro Phe Thr
1               5

<210> SEQ ID NO 136
<211> LENGTH: 11
<212> TYPE: PRT
<213> ORGANISM: Artificial Sequence
```

```
<220> FEATURE:
<223> OTHER INFORMATION: 5A16A LC CDR1

<400> SEQUENCE: 136

Arg Ala Ser Gly Asn Ile His Asn Tyr Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: 5A16A LC CDR2

<400> SEQUENCE: 137

Asn Ala Lys Thr Leu Pro Tyr
1               5

<210> SEQ ID NO 138
<211> LENGTH: 9
<212> TYPE: PRT
<213> ORGANISM: Artificial Sequence
<220> FEATURE:
<223> OTHER INFORMATION: 5A16A LC CDR3

<400> SEQUENCE: 138

Gln His Phe Trp Thr Thr Pro Trp Thr
1               5

<210> SEQ ID NO 139
<211> LENGTH: 17
<212> TYPE: PRT
<213> ORGANISM: Artificial Sequence
<220> FEATURE:
<223> OTHER INFORMATION: 14L22A LC CDR1

<400> SEQUENCE: 139

Lys Ser Ser Gln Ser Val Leu Tyr Ser Ser Asn Gln Lys Asn Tyr Leu
1               5                   10                  15

Ala

<210> SEQ ID NO 140
<211> LENGTH: 7
<212> TYPE: PRT
<213> ORGANISM: Artificial Sequence
<220> FEATURE:
<223> OTHER INFORMATION: 14L22A LC CDR2

<400> SEQUENCE: 140

Trp Ala Ser Thr Arg Glu Ser
1               5

<210> SEQ ID NO 141
<211> LENGTH: 8
<212> TYPE: PRT
<213> ORGANISM: Artificial Sequence
<220> FEATURE:
<223> OTHER INFORMATION: 14L22A LC CDR3

<400> SEQUENCE: 141

His Gln Tyr Leu Ser Ser Arg Thr
1               5

<210> SEQ ID NO 142
<211> LENGTH: 15
<212> TYPE: PRT
```

```
<213> ORGANISM: Artificial Sequence
<220> FEATURE:
<223> OTHER INFORMATION: 10P18A LC CDR1

<400> SEQUENCE: 142

Arg Ala Ser Lys Ser Val Ser Thr Ser Gly Tyr Ser Tyr Met His
1               5                   10                  15

<210> SEQ ID NO 143
<211> LENGTH: 7
<212> TYPE: PRT
<213> ORGANISM: Artificial Sequence
<220> FEATURE:
<223> OTHER INFORMATION: 10P18A LC CDR2

<400> SEQUENCE: 143

Leu Ala Ser Asn Leu Glu Ser
1               5

<210> SEQ ID NO 144
<211> LENGTH: 9
<212> TYPE: PRT
<213> ORGANISM: Artificial Sequence
<220> FEATURE:
<223> OTHER INFORMATION: 10P18A LC CDR3

<400> SEQUENCE: 144

Gln His Ser Arg Glu Leu Pro Tyr Thr
1               5

<210> SEQ ID NO 145
<211> LENGTH: 11
<212> TYPE: PRT
<213> ORGANISM: Artificial Sequence
<220> FEATURE:
<223> OTHER INFORMATION: 13P11A LC CDR1

<400> SEQUENCE: 145

Lys Ala Ser Glu Asn Val Gly Thr Tyr Val Ser
1               5                   10

<210> SEQ ID NO 146
<211> LENGTH: 7
<212> TYPE: PRT
<213> ORGANISM: Artificial Sequence
<220> FEATURE:
<223> OTHER INFORMATION: 13P11A LC CDR2

<400> SEQUENCE: 146

Gly Ala Ser Asn Arg Phe Thr
1               5

<210> SEQ ID NO 147
<211> LENGTH: 9
<212> TYPE: PRT
<213> ORGANISM: Artificial Sequence
<220> FEATURE:
<223> OTHER INFORMATION: 13P11A LC CDR3

<400> SEQUENCE: 147

Gly Gln Ser Tyr Ser Tyr Pro Phe Thr
1               5

<210> SEQ ID NO 148
<211> LENGTH: 11
<212> TYPE: PRT
<213> ORGANISM: Artificial Sequence
```

```
<220> FEATURE:
<223> OTHER INFORMATION: 3C16A LC CDR1

<400> SEQUENCE: 148

Lys Ala Ser Gln Asn Val Arg Thr Ala Val Ala
1               5                   10

<210> SEQ ID NO 149
<211> LENGTH: 7
<212> TYPE: PRT
<213> ORGANISM: Artificial Sequence
<220> FEATURE:
<223> OTHER INFORMATION: 3C16A LC CDR2

<400> SEQUENCE: 149

Leu Ala Ser Asn Arg His Thr
1               5

<210> SEQ ID NO 150
<211> LENGTH: 9
<212> TYPE: PRT
<213> ORGANISM: Artificial Sequence
<220> FEATURE:
<223> OTHER INFORMATION: 3C16A LC CDR3

<400> SEQUENCE: 150

Leu Gln His Trp Asn Tyr Pro Leu Thr
1               5

<210> SEQ ID NO 151
<211> LENGTH: 11
<212> TYPE: PRT
<213> ORGANISM: Artificial Sequence
<220> FEATURE:
<223> OTHER INFORMATION: 3I21A LC CDR1

<400> SEQUENCE: 151

Lys Ala Ser Asp His Ile Asn Asn Trp Leu Ala
1               5                   10

<210> SEQ ID NO 152
<211> LENGTH: 7
<212> TYPE: PRT
<213> ORGANISM: Artificial Sequence
<220> FEATURE:
<223> OTHER INFORMATION: 3I21A LC CDR2

<400> SEQUENCE: 152

Gly Ala Thr Ser Leu Glu Thr
1               5

<210> SEQ ID NO 153
<211> LENGTH: 9
<212> TYPE: PRT
<213> ORGANISM: Artificial Sequence
<220> FEATURE:
<223> OTHER INFORMATION: 3I21A LC CDR3

<400> SEQUENCE: 153

Gln Gln Tyr Trp Ser Ile Pro Phe Thr
1               5

<210> SEQ ID NO 154
<211> LENGTH: 16
<212> TYPE: PRT
<213> ORGANISM: Artificial Sequence
<220> FEATURE:
```

<223> OTHER INFORMATION: 8H5A LC CDR1

<400> SEQUENCE: 154

Arg Ser Ser Lys Ser Leu Leu His Ser Asn Gly Ile Thr Tyr Phe Tyr
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: 8H5A LC CDR2

<400> SEQUENCE: 155

Gln Met Ser Asn Leu Ala Ser
1               5

<210> SEQ ID NO 156
<211> LENGTH: 9
<212> TYPE: PRT
<213> ORGANISM: Artificial Sequence
<220> FEATURE:
<223> OTHER INFORMATION: 8H5A LC CDR3

<400> SEQUENCE: 156

Ala Gln Asn Leu Glu Leu Pro Phe Thr
1               5

<210> SEQ ID NO 157
<211> LENGTH: 15
<212> TYPE: PRT
<213> ORGANISM: Artificial Sequence
<220> FEATURE:
<223> OTHER INFORMATION: 15K2A LC CDR1

<400> SEQUENCE: 157

Arg Ala Ser Glu Ser Val Asp Ile Tyr Gly Asn Ser Phe Met His
1               5                   10                  15

<210> SEQ ID NO 158
<211> LENGTH: 7
<212> TYPE: PRT
<213> ORGANISM: Artificial Sequence
<220> FEATURE:
<223> OTHER INFORMATION: 15K2A LC CDR2

<400> SEQUENCE: 158

Leu Ala Ser Asn Leu Glu Ser
1               5

<210> SEQ ID NO 159
<211> LENGTH: 9
<212> TYPE: PRT
<213> ORGANISM: Artificial Sequence
<220> FEATURE:
<223> OTHER INFORMATION: 15K2A LC CDR3

<400> SEQUENCE: 159

Gln Gln Asn Asn Glu Asp Pro Trp Thr
1               5

<210> SEQ ID NO 160
<211> LENGTH: 16
<212> TYPE: PRT
<213> ORGANISM: Artificial Sequence
<220> FEATURE:
<223> OTHER INFORMATION: 5A24A LC CDR1

<400> SEQUENCE: 160

Arg Ser Ser Lys Ser Leu Leu His Ser Asn Gly Ile Thr Tyr Leu Tyr
1               5                   10                  15

<210> SEQ ID NO 161
<211> LENGTH: 7
<212> TYPE: PRT
<213> ORGANISM: Artificial Sequence
<220> FEATURE:
<223> OTHER INFORMATION: 5A24A LC CDR2

<400> SEQUENCE: 161

Gln Met Ser Asn Leu Ala Ser
1               5

<210> SEQ ID NO 162
<211> LENGTH: 9
<212> TYPE: PRT
<213> ORGANISM: Artificial Sequence
<220> FEATURE:
<223> OTHER INFORMATION: 5A24A LC CDR3

<400> SEQUENCE: 162

Ala Gln Asn Leu Glu Leu Pro Leu Thr
1               5

<210> SEQ ID NO 163
<211> LENGTH: 15
<212> TYPE: PRT
<213> ORGANISM: Artificial Sequence
<220> FEATURE:
<223> OTHER INFORMATION: 15P17A LC CDR1

<400> SEQUENCE: 163

Arg Ala Ser Glu Ser Val Asp Ser Tyr Gly Asn Ser Phe Met His
1               5                   10                  15

<210> SEQ ID NO 164
<211> LENGTH: 7
<212> TYPE: PRT
<213> ORGANISM: Artificial Sequence
<220> FEATURE:
<223> OTHER INFORMATION: 15P17A LC CDR2

<400> SEQUENCE: 164

Leu Ala Ser Asn Leu Glu Ser
1               5

<210> SEQ ID NO 165
<211> LENGTH: 9
<212> TYPE: PRT
<213> ORGANISM: Artificial Sequence
<220> FEATURE:
<223> OTHER INFORMATION: 15P17A LC CDR3

<400> SEQUENCE: 165

Gln Gln Asn His Glu Asp Pro Trp Thr
1               5

<210> SEQ ID NO 166
<211> LENGTH: 17
<212> TYPE: PRT
<213> ORGANISM: Artificial Sequence
<220> FEATURE:
<223> OTHER INFORMATION: 15N21A LC CDR1

-continued

<400> SEQUENCE: 166

Lys Ser Ser Gln Ser Leu Leu Tyr Ser Ser Asn Gln Lys Asn Tyr Leu
1               5                   10                  15

Ala

<210> SEQ ID NO 167
<211> LENGTH: 7
<212> TYPE: PRT
<213> ORGANISM: Artificial Sequence
<220> FEATURE:
<223> OTHER INFORMATION: 15N21A LC CDR2

<400> SEQUENCE: 167

Trp Ala Ser Thr Arg Glu Ser
1               5

<210> SEQ ID NO 168
<211> LENGTH: 8
<212> TYPE: PRT
<213> ORGANISM: Artificial Sequence
<220> FEATURE:
<223> OTHER INFORMATION: 15N21A LC CDR3

<400> SEQUENCE: 168

Gln Gln Tyr Tyr Thr Tyr Leu Thr
1               5

<210> SEQ ID NO 169
<211> LENGTH: 618
<212> TYPE: PRT
<213> ORGANISM: Homo sapiens

<400> SEQUENCE: 169

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
                20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
        50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

```
Pro Leu Glu Asp Glu Cys Glu Ala Pro Leu Val Cys Arg Ala Gly Cys
    210                 215                 220
Ser Pro Glu His Gly Phe Cys Glu Gln Pro Gly Glu Cys Arg Cys Leu
225                 230                 235                 240
Glu Gly Trp Thr Gly Pro Leu Cys Thr Val Pro Val Ser Thr Ser Ser
                245                 250                 255
Cys Leu Ser Pro Arg Gly Pro Ser Ser Ala Thr Thr Gly Cys Leu Val
                260                 265                 270
Pro Gly Pro Gly Pro Cys Asp Gly Asn Pro Cys Ala Asn Gly Gly Ser
                275                 280                 285
Cys Ser Glu Thr Pro Arg Ser Phe Glu Cys Thr Cys Pro Arg Gly Phe
    290                 295                 300
Tyr Gly Leu Arg Cys Glu Val Ser Gly Val Thr Cys Ala Asp Gly Pro
305                 310                 315                 320
Cys Phe Asn Gly Gly Leu Cys Val Gly Ala Asp Pro Asp Ser Ala
                325                 330                 335
Tyr Ile Cys His Cys Pro Pro Gly Phe Gln Gly Ser Asn Cys Glu Lys
                340                 345                 350
Arg Val Asp Arg Cys Ser Leu Gln Pro Cys Arg Asn Gly Gly Leu Cys
                355                 360                 365
Leu Asp Leu Gly His Ala Leu Arg Cys Arg Cys Arg Ala Gly Phe Ala
    370                 375                 380
Gly Pro Arg Cys Glu His Asp Leu Asp Asp Cys Ala Gly Arg Ala Cys
385                 390                 395                 400
Ala Asn Gly Gly Thr Cys Val Glu Gly Gly Ala His Arg Cys Ser
                405                 410                 415
Cys Ala Leu Gly Phe Gly Gly Arg Asp Cys Arg Glu Arg Ala Asp Pro
                420                 425                 430
Cys Ala Ala Arg Pro Cys Ala His Gly Gly Arg Cys Tyr Ala His Phe
    435                 440                 445
Ser Gly Leu Val Cys Ala Cys Ala Pro Gly Tyr Met Gly Ala Arg Cys
    450                 455                 460
Glu Phe Pro Val His Pro Asp Gly Ala Ser Ala Leu Pro Ala Ala Pro
465                 470                 475                 480
Pro Gly Leu Arg Pro Gly Asp Pro Gln Arg Tyr Leu Pro Pro Ala
                485                 490                 495
Leu Gly Leu Leu Val Ala Ala Gly Val Ala Gly Ala Ala Leu Leu Leu
                500                 505                 510
Val His Val Arg Arg Arg Gly His Ser Gln Asp Ala Gly Ser Arg Leu
    515                 520                 525
Leu Ala Gly Thr Pro Glu Pro Ser Val His Ala Leu Pro Asp Ala Leu
530                 535                 540
Asn Asn Leu Arg Thr Gln Glu Gly Ser Gly Asp Gly Pro Ser Ser Ser
545                 550                 555                 560
Val Asp Trp Asn Arg Pro Glu Asp Val Asp Pro Gln Gly Ile Tyr Val
                565                 570                 575
Ile Ser Ala Pro Ser Ile Tyr Ala Arg Glu Val Ala Thr Pro Leu Phe
                580                 585                 590
Pro Pro Leu His Thr Gly Arg Ala Gly Gln Arg Gln His Leu Leu Phe
                595                 600                 605
Pro Tyr Pro Ser Ser Ile Leu Ser Val Lys
    610                 615
```

```
<210> SEQ ID NO 170
<211> LENGTH: 118
<212> TYPE: PRT
<213> ORGANISM: Artificial Sequence
<220> FEATURE:
<223> OTHER INFORMATION: H1 Heavy Chain Variable Region

<400> SEQUENCE: 170

Glu Val Arg Leu Ser Gln Ser Gly Gly Gln Met Lys Lys Pro Gly Glu
1               5                   10                  15

Ser Met Arg Leu Ser Cys Arg Ala Ser Gly Tyr Thr Phe Thr Ser Tyr
                20                  25                  30

Val Met His Trp Val Arg Gln Ala Pro Gly Arg Arg Pro Glu Trp Ile
            35                  40                  45

Gly Tyr Ile Asn Pro Tyr Asn Asp Ala Thr Lys Tyr Ala Arg Lys Phe
    50                  55                  60

Gln Gly Arg Ala Thr Leu Thr Ser Asp Lys Tyr Ser Asp Thr Ala Phe
65                  70                  75                  80

Leu Glu Leu Arg Ser Leu Thr Ser Asp Asp Thr Ala Val Tyr Tyr Cys
                85                  90                  95

Ala Arg Gly Gly Tyr Asp Tyr Asp Gly Asp Tyr Trp Gly Arg Gly Ala
            100                 105                 110

Pro Val Thr Val Ser Ser
        115

<210> SEQ ID NO 171
<211> LENGTH: 107
<212> TYPE: PRT
<213> ORGANISM: Artificial Sequence
<220> FEATURE:
<223> OTHER INFORMATION: L1 Light Chain Variable Region

<400> SEQUENCE: 171

Glu Ile Val Met Thr Gln Ser Pro Gly Thr Leu Ser Leu Ser Pro Gly
1               5                   10                  15

Glu Arg Ala Thr Leu Ser Cys His Ala Ser Gln Asn Ile Asn Val Trp
                20                  25                  30

Leu Ser Trp Tyr Gln Gln Lys Pro Gly Gln Ala Pro Arg Leu Leu Ile
            35                  40                  45

Tyr Lys Ala Ser Asn Leu His Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly Gln Ser Tyr Pro Phe
                85                  90                  95

Thr Phe Gly Gln Gly Thr Lys Val Glu Ile Lys
            100                 105

<210> SEQ ID NO 172
<211> LENGTH: 107
<212> TYPE: PRT
<213> ORGANISM: Artificial Sequence
<220> FEATURE:
<223> OTHER INFORMATION: L2 Light Chain Variable Region

<400> SEQUENCE: 172

Glu Ile Val Leu Thr Gln Ser Pro Gly Thr Leu Ser Leu Ser Pro Gly
1               5                   10                  15

Glu Arg Ala Thr Leu Ser Cys His Ala Ser Gln Asn Ile Asn Val Trp
```

```
                20                  25                  30

Leu Ser Trp Tyr Gln Gln Lys Pro Gly Gln Ala Pro Arg Leu Leu Ile
            35                  40                  45

Tyr Lys Ala Ser Asn Leu His Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly Gln Ser Tyr Pro Phe
                85                  90                  95

Thr Phe Gly Gln Gly Thr Lys Val Glu Ile Lys
            100                 105

<210> SEQ ID NO 173
<211> LENGTH: 107
<212> TYPE: PRT
<213> ORGANISM: Artificial Sequence
<220> FEATURE:
<223> OTHER INFORMATION: L3 Light Chain Variable Region

<400> SEQUENCE: 173

Glu Ile Val Met Thr Gln Ser Pro Ala Thr Leu Ser Leu Ser Pro Gly
1               5                   10                  15

Glu Thr Ala Ile Ile Ser Cys His Ala Ser Gln Asn Ile Asn Val Trp
            20                  25                  30

Leu Ser Trp Tyr Gln Gln Arg Pro Gly Gln Ala Pro Arg Leu Leu Ile
            35                  40                  45

Tyr Lys Ala Ser Asn Leu His Thr Gly Ile Pro Asp Arg Phe Ser Gly
        50                  55                  60

Ser Gly Trp Gly Thr Asp Phe Asn Leu Ser Ile Ser Asn Leu Glu Ser
65                  70                  75                  80

Gly Asp Phe Gly Val Tyr Tyr Cys Gln Gln Gly Gln Ser Tyr Pro Phe
                85                  90                  95

Thr Phe Gly Gln Gly Thr Lys Val Glu Ile Lys
            100                 105

<210> SEQ ID NO 174
<211> LENGTH: 107
<212> TYPE: PRT
<213> ORGANISM: Artificial Sequence
<220> FEATURE:
<223> OTHER INFORMATION: L4 Light Chain Variable Region

<400> SEQUENCE: 174

Glu Ile Val Met Thr Gln Ser Pro Ala Thr Leu Ser Leu Ser Pro Gly
1               5                   10                  15

Glu Thr Ala Ile Ile Ser Cys His Ala Ser Gln Asn Ile Asn Val Trp
            20                  25                  30

Leu Ser Trp Tyr Gln Gln Arg Pro Gly Gln Ala Pro Arg Leu Leu Ile
            35                  40                  45

Tyr Lys Ala Ser Asn Leu His Thr Gly Ile Pro Asp Arg Phe Ser Gly
        50                  55                  60

Ser Gly Trp Gly Thr Asp Phe Asn Leu Ser Ile Ser Asn Leu Glu Ser
65                  70                  75                  80

Gly Asp Phe Gly Val Tyr Tyr Cys Gln Gln Gly Gln Ser Tyr Pro Trp
                85                  90                  95

Thr Phe Gly Gln Gly Thr Lys Val Glu Ile Lys
            100                 105
```

<210> SEQ ID NO 175
<211> LENGTH: 114
<212> TYPE: PRT
<213> ORGANISM: Artificial Sequence
<220> FEATURE:
<223> OTHER INFORMATION: KH1 Heavy Chain Variable Region

<400> SEQUENCE: 175

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asp Ser Glu Thr His Tyr Ala Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Thr Asp Leu Ala Tyr Trp Gly Gln Gly Thr Leu Val Thr Val
            100                 105                 110

Ser Ser
```

<210> SEQ ID NO 176
<211> LENGTH: 114
<212> TYPE: PRT
<213> ORGANISM: Artificial Sequence
<220> FEATURE:
<223> OTHER INFORMATION: KH2 Heavy Chain Variable Region

<400> SEQUENCE: 176

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asp Ser Glu Thr His Tyr Ala Gln Lys Phe
    50                  55                  60

Gln Gly Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Gly Thr Asp Leu Ala Tyr Trp Gly Gln Gly Thr Leu Val Thr Val
            100                 105                 110

Ser Ser
```

<210> SEQ ID NO 177
<211> LENGTH: 114
<212> TYPE: PRT
<213> ORGANISM: Artificial Sequence
<220> FEATURE:
<223> OTHER INFORMATION: KH3 Heavy Chain Variable Region

<400> SEQUENCE: 177

```
Glu Val Arg Leu Ser Gln Ser Gly Gly Gln Met Lys Lys Pro Gly Glu
1               5                   10                  15
```

```
Ser Met Arg Leu Ser Cys Arg Ala Ser Gly Tyr Thr Phe Thr Ser Tyr
            20                  25                  30

Trp Met His Trp Val Arg Gln Ala Pro Gly Arg Leu Glu Trp Ile
        35                  40                  45

Gly Asn Ile Asp Pro Ser Asp Ser Glu Thr His Tyr Ala Arg Lys Phe
50                  55                  60

Gln Gly Arg Ala Thr Leu Thr Val Asp Lys Tyr Ser Asp Thr Ala Phe
65                  70                  75                  80

Leu Glu Leu Arg Ser Leu Thr Ser Asp Asp Thr Ala Val Tyr Tyr Cys
                85                  90                  95

Ala Gly Thr Asp Leu Ala Tyr Trp Gly Arg Gly Ala Pro Val Thr Val
            100                 105                 110

Ser Ser

<210> SEQ ID NO 178
<211> LENGTH: 8
<212> TYPE: PRT
<213> ORGANISM: Artificial Sequence
<220> FEATURE:
<223> OTHER INFORMATION: KH2 HCDR1

<400> SEQUENCE: 178

Gly Tyr Thr Phe Thr Ser Tyr Trp
1               5

<210> SEQ ID NO 179
<211> LENGTH: 8
<212> TYPE: PRT
<213> ORGANISM: Artificial Sequence
<220> FEATURE:
<223> OTHER INFORMATION: KH2 HCDR2

<400> SEQUENCE: 179

Ile Asp Pro Ser Asp Ser Glu Thr
1               5

<210> SEQ ID NO 180
<211> LENGTH: 7
<212> TYPE: PRT
<213> ORGANISM: Artificial Sequence
<220> FEATURE:
<223> OTHER INFORMATION: KH2 HCDR3

<400> SEQUENCE: 180

Ala Gly Thr Asp Leu Ala Tyr
1               5

<210> SEQ ID NO 181
<211> LENGTH: 8
<212> TYPE: PRT
<213> ORGANISM: Artificial Sequence
<220> FEATURE:
<223> OTHER INFORMATION: H1 HCDR1

<400> SEQUENCE: 181

Gly Tyr Thr Phe Thr Ser Tyr Val
1               5

<210> SEQ ID NO 182
<211> LENGTH: 8
<212> TYPE: PRT
<213> ORGANISM: Artificial Sequence
<220> FEATURE:
<223> OTHER INFORMATION: H1 HCDR2
```

```
<400> SEQUENCE: 182

Ile Asn Pro Tyr Asn Asp Ala Thr
1               5

<210> SEQ ID NO 183
<211> LENGTH: 11
<212> TYPE: PRT
<213> ORGANISM: Artificial Sequence
<220> FEATURE:
<223> OTHER INFORMATION: H1 HCDR3

<400> SEQUENCE: 183

Ala Arg Gly Gly Tyr Asp Tyr Asp Gly Asp Tyr
1               5                   10

<210> SEQ ID NO 184
<211> LENGTH: 6
<212> TYPE: PRT
<213> ORGANISM: Artificial Sequence
<220> FEATURE:
<223> OTHER INFORMATION: L2 LCDR1

<400> SEQUENCE: 184

Gln Asn Ile Asn Val Trp
1               5

<210> SEQ ID NO 185
<211> LENGTH: 3
<212> TYPE: PRT
<213> ORGANISM: Artificial Sequence
<220> FEATURE:
<223> OTHER INFORMATION: L2 LCDR2

<400> SEQUENCE: 185

Lys Ala Ser
1

<210> SEQ ID NO 186
<211> LENGTH: 9
<212> TYPE: PRT
<213> ORGANISM: Artificial Sequence
<220> FEATURE:
<223> OTHER INFORMATION: L2 LCDR3

<400> SEQUENCE: 186

Gln Gln Gly Gln Ser Tyr Pro Phe Thr
1               5

<210> SEQ ID NO 187
<211> LENGTH: 5
<212> TYPE: PRT
<213> ORGANISM: Artificial Sequence
<220> FEATURE:
<223> OTHER INFORMATION: KH2 HCDR1

<400> SEQUENCE: 187

Ser Tyr Trp Met His
1               5

<210> SEQ ID NO 188
<211> LENGTH: 17
<212> TYPE: PRT
<213> ORGANISM: Artificial Sequence
<220> FEATURE:
<223> OTHER INFORMATION: KH2 HCDR2
```

```
<400> SEQUENCE: 188

Asn Ile Asp Pro Ser Asp Ser Glu Thr His Tyr Ala Gln Lys Phe Gln
1               5                   10                  15

Gly

<210> SEQ ID NO 189
<211> LENGTH: 5
<212> TYPE: PRT
<213> ORGANISM: Artificial Sequence
<220> FEATURE:
<223> OTHER INFORMATION: KH2 HCDR3

<400> SEQUENCE: 189

Thr Asp Leu Ala Tyr
1               5

<210> SEQ ID NO 190
<211> LENGTH: 5
<212> TYPE: PRT
<213> ORGANISM: Artificial Sequence
<220> FEATURE:
<223> OTHER INFORMATION: H1 HCDR1

<400> SEQUENCE: 190

Ser Tyr Val Met His
1               5

<210> SEQ ID NO 191
<211> LENGTH: 17
<212> TYPE: PRT
<213> ORGANISM: Artificial Sequence
<220> FEATURE:
<223> OTHER INFORMATION: H1 HCDR2

<400> SEQUENCE: 191

Tyr Ile Asn Pro Tyr Asn Asp Ala Thr Lys Tyr Ala Arg Lys Phe Gln
1               5                   10                  15

Gly

<210> SEQ ID NO 192
<211> LENGTH: 9
<212> TYPE: PRT
<213> ORGANISM: Artificial Sequence
<220> FEATURE:
<223> OTHER INFORMATION: H1 HCDR3

<400> SEQUENCE: 192

Gly Gly Tyr Asp Tyr Asp Gly Asp Tyr
1               5

<210> SEQ ID NO 193
<211> LENGTH: 11
<212> TYPE: PRT
<213> ORGANISM: Artificial Sequence
<220> FEATURE:
<223> OTHER INFORMATION: L2 LCDR1

<400> SEQUENCE: 193

His Ala Ser Gln Asn Ile Asn Val Trp Leu Ser
1               5                   10

<210> SEQ ID NO 194
<211> LENGTH: 7
<212> TYPE: PRT
<213> ORGANISM: Artificial Sequence
```

```
<220> FEATURE:
<223> OTHER INFORMATION: L2 LCDR2

<400> SEQUENCE: 194

Lys Ala Ser Asn Leu His Thr
1               5

<210> SEQ ID NO 195
<211> LENGTH: 9
<212> TYPE: PRT
<213> ORGANISM: Artificial Sequence
<220> FEATURE:
<223> OTHER INFORMATION: L2 LCDR3

<400> SEQUENCE: 195

Gln Gln Gly Gln Ser Tyr Pro Phe Thr
1               5
```